US007745164B2

(12) United States Patent
Liu et al.

(10) Patent No.: US 7,745,164 B2
(45) Date of Patent: Jun. 29, 2010

(54) METHODS OF MODULATING APOPTOSIS USING INHIBITORS OF BRAIN-LOCALIZED PROTEIN KINASES HOMOLOGOUS TO HOMEODOMAIN-INTERACTING PROTEIN KINASES

(75) Inventors: Wei Liu, Lexington, MA (US); Bradley A. Ozenberger, Olney, MD (US); Leeying Wu, Lexington, MA (US); Ching-Hsiung Frederick Lo, Pennington, NJ (US); Steven A. Haney, Concord, MA (US); Hemchand Sookdeo, Natick, MA (US); Jee Hyung Lee, Boston, MA (US)

(73) Assignee: Wyeth LLC, Madison, NJ (US)

( * ) Notice: Subject to any disclaimer, the term of this patent is extended or adjusted under 35 U.S.C. 154(b) by 441 days.

(21) Appl. No.: 11/645,056

(22) Filed: Dec. 26, 2006

(65) Prior Publication Data

US 2007/0113296 A1    May 17, 2007

Related U.S. Application Data

(62) Division of application No. 10/808,522, filed on Mar. 25, 2004, now abandoned.

(60) Provisional application No. 60/456,958, filed on Mar. 25, 2003, provisional application No. 60/491,251, filed on Jul. 31, 2003.

(51) Int. Cl.
*C12Q 1/48* (2006.01)
(52) U.S. Cl. ........................................... 435/15
(58) Field of Classification Search ................... None
See application file for complete search history.

(56) References Cited

U.S. PATENT DOCUMENTS 6,506,559 B1    1/2003    Driver et al.

FOREIGN PATENT DOCUMENTS

| WO | WO 01/38503 A2 | 5/2001 |
| WO | WO 02/053749 A2 | 7/2002 |
| WO | WO 02/083709 A | 10/2002 |
| WO | WO 2004/006838 A | 1/2004 |

OTHER PUBLICATIONS

Altafaj, X. et al., "Neurodevelopmental delay, motor abnormalities and cognitive deficits in transgenic mice overexpressing Dyrk1a (minibrain), a murine model of Down's syndrome," Hum. Mol. Genet., vol. 10, pp. 1915-1923 (2001).
Arts, G-J. et al., "Adenoviral Vectors Expressing siRNAs for Discovery and Validation of Gene Function," Genome Res., vol. 13, pp. 2325-2332 (2003).
Bairoch, A. And Claverie, J-M., "Sequence patterns in protein kinases," Nature, vol. 331, p. 22 (Jan. 1988).
Bass, B.L., "RNA Interference: The Short Answer," Nature, vol. 411, No. 6836, pp. 428-429 (May 2001).
Bockamp, E. et al., "Of Mice and Models: Improved Animal Models for Biomedical Research," Physiol. Genomics, vol. 11, No. 3, pp. 115-132 (Dec. 2002).
Boise, L.H. et al., "bcl-x, a bcl-2-related gene that functions as a dominant regulator of apoptotic cell death," Cell, vol. 74, pp. 597-608 (Aug. 1993).
Charbonneau, H. and Tonks, N. K., "1002 protein phosphatases?," Annu. Rev. Cell Biol., vol. 8, pp. 463-493 (1992).
D'Orazi, G. et al., "Homeodomain-interacting protein kinase-2 phosphorylates p53 at Ser 46 and mediates apoptosis," Nat. Cell Biol., vol. 4, pp. 11-19 (Jan. 2002).
Duman, R.S. et al., "Neural plasticity to stress and antidepressant treatment," Biol. Psychiatry, vol. 46, pp. 1181-1191 (1999).
Dumas, J., "Growth factor receptor kinase inhibitors: recent progress and clinical impact," Curr. Opin. Drug Discov. Devel., vol. 4, pp. 378-389 (2001).
Egan, S.E. and Weinberg, R.A., "The pathway to signal achievement," Nature, vol. 365, pp. 781-783 (Oct. 1993).
Elbashir, S.M. et al., "Duplexes of 21-Nucleotide RNAs Mediate RNA Interference in Cultured Mammalian Cells," Nature, vol. 411, No. 6836, pp. 494-498 (May 2001).
Elbashir, S.M. et al., "Functional Anatomy of siRNAs for Mediating Efficient RNAi in Drosophila melanogaster Embryo Lysate," EMBO J., vol. 20, No. 23, pp. 6877-6888 (Dec. 2001).
Gage, F.H., "Neurogenesis in the adult brain," J. Neurosci., vol. 22, pp. 612-613 (Feb. 2002).
Galderisi, U. et al., "Antisense Oligonucleotides as Therapeutic Agents," J. Cell Physiol., vol. 181, No. 2, pp. 251-257 (Nov. 1999).
Gao, G. et al., "Non-catalytic beta- and gamma-subunit isoforms of the 5'-AMP-activated protein kinase," J. Biol. Chem., vol. 271, pp. 8675-8681 (Apr. 1996).
Haribabu, B. et al., "Human calcium-calmodulin dependent protein kinase I: cDNA cloning, domain structure and activation by phosphorylation at threonine-177 by calcium-calmodulin dependent protein kinase I kinase," EMBO J., vol. 14, pp. 3679-3686 (1995).
Heasman, J., "Morpholino Oligos: Making Sense of Antisense?," Dev. Biol., vol. 243, No. 2, pp. 209-214 (Mar. 2002).

(Continued)

*Primary Examiner*—Sheridan Swope
(74) *Attorney, Agent, or Firm*—Michael J. Moran

(57) ABSTRACT

The invention provides isolated protein kinase polypeptides related to novel brain-localized protein kinases homologous to known homeodomain-interacting protein kinases (HIPKs), isolated nucleic acid molecules that encode these polypeptides, inhibitors, and methods related thereto. The novel polypeptides and nucleic acid molecules of the invention are termed HIPK4. The invention also provides genetically engineered expression vectors, host cells, and transgenic animals comprising the novel nucleic acid molecules of the invention. The invention additionally provides antisense and RNAi molecules to the nucleic acid molecules of the invention, as well as inhibitors, activators, and antibodies capable of binding to the protein kinase polypeptides of the invention. The invention further provides uses of HIPK4 and its inhibitors, e.g., mutants of HIPK4 lacking protein kinase activity, for modulation of apoptosis, as well as the prevention and treatment of neurological disorders and cancers.

4 Claims, 19 Drawing Sheets

OTHER PUBLICATIONS

Himpel, S. et al., "Specificity determinants of substrate recognition by the protein kinase DYRK1A," J. Biol. Chem., vol. 275:2431-2438 (Jan. 2000).

Hofmann, T.G. et al., "Regulation of p53 activity by its interaction with homeodomain-interacting protein kinase-2," Nat. Cell Biol., vol. 4, pp. 1-10 (Jan. 2002) (plus one page supplementary information).

Hofmann, T.G. et al., "Human homeodomain-interacting protein kinase-2 (HIPK2) is a member of the DYRK family of protein kinases and maps to chromosome 7q32-q34," Biochimie, vol. 82: 1123-1127 (2000).

Hunter, T., "The role of tyrosine phosphorylation in cell growth and disease," Harvey Lect., vol. 94, pp. 81-119 (1998-99).

Jacobs, B.L. et al., "Adult brain neurogenesis and psychiatry: a novel theory of depression," Mol. Psychiatry, vol. 5, pp. 262-269 (2000).

Kaur, G. et al., "Growth inhibition with reversible cell cycle arrest of carcinoma cells by flavone L86-8275," J. Natl. Cancer Inst., vol. 84, pp. 1736-1740, (1992).

Kim, Y.H. et al., "Homeodomain-interacting protein kinases, a novel family of co-repressors for homeodomain transcription factors," J. Biol. Chem., vol. 273, pp. 25875-25879 (Oct. 1998).

Levitzki, A. And Gazit, A., "Tyrosine kinase inhibition: an approach to drug development," Science, vol. 267, pp. 1782-1788 (Mar. 1995).

Li, B. et al., "prk, a cytokine-inducible human protein serine/threonine kinase whose expression appears to be down-regulated in lung carcinomas," J. Biol. Chem., vol. 271, pp. 19402-19408 (Aug. 1996).

Manning, G. et al., "The Protein Kinase Complement of the Human Genome," Science, vol. 298, pp. 1912-1916, 1933-1934 (Dec. 2002).

Micklefield, J., "Backbone Modification of Nucleic Acids: Synthesis, Structure and Therapeutic Applications," Curr. Med. Chem., vol. 8, No. 10, pp. 1157-1179 (Aug. 2001).

Paddison, P.J. et al., "Stable Suppression of Gene Expression by RNAi in Mammalian Cells," Proc. Natl. Acad. Sci. USA, vol. 99, pp. 1443-1448 (Feb. 2002).

Reynolds, A. et al., "Rational siRNA design for RNA interference," Nat. Biotechnol., vol. 22, 326-330 (Mar. 2004).

Rochat-Steiner, V. et al., "FIST/HIPK3: a Fas/FADD-interacting serine/threonine kinase that induces FADD phosphorylation and inhibits fas-mediated Jun NH(2)-terminal kinase activation," J. Exp. Med., vol. 192, pp. 1165-1174 (Oct. 2000).

Sioud, M., "Nucleic Acid Enzymes as a Novel Generation of Anti-gene agents," Curr. Mol. Med., vol. 1, pp. 575-588 (2001).

Song, E. et al., "RNA interference Targeting Fas Protects Mice from Fulminant Hepatitis," Nat. Med., vol. 9, pp. 347-351 (Mar. 2003).

Sridhar, R. et al., "Protein kinases as therapeutic targets," Pharm. Res., vol. 17, pp. 1345-1353 (2000).

Sui, G. et al., "A DNA Vector-based RNAi Technology to Suppress Gene Expression in Mammalian Cells," Proc. Natl. Acad. Sci. USA, vol. 99, pp. 5515-5520 (Apr. 2002).

Tejedor, F. et al., "minibrain: a new protein kinase family involved in postembryonic neurogenesis in Drosophila," Neuron, vol. 14, pp. 287-301 (Feb. 1995).

Turek, T.C. et al., "Development and validation of a competitive AKT serine/threonine kinase fluorescence polarization assay using a product-specific anti-phospho-serine antibody," Anal. Biochem., vol. 299, pp. 45-53 (2001).

Wolfer, D.P. et al., "Knockout mice: simple solutions to the problems of genetic background and flanking genes," Trends Neurosci., vol. 25, pp. 336-340 (Jul. 2002).

Xia, Z. et al., "Calcium influx via the NMDA receptor induces immediate early gene transcription by a MAP kinase/ERK-dependent mechanism," J. Neurosci., vol. 16, pp. 5425-5436 (Sep. 1996).

Yu, J-Y. et al., "RNA interference by Expression of Short-Interfering RNAs and Hairpin RNAs in Mammalian Cells," Proc. Natl. Acad. Sci. USA, vol. 99, pp. 6047-6052 (Apr. 2002).

Database EMBL Human genomic sequence of clone CTC-492K19, XP002293537, Database accession No. AC010271 (Sep. 17, 1999)(2 pgs.).

Database EMBL Mouse genomic sequence of clone RP23-359H6, XP002293536, Database accession No. AC073767 (Jul. 6, 2000)(52 pgs.).

Database UNIPROT 'Online! HIPK4, XP002293538, Database accession No. Q8NE63 (Oct. 1, 2002)(2 pgs.).

Database UNIPROT 'Online! Serine-threonine kinase from macaca, XP002293535, Database accession No. Q8WP28 (Mar. 1, 2002)(2 pgs.).

Database OMIM NCBI; Review concerning HIPK1, XP002293539, Database accession No. 608003 (2 pgs.).

Database OMIM NCBI; Review concerning HIPK2, XP002293540, Database accession No. 606868 (2 pgs.).

Galye et al. (1993) Identification of regions in interleukin-1 alpha important for activity, J. Biol. Chem. 268:22105-11.

Whisstock and Lesk (Aug. 2003) Prediction of protein function from protein sequence and structure, Q. Rev. Biophys. 36:307-40.

Glu-Gly Fragment, Sigma, Inc. Catalogue of Biochemicals and Reagents for Life Science Research, 1997, p. 1159, 2 pages.

A-Genseq_8 Database Accession No. AAU03532 (Plowman et al.) Alignment with SEQ ID No. 2, Sep. 12, 2001, 1 page.

UniProt_7.2 Database Accession No. Q8NE63 (Strausberg et al.) Alignment with SEQ ID No:2, Oct. 1, 2002, 6 pages.

Published Applications_AA_Main US200440197792 (Whyte et al.) Alignment with SEQ ID No. 2, priority date Jul. 15, 2002, 2 pages. Oct. 2004.

FIGURE 1

Target segment starts with AA

| Target segment: 5' -> 3' | GC Ratio | Position | siRNA Sense strand: 5' -> 3'<br>siRNA Antisense strand: 5' -> 3' |
|---|---|---|---|
| AAGATCCTCAAGAATGACGCC<br>[SEQ ID NO:18] | 0.48 | 117 | GAUCCUCAAGAAUGACGCCUU<br>[SEQ ID NO:35]<br>GGCGUCAUUCUUGAGGAUCUU<br>[SEQ ID NO:52] |
| AAGAATGACGCCTACCGCAAC<br>[SEQ ID NO:19] | 0.52 | 126 | GAAUGACGCCUACCGCAACUU<br>[SEQ ID NO:36]<br>GUUGCGGUAGGCGUCAUUCUU<br>[SEQ ID NO:53] |
| AACCGCATCATCAAGAACGAG<br>[SEQ ID NO:20] | 0.48 | 144 | CCGCAUCAUCAAGAACGAGUU<br>[SEQ ID NO:37]<br>CUCGUUCUUGAUGAUGCGGUU<br>[SEQ ID NO:54] |
| AAGAACGAGCTGAAGCTGCTG<br>[SEQ ID NO:21] | 0.52 | 156 | GAACGAGCUGAAGCUGCUGUU<br>[SEQ ID NO:38]<br>CAGCAGCUUCAGCUCGUUCUU<br>[SEQ ID NO:55] |
| AAGGAGCTGGCTATCATCCAC<br>[SEQ ID NO:22] | 0.52 | 381 | GGAGCUGGCUAUCAUCCACUU<br>[SEQ ID NO:39]<br>GUGGAUGAUAGCCAGCUCCUU<br>[SEQ ID NO:56] |
| AAGCCTGAGAACATCATGCTG<br>[SEQ ID NO:23] | 0.48 | 411 | GCCUGAGAACAUCAUGCUGUU<br>[SEQ ID NO:40]<br>CAGCAUGAUGUUCUCAGGCUU<br>[SEQ ID NO:57] |
| AACATCATGCTGGTGGACCAG<br>[SEQ ID NO:24] | 0.52 | 420 | CAUCAUGCUGGUGGACCAGUU<br>[SEQ ID NO:41]<br>CUGGUCCACCAGCAUGAUGUU<br>[SEQ ID NO:58] |
| AAGGTGATTGACTTCGGATCC<br>[SEQ ID NO:25] | 0.48 | 462 | GGUGAUUGACUUCGGAUCCUU<br>[SEQ ID NO:42]<br>GGAUCCGAAGUCAAUCACCUU<br>[SEQ ID NO:59] |
| AAGGAGCCATACATCCAGTCG<br>[SEQ ID NO:26] | 0.52 | 513 | GGAGCCAUACAUCCAGUCGUU<br>[SEQ ID NO:43]<br>CGACUGGAUGUAUGGCUCCUU<br>[SEQ ID NO:60] |
| AACAACGAGTACGACCAGGTG<br>[SEQ ID NO:27] | 0.52 | 651 | CAACGAGUACGACCAGGUGUU<br>[SEQ ID NO:44]<br>CACCUGGUCGUACUCGUUGUU<br>[SEQ ID NO:61] |

FIGURE 1 CONTINUED

| Target segment: 5' -> 3' | GC Ratio | Position | siRNA Sense strand: 5' -> 3'<br>siRNA Antisense strand: 5' -> 3' |
|---|---|---|---|
| AAGTCGTTGGACCAGATTGAG<br>[SEQ ID NO:28] | 0.48 | 855 | GUCGUUGGACCAGAUUGAGUU<br>[SEQ ID NO:45]<br>CUCAAUCUGGUCCAACGACUU<br>[SEQ ID NO:62] |
| AAGAGCATGGTGGAGCTGATC<br>[SEQ ID NO:29] | 0.52 | 951 | GAGCAUGGUGGAGCUGAUCUU<br>[SEQ ID NO:46]<br>GAUCAGCUCCACCAUGCUCUU<br>[SEQ ID NO:63] |
| AATGCGGTCTCCGACATGATG<br>[SEQ ID NO:30] | 0.52 | 1341 | UGCGGUCUCCGACAUGAUGUU<br>[SEQ ID NO:47]<br>CAUCAUGUCGGAGACCGCAUU<br>[SEQ ID NO:64] |
| AAGTCCGACTCCAACTTCAGC<br>[SEQ ID NO:31] | 0.52 | 1485 | GUCCGACUCCAACUUCAGCUU<br>[SEQ ID NO:48]<br>GCUGAAGUUGGAGUCGGACUU<br>[SEQ ID NO:65] |
| AACTTCAGCAACCTCATTCGG<br>[SEQ ID NO:32] | 0.48 | 1497 | CUUCAGCAACCUCAUUCGGUU<br>[SEQ ID NO:49]<br>CCGAAUGAGGUUGCUGAAGUU<br>[SEQ ID NO:66] |
| AACATGACCATGGAAGCTGAG<br>[SEQ ID NO:33] | 0.48 | 1647 | CAUGACCAUGGAAGCUGAGUU<br>[SEQ ID NO:50]<br>CUCAGCUUCCAUGGUCAUGUU<br>[SEQ ID NO:67] |
| AATGGCTGAGTGAGCCAGACT<br>[SEQ ID NO:34] | 0.52 | 1711 | UGGCUGAGUGAGCCAGACUUU<br>[SEQ ID NO:51]<br>AGUCUGGCUCACUCAGCCAUU<br>[SEQ ID NO:68] |

Target segment starts with CA

| Target segment: 5' -> 3' | GC Ratio | Position | siRNA Sense strand: 5' -> 3'<br>siRNA Antisense strand: 5' -> 3' |
|---|---|---|---|
| CAAGATCCTCAAGAATGACGC<br>[SEQ ID NO:69] | 0.48 | 116 | AGAUCCUCAAGAAUGACGCUU<br>[SEQ ID NO:89]<br>GCGUCAUUCUUGAGGAUCUUU<br>[SEQ ID NO:109] |
| CAAGAATGACGCCTACCGCAA<br>[SEQ ID NO:70] | 0.52 | 125 | AGAAUGACGCCUACCGCAAUU<br>[SEQ ID NO:90]<br>UUGCGGUAGGCGUCAUUCUUU<br>[SEQ ID NO:110] |
| CAACCGCATCATCAAGAACGA<br>[SEQ ID NO:71] | 0.48 | 143 | ACCGCAUCAUCAAGAACGAUU<br>[SEQ ID NO:91]<br>UCGUUCUUGAUGAUGCGGUUU<br>[SEQ ID NO:111] |

FIGURE 1 CONTINUED

| | | | |
|---|---|---|---|
| CATCAAGAACGAGCTGAAGCT [SEQ ID NO:72] | 0.48 | 152 | UCAAGAACGAGCUGAAGCUUU [SEQ ID NO:92]<br>AGCUUCAGCUCGUUCUUGAUU [SEQ ID NO:112] |
| CAAGAACGAGCTGAAGCTGCT [SEQ ID NO:73] | 0.52 | 155 | AGAACGAGCUGAAGCUGCUUU [SEQ ID NO:93]<br>AGCAGCUUCAGCUCGUUCUUU [SEQ ID NO:113] |
| CATCCGCTTCCTTGAGTTCTT [SEQ ID NO:74] | 0.48 | 215 | UCCGCUUCCUUGAGUUCUUUU [SEQ ID NO:94]<br>AAGAACUCAAGGAAGCGGAUU [SEQ ID NO:114] |
| CAGAAGGAGAACAACTTCGCG [SEQ ID NO:75] | 0.52 | 297 | GAAGGAGAACAACUUCGCGUU [SEQ ID NO:95]<br>CGCGAAGUUGUUCUCCUUCUU [SEQ ID NO:115] |
| CAAGGAGCTGGCTATCATCCA [SEQ ID NO:76] | 0.52 | 380 | AGGAGCUGGCUAUCAUCCAUU [SEQ ID NO:96]<br>UGGAUGAUAGCCAGCUCCUUU [SEQ ID NO:116] |
| CAAGCCTGAGAACATCATGCT [SEQ ID NO:77] | 0.48 | 410 | AGCCUGAGAACAUCAUGCUUU [SEQ ID NO:97]<br>AGCAUGAUGUUCUCAGGCUUU [SEQ ID NO:117] |
| CAAGGTGATTGACTTCGGATC [SEQ ID NO:78] | 0.48 | 461 | AGGUGAUUGACUUCGGAUCUU [SEQ ID NO:98]<br>GAUCCGAAGUCAAUCACCUUU [SEQ ID NO:118] |
| CATACATCCAGTCGCGCTTCT [SEQ ID NO:79] | 0.52 | 520 | UACAUCCAGUCGCGCUUCUUU [SEQ ID NO:99]<br>AGAAGCGCGACUGGAUGUAUU [SEQ ID NO:119] |
| CAACAACGAGTACGACCAGGT [SEQ ID NO:80] | 0.52 | 650 | ACAACGAGUACGACCAGGUUU [SEQ ID NO:100]<br>ACCUGGUCGUACUCGUUGUUU [SEQ ID NO:120] |
| CACCACTTCTTCAAGCGCAAC [SEQ ID NO:81] | 0.52 | 735 | CCACUUCUUCAAGCGCAACUU [SEQ ID NO:101]<br>GUUGCGCUUGAAGAAGUGGUU [SEQ ID NO:121] |
| CAAGTCGTTGGACCAGATTGA [SEQ ID NO:82] | 0.48 | 854 | AGUCGUUGGACCAGAUUGAUU [SEQ ID NO:102]<br>UCAAUCUGGUCCAACGACUUU [SEQ ID NO:122] |

FIGURE 1 CONTINUED

| Target segment: 5' -> 3' | GC Ratio | Position | siRNA Sense strand: 5' -> 3'<br>siRNA Antisense strand: 5' -> 3' |
|---|---|---|---|
| CAAGAGCATGGTGGAGCTGAT<br>[SEQ ID NO:83] | 0.52 | 950 | AGAGCAUGGUGGAGCUGAUUU<br>[SEQ ID NO:103]<br>AUCAGCUCCACCAUGCUCUUU<br>[SEQ ID NO:123] |
| CAATGCGGTCTCCGACATGAT<br>[SEQ ID NO:84] | 0.52 | 1340 | AUGCGGUCUCCGACAUGAUUU<br>[SEQ ID NO:104]<br>AUCAUGUCGGAGACCGCAUUU<br>[SEQ ID NO:124] |
| CAAGTCCGACTCCAACTTCAG<br>[SEQ ID NO:85] | 0.52 | 1484 | AGUCCGACUCCAACUUCAGUU<br>[SEQ ID NO:105]<br>CUGAAGUUGGAGUCGGACUUU<br>[SEQ ID NO:125] |
| CAACTTCAGCAACCTCATTCG<br>[SEQ ID NO:86] | 0.48 | 1496 | ACUUCAGCAACCUCAUUCGUU<br>[SEQ ID NO:106]<br>CGAAUGAGGUUGCUGAAGUUU<br>[SEQ ID NO:126] |
| CAACATGACCATGGAAGCTGA<br>[SEQ ID NO:87] | 0.48 | 1646 | ACAUGACCAUGGAAGCUGAUU<br>[SEQ ID NO:107]<br>UCAGCUUCCAUGGUCAUGUUU<br>[SEQ ID NO:127] |
| CATGACCATGGAAGCTGAGAG<br>[SEQ ID NO:88] | 0.52 | 1649 | UGACCAUGGAAGCUGAGAGUU<br>[SEQ ID NO:108]<br>CUCUCAGCUUCCAUGGUCAUU<br>[SEQ ID NO:128] |

Target segment starts with GA

| Target segment: 5' -> 3' | GC Ratio | Position | siRNA Sense strand: 5' -> 3'<br>siRNA Antisense strand: 5' -> 3' |
|---|---|---|---|
| GAGATGGTGGCCATCAAGATC<br>[SEQ ID NO:129] | 0.52 | 102 | GAUGGUGGCCAUCAAGAUCUU<br>[SEQ ID NO:144]<br>GAUCUUGAUGGCCACCAUCUU<br>[SEQ ID NO:159] |
| GATGGTGGCCATCAAGATCCT<br>[SEQ ID NO:130] | 0.52 | 104 | UGGUGGCCAUCAAGAUCCUUU<br>[SEQ ID NO:145]<br>AGGAUCUUGAUGGCCACCAUU<br>[SEQ ID NO:160] |
| GATCCTCAAGAATGACGCCTA<br>[SEQ ID NO:131] | 0.48 | 119 | UCCUCAAGAAUGACGCCUAUU<br>[SEQ ID NO:146]<br>UAGGCGUCAUUCUUGAGGAUU<br>[SEQ ID NO:161] |
| GAGTTCCAGAAGGAGAACAAC<br>[SEQ ID NO:132] | 0.48 | 291 | GUUCCAGAAGGAGAACAACUU<br>[SEQ ID NO:147]<br>GUUGUUCUCCUUCUGGAACUU<br>[SEQ ID NO:162] |

FIGURE 1 CONTINUED

| | | | |
|---|---|---|---|
| GATCTCAAGCCTGAGAACATC [SEQ ID NO:133] | 0.48 | 405 | UCUCAAGCCUGAGAACAUCUU [SEQ ID NO:148]<br>GAUGUUCUCAGGCUUGAGAUU [SEQ ID NO:163] |
| GAGAACATCATGCTGGTGGAC [SEQ ID NO:134] | 0.52 | 417 | GAACAUCAUGCUGGUGGACUU [SEQ ID NO:149]<br>GUCCACCAGCAUGAUGUUCUU [SEQ ID NO:164] |
| GAACATCATGCTGGTGGACCA [SEQ ID NO:135] | 0.52 | 419 | ACAUCAUGCUGGUGGACCAUU [SEQ ID NO:150]<br>UGGUCCACCAGCAUGAUGUUU [SEQ ID NO:165] |
| GAAGGAGCCATACATCCAGTC [SEQ ID NO:136] | 0.52 | 512 | AGGAGCCAUACAUCCAGUCUU [SEQ ID NO:151]<br>GACUGGAUGUAUGGCUCCUUU [SEQ ID NO:166] |
| GATTGAGACAGTGAATGGTGG [SEQ ID NO:137] | 0.48 | 869 | UUGAGACAGUGAAUGGUGGUU [SEQ ID NO:152]<br>CCACCAUUCACUGUCUCAAUU [SEQ ID NO:167] |
| GAGACAGTGAATGGTGGCAGT [SEQ ID NO:138] | 0.52 | 873 | GACAGUGAAUGGUGGCAGUUU [SEQ ID NO:153]<br>ACUGCCACCAUUCACUGUCUU [SEQ ID NO:168] |
| GACAGTGAATGGTGGCAGTGT [SEQ ID NO:139] | 0.52 | 875 | CAGUGAAUGGUGGCAGUGUUU [SEQ ID NO:154]<br>ACACUGCCACCAUUCACUGUU [SEQ ID NO:169] |
| GAGCATGGTGGAGCTGATCAA [SEQ ID NO:140] | 0.52 | 953 | GCAUGGUGGAGCUGAUCAAUU [SEQ ID NO:155]<br>UUGAUCAGCUCCACCAUGCUU [SEQ ID NO:170] |
| GAGAAGGCACCAGGTATGCAA [SEQ ID NO:141] | 0.52 | 1248 | GAAGGCACCAGGUAUGCAAUU [SEQ ID NO:156]<br>UUGCAUACCUGGUGCCUUCUU [SEQ ID NO:171] |
| GACTCCAACTTCAGCAACCTC [SEQ ID NO:142] | 0.52 | 1491 | CUCCAACUUCAGCAACCUCUU [SEQ ID NO:157]<br>GAGGUUGCUGAAGUUGGAGUU [SEQ ID NO:172] |
| GACAACATGACCATGGAAGCT [SEQ ID NO:143] | 0.48 | 1644 | CAACAUGACCAUGGAAGCUUU [SEQ ID NO:158]<br>AGCUUCCAUGGUCAUGUUGUU [SEQ ID NO:173] |

FIGURE 1 CONTINUED

Target segment starts with TA

| Target segment: 5' -> 3' | GC Ratio | Position | siRNA Sense strand: 5' -> 3'<br>siRNA Antisense strand: 5' -> 3' |
|---|---|---|---|
| TACCGCAACCGCATCATCAAG<br>[SEQ ID NO:174] | 0.52 | 138 | CCGCAACCGCAUCAUCAAGUU<br>[SEQ ID NO:180]<br>CUUGAUGAUGCGGUUGCGGUU<br>[SEQ ID NO:186] |
| TACGTGAAGGAGCCATACATC<br>[SEQ ID NO:175] | 0.48 | 507 | CGUGAAGGAGCCAUACAUCUU<br>[SEQ ID NO:181]<br>GAUGUAUGGCUCCUUCACGUU<br>[SEQ ID NO:187] |
| TACATCCAGTCGCGCTTCTAC<br>[SEQ ID NO:176] | 0.52 | 522 | CAUCCAGUCGCGCUUCUACUU<br>[SEQ ID NO:182]<br>GUAGAAGCGCGACUGGAUGUU<br>[SEQ ID NO:188] |
| TATGCTCAAGTCGTTGGACCA<br>[SEQ ID NO:177] | 0.48 | 848 | UGCUCAAGUCGUUGGACCAUU<br>[SEQ ID NO:183]<br>UGGUCCAACGACUUGAGCAUU<br>[SEQ ID NO:189] |
| TACTACTGTCTGGCTGAGGAG<br>[SEQ ID NO:178] | 0.52 | 1173 | CUACUGUCUGGCUGAGGAGUU<br>[SEQ ID NO:184]<br>CUCCUCAGCCAGACAGUAGUU<br>[SEQ ID NO:190] |
| TACTGTCTGGCTGAGGAGAAG<br>[SEQ ID NO:179] | 0.52 | 1176 | CUGUCUGGCUGAGGAGAAGUU<br>[SEQ ID NO:185]<br>CUUCUCCUCAGCCAGACAGUU<br>[SEQ ID NO:191] |

FIGURE 2

A
Protein Sequence of Human HIPK4
Total length -- 616 AA
MSTIQSETDCYDIIEVLGKGTFGEVAKGWRRSTGEMVAIKILKNDAYRNRIIKNELKLLHCMRGLDPEEAHVIRFLEFFH
DALKFYLVFELLEQNLFEFQKENNFAPLPARHIRTVTLQVLTALARLKELAIIHADLKPENIMLVDQTRCPFRVKVIDFG
SASIFSEVRYVKEPYIQSRFYRAPEILLGLPFCEKVDVWSLGCVMAELHLGWPLYPGNNEYDQVRYICETQGLPKPHLLH
AACKAHHFFKRNPHPDAANPWQLKSSADYLAETKVRPLERRKYMLKSLDQIETVNGGSVASRLTFPDREALAEHADLKSM
VELIKRMLTWESHERISPSAALRHPFVSMQQLRSAHETTHYYQLSLRSYRLSLQVEGKPPTPVVAAEDGTPYYCLAEEKE
AAGMGSVAGSSPFFREEKAPGMQRAIDQLDDLSLQEAGHGLWGETCTNAVSDMMVPLKAAITGHHVPDSGPEPILAFYSS
RLAGRHKARKPPAGSKSDSNFSNLIRLSQVSPEDDRPCRGSSWEEGEHLGASAEPLAILQRDEDGPNIDNMTMEAERPDP
ELFDPSSCPGEWLSEPDCTLESVRGPRAQGLPPRRSHQHGPPRGATSFLQHVTGHH

B
ATP Binding Domain -- 17-40 (predicted)
LGKGTFGEVAKGWRRSTGEMVAIK

C
Serine/Threonine Binding Domain -- 132-144 (predicted)
IIHADLKPENIML

D
Protein Kinase Domain -- 11-347 (predicted)
YDIIEVLGKGTFGEVAKGWRRSTGEMVAIKILKNDAYRNRIIKNELKLLHCMRGLDPEEAHVIRFLEFFHDALKFYLVFE
LLEQNLFEFQKENNFAPLPARHIRTVTLQVLTALARLKELAIIHADLKPENIMLVDQTRCPFRVKVIDFGSASIFSEVRY
VKEPYIQSRFYRAPEILLGLPFCEKVDVWSLGCVMAELHLGWPLYPGNNEYDQVRYICETQGLPKPHLLHAACKAHHFFK
RNPHPDAANPWQLKSSADYLAETKVRPLERRKYMLKSLDQIETVNGGSVASRLTFPDREALAEHADLKSMVELIKRMLTW
ESHERISPSAALRHPFV

FIGURE 3

A
Protein Sequence of Mouse HIPK4
Total length -- 616 AA
MATIQSETDCYDIIEVLGKGTFGEVAKGWRRSTGEMVAIKILKNDAYRSRIIKNELKLLRCVRGLDPDEAHVIRFLEFFH
DALKFYLVFELLEQNLFEFQKENNFAPLPARHIRTVTLQVLRALARLKELAIIHADLKPENIMLVDQTRCPFRVKVIDFG
SASIFSEVRYVKEPYIQSRFYRAPEILLGLPFCEKVDVWSLGCVMAELHLGWPLYPGNNEYDQVRYICETQGLPKPHLLH
AARKAHHFFKRNPHPDATNPWQLKSSADYLAETKVRPLERRKYMLKSLDQIETVNGGGAVSRLSFPDREALAEHADLKSM
VELIKRMLTWESHERISPSAALRHPFVSMQQLRSAHEATRYYQLSLRGCRLSLQVDGKPPPPVIASAEDGPPYYRLAEEE
ETAGLGGVTGSGSFFREDKAPGMQRAIDQLDDLSLQEARRGLWSDTRADMVSDMLVPLKVASTSHRVPDSGPEPILAFYG
SRLTGRHKARKAPAGSKSDSNFSNLIRLSQASPEDAGPCRGSGWEEGEGRTTSTEPSVIPQREGDGPGIKDRPMDAERPG
PELFDPSSCPGEWLSEPEWTLEGIRGSRAQGLPAHHPHPHGPPRTTSFLQHVGGHH

B
ATP Binding Domain -- 17-40 (predicted)
LGKGTFGEVAKGWRRSTGEMVAIK

C
Serine/Threonine Binding Domain -- 132-144 (predicted)
IIHADLKPENIML

D
Protein Kinase Domain -- 11-347 (predicted)
YDIIEVLGKGTFGEVAKGWRRSTGEMVAIKILKNDAYRSRIIKNELKLLRCVRGLDPDEAHVIRFLEFFHDALKFYLVFE
LLEQNLFEFQKENNFAPLPARHIRTVTLQVLRALARLKELAIIHADLKPENIMLVDQTRCPFRVKVIDFGSASIFSEVRY
VKEPYIQSRFYRAPEILLGLPFCEKVDVWSLGCVMAELHLGWPLYPGNNEYDQVRYICETQGLPKPHLLHAARKAHHFFK
RNPHPDATNPWQLKSSADYLAETKVRPLERRKYMLKSLDQIETVNGGGAVSRLSFPDREALAEHADLKSMVELIKRMLTW
ESHERISPSAALRHPFV

Protein Sequence of Monkey HIPK4
Total length -- 616 AA
MATTQSETDCYDIIEVLGKGTFGEVAKGWRRSTGEMVAIKILKNDAYRNRIIKNELKLLHCMRGLDPEEAHVIRFLEFFH
DALKFYLVFELLEQNLFEFQKENNFAPLPARHIRTVTLQVLRALARLKELAIIHADLKPENIMLVDQTRCPFRVKVIDFG
SASIFSEVRYVKEPYIQSRFYRAPEILLGLPFCEKVDVWSLGCVMAELHLGWPLYPGNNEYDQVRYICETQGLPKPHLLH
AARKAHHFFKRNPHPDAANPWQLKSSADYLAETKVRPLERRKYMLKSLDQIETVNGGSVASRLTFPDREALAEHADLKSM
VELIKRMLTWESHERISPSAALRHPFVSMQQLRNAHETTHYYQLSLRSYRLSLQVEGKPPAPVVAAEDGTPYYRLAEEKE
AAGMGSVASSSPFFREEKAPGMQRAIDQLDDLSLQEAGHGLWGETCTDVVSDMMAPLKAAITGRHMPDSGPEPILAFYSS
RLAGRHKARKPPAGSKSDSNLSNLIRLSQVSPEDDRPCRGSSWEEGEHLGASAEPPAILQRDGDGPNIDNMTMEAERPDP
ELFDPSSCPGEWLSEPDWTLEGVRGPRAQGLPPRRSHQHGPPRGATSFLQHVTGHH

B

ATP Binding Domain -- 17-40 (predicted)
LGKGTFGEVAKGWRRSTGEMVAIK

C

Serine/Threonine Binding Domain -- 132-144 (predicted)
IIHADLKPENIML

D

Protein Kinase Domain -- 11-347 (predicted)
YDIIEVLGKGTFGEVAKGWRRSTGEMVAIKILKNDAYRNRIIKNELKLLHCMRGLDPEEAHVIRFLEFFHDALKFYLVFE
LLEQNLFEFQKENNFAPLPARHIRTVTLQVLRALARLKELAIIHADLKPENIMLVDQTRCPFRVKVIDFGSASIFSEVRY
VKEPYIQSRFYRAPEILLGLPFCEKVDVWSLGCVMAELHLGWPLYPGNNEYDQVRYICETQGLPKPHLLHAARKAHHFFK
RNPHPDAANPWQLKSSADYLAETKVRPLERRKYMLKSLDQIETVNGGSVASRLTFPDREALAEHADLKSMVELIKRMLTW
ESHERISPSAALRHPFV

FIGURE 5

A
Protein Sequence of Rat HIPK4
Total length -- 616 AA
MATIQSETDCYDIIEVLGKGTFGEVAKGWRRSTGEMVAIKILKNDAYRSRIIKNELKLLRCVRGLDPDEAHVIRFLEFFH
DALKFYLVFELLEQNLFEFQKENNFAPLPARHIRTVTLQVLRALARLKELAIIHADLKPENIMLVDQTRCPFRVKVIDFG
SASIFSEVRYVKEPYIQSRFYRAPEILLGLPFCEKVDVWSLGCVMAELHLGWPLYPGNNEYDQVRYICETQGLPKPHLLH
AARKAHHFFKRNPHPDATNPWQLKSSADYLAETKVRPLERRKYMLKSLDQIETVNGGGAVSRLSFPDREALAEHADLKSM
VELIKRMLTWESHERISPSAALRHPFVSMQQLRSAHEATRYYQLSLRGCRLSLQVDGKPPPPVIASAEDGPPYYRLAEEE
ETAGLGGVTGSGSFFREDKAPGMQRAIDQLDDLSLQEARRGLWSDTRADMVSDMLVPLKVASTSHRVPDSGPEPILAFYG
SRLTGRHKARKAPAGSKSDSNFSNLIRLSQASPEDAGPCRGSGWEEGEGRTTSTEPSVIPQREGDGPGIKDRPMDAERPG
PELFDPSSCPGEWLSEPEWTLEGIRGSRAQGLPAHHPHPHGPPRTTSFLQHVGGHH

B
ATP Binding Domain -- 17-40 (predicted)
LGKGTFGEVAKGWRRSTGEMVAIK

C
Serine/Threonine Binding Domain -- 132-144 (predicted)
IIHADLKPENIML

D
Protein Kinase Domain -- 11-347 (predicted)
YDIIEVLGKGTFGEVAKGWRRSTGEMVAIKILKNDAYRSRIIKNELKLLRCVRGLDPDEAHVIRFLEFFHDALKFYLVFE
LLEQNLFEFQKENNFAPLPARHIRTVTLQVLRALARLKELAIIHADLKPENIMLVDQTRCPFRVKVIDFGSASIFSEVRY
VKEPYIQSRFYRAPEILLGLPFCEKVDVWSLGCVMAELHLGWPLYPGNNEYDQVRYICETQGLPKPHLLHAARKAHHFFK
RNPHPDATNPWQLKSSADYLAETKVRPLERRKYMLKSLDQIETVNGGGAVSRLSFPDREALAEHADLKSMVELIKRMLTW
ESHERISPSAALRHPFV

CLUSTAL W multiple sequence alignment results

MSF: 346   Type: P    Check: 4900   ..

```
Name: mushipk3_np_034564.kd.pep          oo    Len: 346    Check: 9189   Weight:  7.5
Name: rathipk3_np_113975.kd.fas.pep      oo    Len: 346    Check:  347   Weight:  6.5
Name: humhipk3_np_005725.kd.pep          oo    Len: 346    Check: 9094   Weight:  7.8
Name: humhipk1-like_ax318266.kd.pep      oo    Len: 346    Check:  773   Weight:  6.8
Name: mushipk1_np_034562.kd.pep          oo    Len: 346    Check:  878   Weight:  7.0
Name: humhipk2_np_073577.kd.fas.pep      oo    Len: 346    Check:   11   Weight:  6.7
Name: mushipk2_np_034563.kd.pep          oo    Len: 346    Check: 1047   Weight:  7.7
Name: wormf20b6_q19632.kd.pep            oo    Len: 346    Check: 9639   Weight: 16.4
Name: humhipk4.kd.fas.pep                oo    Len: 346    Check: 4355   Weight:  5.4
Name: monkeyhipk4_ab074449.kd.fas.pe     oo    Len: 346    Check: 4346   Weight:  5.3
Name: mushipk4.kd.fas.pep                oo    Len: 346    Check: 5897   Weight:  5.4
Name: rathipk4_xp_218355.kd.fas.pep      oo    Len: 346    Check: 5822   Weight:  4.8
Name: yeastyak1_np_012394.kd.fas.pep     oo    Len: 346    Check: 3415   Weight: 12.2
Name: dmcg17090_q95tg3.kd.pep            oo    Len: 346    Check:   87   Weight: 26.0
```

//

```
                1                                                       50
mushipk3_np_    YEVLDFLGRG  TFGQVVKCWK  RGTNEIVAIK  ILKNHPSYAR  QGQIEVSILA
rathipk3_np_    YEVLDFLGRG  TFGQVVKCWK  RGTNEIVAIK  ILKNHPSYAR  QGQIEVSILA
humhipk3_np_    YEVLDFLGRG  TFGQVVKCWK  RGTNEIVAIK  ILKNHPSYAR  QGQIEVSILA
humhipk1-lik    YEVLEFLGRG  TFGQVAKCWK  RSTKEIVAIK  ILKNHPSYAR  QGQIEVSILS
mushipk1_np_    YEVLEFLGRG  TFGQVAKCWK  RSTKEIVAIK  ILKNHPSYAR  QGQIEVSILS
humhipk2_np_    YEVLEFLGRG  TFGQVVKCWK  RGTNEIVAIK  ILKNHPSYAR  QGQIEVSILA
mushipk2_np_    YEVLEFLGRG  TFGQVVKCWK  RGTNEIVAIK  ILKNHPSYAR  QGQIEVSILA
wormf20b6_q1    YEVLEFLGKG  TFGQVVKAWK  KGTSEIVAIK  ILKKHPSYAR  QGQIEVSILS
humhipk4.kd.    YDIIEVLGKG  TFGEVAKGWR  RSTGEMVAIK  ILKNDAYRNR  IIKNELKLLH
monkeyhipk4_    YDIIEVLGKG  TFGEVAKGWR  RSTGEMVAIK  ILKNDAYRNR  IIKNELKLLH
mushipk4.kd.    YDIIEVLGKG  TFGEVAKGWR  RSTGEMVAIK  ILKNDAYRSR  IIKNELKLLR
rathipk4_xp_    YDIIEVLGKG  TFGEVAKGWR  RSTGEMVAIK  ILKNDAYRSR  IIKNELKLLR
yeastyak1_np    YLVLDILGQG  TFGQVVKCQN  LLTKEILAVK  VVKSRTEYLT  QSITEAKILE
dmcg17090_q9    ...YIFNCLD  DIGQVNVPTD  LEGGQLLAEK  TDRREFIDLL  KRMLTIDQER 51                                                     100
mushipk3_np_    RLSTENA..D  EYNFVRAYEC  FQHRNHTCLV  FEMLEQNLYD  FLKQNKFSPL
rathipk3_np_    RLSTENA..D  EYNFVRAYEC  FQHRNHTCLV  FEMLEQNLYD  FLKQNKFSPL
humhipk3_np_    RLSTENA..D  EYNFVRAYEC  FQHRNHTCLV  FEMLEQNLYD  FLKQNKFSPL
humhipk1-lik    RLSSENA..D  EYNFVRSYEC  FQHKNHTCLV  FEMLEQNLYD  FLKQNKFSPL
mushipk1_np_    RLSSENA..D  EYNFVRSYEC  FQHKNHTCLV  FEMLEQNLYD  FLKQNKFSPL
humhipk2_np_    RLSTESA..D  DYNFVRAYEC  FQHKNHTCLV  FEMLEQNLYD  FLKQNKFSPL
mushipk2_np_    RLSTESA..D  DYNFVRAYEC  FQHKNHTCLV  FEMLEQNLYD  FLKQNKFSPL
wormf20b6_q1    RLSNENS..E  EFNFVRAFEC  FNHKSHTCLV  FEMLEQNLYD  FLKQNKFMPL
humhipk4.kd.    CMRGLDP..E  EAHVIRFLEF  FHDALKFYLV  FELLEQNLFE  FQKENNFAPL
monkeyhipk4_    CMRGLDP..E  EAHVIRFLEF  FHDALKFYLV  FELLEQNLFE  FQKENNFAPL
mushipk4.kd.    CVRGLDP..D  EAHVIRFLEF  FHDALKFYLV  FELLEQNLFE  FQKENNFAPL
rathipk4_xp_    CVRGLDP..D  EAHVIRFLEF  FHDALKFYLV  FELLEQNLFE  FQKENNFAPL
yeastyak1_np    LLNQKIDPTN  KHHFLRMYDS  FVHKNHLCLV  FELLSNNLYE  LLKQNKFHGL
dmcg17090_q9    RLTPAEALNH  SFTRLTHLVD  YVYCNNVKAS  VQMMEVCRRG  DFHTVQPAST
```

FIGURE 6 CONTINUED

```
                 101                                                     150
mushipk3_np_     PLKVIRPVLQ QVATALKKLK SLGLIHADLK PENIMLVDPV RQPYRVKVID
rathipk3_np_     PLKVIRPVLQ QVATALKKLK SLGLIHADLK PENIMLVDPV RQPYRVKVID
humhipk3_np_     PLKVIRPILQ QVATALKKLK SLGLIHADLK PENIMLVDPV RQPYRVKVID
humhipk1-lik     PLKYIRPILQ QVATALMKLK SLGLIHADLK PENIMLVDPV RQPYRVKVFD
mushipk1_np_     PLKYIRPILQ QVATALMKLK SLGLIHADLK PENIMLVDPV RQPYRVKVID
humhipk2_np_     PLKYIRPVLQ QVATALMKLK SLGLIHADLK PENIMLVDPS RQPYRVKVID
mushipk2_np_     PLKYIRPVLQ QVATALMKLK SLGLIHADLK PENIMLVDPS RQPYRVKVID
wormf20b6_q1     PLNAIRPILF QVLTALLKLK SLGLIHADLK PENIMLVDPQ QQPYRVKVID
humhipk4.kd.     PARHIRTVTL QVLTALARLK ELAIIHADLK PENIMLVDQT RCPFRVKVID
monkeyhipk4_     PARHIRTVTL QVLRALARLK ELAIIHADLK PENIMLVDQT RCPFRVKVID
mushipk4.kd.     PARHIRTVTL QVLRALARLK ELAIIHADLK PENIMLVDQT RCPFRVKVID
rathipk4_xp_     PARHIRTVTL QVLRALARLK ELAIIHADLK PENIMLVDQT RCPFRVKVID
yeastyak1_np     SIQLIRTFTT QILDSLCVLK ESKLIHCDLK PENILLCAPD KP..ELKIID
dmcg17090_q9     LVTNFVPSST ENMTFTINNQ LTSQVQRLVR DGRPLAYEGL YQIYNGRSVA 151                                                     200
mushipk3_np_     FGSASHVSKT ..VCSTYLQS RYYRAPEIIL GLPFCEAIDM WSLGCVIAEL
rathipk3_np_     FGSASHVSKT ..VCSTYLQS RYYRAPEIIL GLPFCEAIDM WSLGCVIAEL
humhipk3_np_     FGSASHVSKT ..VCSTYLQS RYYRAPEIIL GLPFCEAIDM WSLGCVIAEL
humhipk1-lik     FGSASHVSKA ..VCSTYLQS RYYRAPEIIL GLPFCEAIDM WSLGCVIAEL
mushipk1_np_     FGSASHVSKA ..VCSTYLQS RYYRAPEIIL GLPFCEAIDM WSLGCVIAEL
humhipk2_np_     FGSASHVSKA ..VCSTYLQS RYYRAPEIIL GLPFCEAIDM WSLGCVIAEL
mushipk2_np_     FGSASHVSKA ..VCSTYLQS RYYRAPEIIL GLPFCEAIDM WSLGCVIAEL
wormf20b6_q1     FGSASHRSKA ..VTNTYLQS RYYRAPEIIL GLPFNESIDM WSLGCVIAEL
humhipk4.kd.     FGSASIFSEV RYVKEPYIQS RFYRAPEILL GLPFCEKVDV WSLGCVMAEL
monkeyhipk4_     FGSASIFSEV RYVKEPYIQS RFYRAPEILL GLPFCEKVDV WSLGCVMAEL
mushipk4.kd.     FGSASIFSEV RYVKEPYIQS RFYRAPEILL GLPFCEKVDV WSLGCVMAEL
rathipk4_xp_     FGSASIFSEV RYVKEPYIQS RFYRAPEILL GLPFCEKVDV WSLGCVMAEL
yeastyak1_np     FGSSCEEART ...VYTYIQS RFYRAPEIIL GIPYSTSIDM WSLGCIVAEL
dmcg17090_q9     RQYP...... ....QTRTDS FQHQLVSNIL CPPSYQTMPS PTKHVVVGSA 201                                                     250
mushipk3_np_     FLGWPLYPGA LEHDQIRYIS QTQGLPGEQL LNVGTKSTRF FCRE......
rathipk3_np_     FLGWPLYPGA LEYDQIRYIS QTQGLPGEQL LNVGTKSTRF FCRE......
humhipk3_np_     FLGWPLYPGA LEYDQIRYIS QTQGLPGEQL LNVGTKSTRF FCKE......
humhipk1-lik     FLGWPLYPGA SEYDQIRYIS QTQGLPAEYL LSAGTKTTRF FNRD......
mushipk1_np_     FLGWPLYPGA SEYDQIRYIS QTQGLPAEYL LSAGTKTTRF FNRD......
humhipk2_np_     FLGWPLYPGA SEYDQIRYIS QTQGLPAEYL LSAGTKTTRF FNRD......
mushipk2_np_     FLGWPLYPGA SEYDQIRYIS QTQGLPAEYL LSAGTKTTRF FNRD......
wormf20b6_q1     FLGWPLYPGS SEYDQIRFII QTQGLPPTSM LESASKLHRF FKEVKSESPN
humhipk4.kd.     HLGWPLYPGN NEYDQVRYIC ETQGLPKPHL LHAACKAHHF FKRNP.....
monkeyhipk4_     HLGWPLYPGN NEYDQVRYIC ETQGLPKPHL LHAARKAHHF FKRNP.....
mushipk4.kd.     HLGWPLYPGN NEYDQVRYIC ETQGLPKPHL LHAARKAHHF FKRNP.....
rathipk4_xp_     HLGWPLYPGN NEYDQVRYIC ETQGLPKPHL LHAARKAHHF FKRNP.....
yeastyak1_np     FLGIPIFPGA SEYNQLTRII DTLGYPPSWM IDMGKNSGKF MKKLAPEE..
dmcg17090_q9     TMQPPLQVPP QQYVNVPVPV SMVEPTSGQR MLLTNRVQAS GVAWPQTG..
```

FIGURE 6 CONTINUED

```
              251                                                        300
mushipk3_np_  .TDMSHSGWR LKTLEEHEAE TG.MKSKEAR KYIFNSLDDI VHVN.....T
rathipk3_np_  .TDMSHSGWR LKTLEEHEAE TG.MKSKEAR KYIFNSLDDI VHVN.....T
humhipk3_np_  .TDMSHSGWR LKTLEEHEAE TG.MKSKEAR KYIFNSLDDV AHVN.....T
humhipk1-lik  .PNLGYPLWR LKTPEEHELE TG.IKSKEAR KYIFNCLDDM AQVN.....M
mushipk1_np_  .PNLGYPLWR LKTPEEHELE TG.IKSKEAR KYIFNCLDDM AQVN.....M
humhipk2_np_  .TDSPYPLWR LKTPDDHEAE TG.IKSKEAR KYIFNCLDDM AQVN.....M
mushipk2_np_  .TDSPYPLWR LKTPDDHEAE TG.TKSKEAR KYIFNCLDDM AQGN.....M
wormf20b6_q1  HTNVGGSYYR LKTVEEYEAS SSTAKSKETR KYIFNVIDDI SRVC.....Y
humhipk4.kd.  .HPDAANPWQ LKSSADYLAE TK.VRPLERR KYMLKSLDQI ETVNGGSVAS
monkeyhipk4_  .HPDAANPWQ LKSSADYLAE TK.VRPLERR KYMLKSLDQI ETVNGGSVAS
mushipk4.kd.  .HPDATNPWQ LKSSADYLAE TK.VRPLERR KYMLKSLDQI ETVNGGGAVS
rathipk4_xp_  .HPDATNPWQ LKSSADYLAE TK.VRPLERR KYMLKSLDQI ETVNGGGAVN
yeastyak1_np  .SSSSTQKHR MKTIEEFCRE YNIVEKPSKQ YFKWRKLPDI IRNYR..YPK
dmcg17090_q9  RQMALVPSWP QQAPAHSLIV DSTPLFNVEE IYPKHHLNLP RNDLKKESPA 301                                                        346
mushipk3_np_  VMDLEGGDLL AEKADRREFV NLLKKMLLID ADLRITPIET LNHPFV
rathipk3_np_  VMDLEGSDLL AEKADRREFV SLLKKMLLID ADLRITPIET LNHPFV
humhipk3_np_  VMDLEGSDLL AEKADRREFV SLLKKMLLID ADLRITPAET LNHPFV
humhipk1-lik  STDLEGTDML AEKADRREYI DLLKKMLTID ADKRITPLKT LNHQFV
mushipk1_np_  STDLEGTDML AEKADRREYI DLLKKMLTID ADKRITPLKT LNHQFV
humhipk2_np_  TTDLEGSDML VEKADRREFI DLLKKMLTID ADKRITPIET LNHPFV
mushipk2_np_  TTDLEGSDML VEKADRREFI DLLKKMLTID ADKRVTPIET LNHPFV
wormf20b6_q1  GFESDPVEHL CDRIDRQEFV DVLKKMLVLN PDFRITPAEG LESKFV
humhipk4.kd.  RLTFPDREAL AEHADLKSMV ELIKRMLTWE SHERISPSAA LRHPFV
monkeyhipk4_  RLTFPDREAL AEHADLKSMV ELIKRMLTWE SHERISPSAA LRHPFV
mushipk4.kd.  RLSFPDREAL AEHADLKSMV ELIKRMLTWE SHERISPSAA LRHPFV
rathipk4_xp_  RLSFPDREAL AEHADLKSMV ELIKRMLTWE SHERISPSAA LRHPFV
yeastyak1_np  SIQNSQELID QEMQNRECLI HFLGGVLNLN PLERWTPQQA MLHPFI
dmcg17090_q9  HHIAKGNSYR VPRHEKKEHQ QLSPVKKRVK ESSPPHQQRY QRAAHV
```

CLUSTAL W multiple sequence alignment results

MSF: 340   Type: P    Check: 1950   ..

```
Name: musdyrk1a_np_031916.kd.pep   oo    Len: 340   Check: 8276   Weight: 2.2
Name: ratdyrk1a_np_036923.kd.pep   oo    Len: 340   Check: 8276   Weight: 2.2
Name: humdyrk1a_np_001387.kd.pep   oo    Len: 340   Check: 8161   Weight: 2.2
Name: humdyrk1b_np_004705.kd.pep   oo    Len: 340   Check: 7992   Weight: 3.5
Name: musdyrk1b_np_034222.kd.pep   oo    Len: 340   Check: 6091   Weight: 2.6
Name: dmmnb_aaf48776.kd.pep   oo    Len: 340   Check: 7580   Weight: 5.3
Name: wormt04c10_q22155.kd.pep   oo    Len: 340   Check: 9628   Weight: 8.0
Name: dmsmi35a_q9v3d5.kd.pep   oo    Len: 340   Check: 6217   Weight: 8.4
Name: humdyrk4_dyr4_human.kd.pep   oo    Len: 340   Check: 1420   Weight: 8.0
Name: humdyrk2_np_006473.kd.pep   oo    Len: 340   Check: 8233   Weight: 6.6
Name: humdyrk3_np_003573.kd.pep   oo    Len: 340   Check: 8166   Weight: 7.5
Name: wormf49e11_q20604.kd.pep   oo    Len: 340   Check: 7542   Weight: 7.5
Name: kab7_schpo.kd.pep   oo    Len: 340   Check: 9798   Weight: 11.1
Name: pom1_schpo.kd.pep   oo    Len: 340   Check: 8379   Weight: 9.8
Name: humhipk4.kd.pep   oo    Len: 340   Check: 8285   Weight: 3.5
Name: monkeyhipk4_ab074449.kd.fas.pe   oo    Len: 340   Check: 8293   Weight: 3.5
Name: mushipk4.kd.pep   oo    Len: 340   Check: 9829   Weight: 3.5
Name: rathipk4_xp_218355.kd.pep   oo    Len: 340   Check: 9784   Weight: 3.5
```

```
//
                        1                                                     50
musdyrk1a_np   YEIDSLIGKG  SFGQVVKAYD  RVEQEWVAIK  IIKNKKAFLN  QAQIEVRLLE
ratdyrk1a_np   YEIDSLIGKG  SFGQVVKAYD  RVEQEWVAIK  IIKNKKAFLN  QAQIEVRLLE
humdyrk1a_np   YEIDSLIGKG  SFGQVVKAYD  RVEQEWVAIK  IIKNKKAFLN  QAQIEVRLLE
humdyrk1b_np   YEIDSLIGKG  SFGQVVKAYD  HQTQELVAIK  IIKNKKAFLN  QAQIELRLLE
musdyrk1b_np   YEIDSLIGKG  SFGQVVKAYD  HQTQELVAIK  IIKNKKAFLN  QAQIELRLLE
dmmnb_aaf487   YEIDSLIGKG  SFGQVVKAYD  HEEQCHVAIK  IIKNKKPFLN  QAQIEVKLLE
wormt04c10_q   ILSDTPVGKG  SFGQVTKAYD  TLNKEEVAIK  IIKNKKTFFD  QAQIEIHLLE
dmsmi35a_q9v   YEILEVIGKG  SFGQVIRALD  HKTNTHVAIK  IIRNKKRFLN  QAVVELNILD
humdyrk4_dyr   YEVLETIGKG  SFGQVAKCLD  HKNNELVALK  IIRNKKRFHQ  QALMELKILE
humdyrk2_np_   YEVLKVIGKG  SFGQVVKAYD  HKVHQHVALK  MVRNEKRFHR  QAAEEIRILE
humdyrk3_np_   YEVLKIIGKG  SFGQVARVYD  HKLRQYVALK  MVRNEKRFHR  QAAEEIRILE
wormf49e11_q   YEVLKVIGKG  SFGQVIKAFD  HKYQQYVALK  LVRNEKRFHR  QADEEIRILD
kab7_schpo.k   YEIIDTVGKG  SFGQVLKCID  HKRGQVVAIK  VIKNRQKFHG  QTLVEVGILK
pom1_schpo.k   YEVVDFLGKG  SFGQVLRCID  YETGKLVALK  IIRNKKRFHM  QALVETKILQ
humhipk4.kd.   YDIIEVLGKG  TFGEVAKGWR  RSTGEMVAIK  ILKNDAYRNR  IIKNELKLLH
monkeyhipk4_   YDIIEVLGKG  TFGEVAKGWR  RSTGEMVAIK  ILKNDAYRNR  IIKNELKLLH
mushipk4.kd.   YDIIEVLGKG  TFGEVAKGWR  RSTGEMVAIK  ILKNDAYRSR  IIKNELKLLR
rathipk4_xp_   YDIIEVLGKG  TFGEVAKGWR  RSTGEMVAIK  ILKNDAYRSR  IIKNELKLLR
```

FIGURE 7 CONTINUED

```
                51                                                                  100
musdyrk1a_np    LMNKHDTEMK  YYIVHLKRHF  MFRNHLCLVF  EMLSYNLYDL  LRNTNFRGVS
ratdyrk1a_np    LMNKHDTEMK  YYIVHLKRHF  MFRNHLCLVF  EMLSYNLYDL  LRNTNFRGVS
humdyrk1a_np    LMNKHDTEMK  YYIVHLKRHF  MFRNHLCLVF  EMLSYNLYDL  LRNTNFRGVS
humdyrk1b_np    LMNQHDTEMK  YYIVHLKRHF  MFRNHLCLVF  ELLSYNLYDL  LRNTHFRGVS
musdyrk1b_np    LMNQHDTEMK  YYIVHLKRHF  MFRNHLCLVF  ELLSYNLYDL  LRNTHFRGVS
dmmnb_aaf487    MMNRADAENK  YYIVKLKRHF  MWRNHLCLVF  ELLSYNLYDL  LRNTNFRGVS
wormt04c10_q    LTNAHDKDNK  YNIVTLKGHF  VHRAHLCLVF  ELLSYNLYDL  LKNTSFRGVS
dmsmi35a_q9v    ELREKDADGS  HNVIHMLDYT  YFRKHLCITF  ELMSLNLYEL  IKKNNYNGFS
humdyrk4_dyr    ALRKKDKDNT  YNVVHMKDFF  YFRNHFCITF  ELLGINLYEL  MKNNNFQGFS
humdyrk2_np_    HLRKQDKDNT  MNVIHMLENF  TFRNHICMTF  ELLSMNLYEL  IKKNKFQGFS
humdyrk3_np_    HLKKQDKTGS  MNVIHMLESF  TFRNHVCMAF  ELLSIDLYEL  IKKNKFQGFS
wormf49e11_q    HLRRQDSDGT  HNIIHMLDYF  NFRNHKCITF  ELLSINLYEL  IKRNKFQGFS
kab7_schpo.k    RLCEADPADK  NNVIRYLSHF  DFRGHLCIVT  ELLGSNLFDV  IRENNYKGLP
pom1_schpo.k    KIREWDPLDE  YCMVQYTDHF  YFRDHLCVAT  ELLGKNLYEL  IKSNGFKGLP
humhipk4.kd.    CMRGLDPE.E  AHVIRFLEFF  HDALKFYLVF  ELLEQNLFEF  QKENNFAPLP
monkeyhipk4_    CMRGLDPE.E  AHVIRFLEFF  HDALKFYLVF  ELLEQNLFEF  QKENNFAPLP
mushipk4.kd.    CVRGLDPD.E  AHVIRFLEFF  HDALKFYLVF  ELLEQNLFEF  QKENNFAPLP
rathipk4_xp_    CVRGLDPD.E  AHVIRFLEFF  HDALKFYLVF  ELLEQNLFEF  QKENNFAPLP 101                                                                 150
musdyrk1a_np    LNLTRKFAQQ  MCTALLFLAT  PELSIIHCDL  KPENILLCNP  KRS..AIKIV
ratdyrk1a_np    LNLTRKFAQQ  MCTALLFLAT  PELSIIHCDL  KPENILLCNP  KRS..AIKIV
humdyrk1a_np    LNLTRKFAQQ  MCTALLFLAT  PELSIIHCDL  KPENILLCNP  KRS..AIKIV
humdyrk1b_np    LNLTRKLAQQ  LCTALLFLAT  PELSIIHCDL  KPENILLCNP  KRS..AIKIV
musdyrk1b_np    LNLTRKLAQQ  LCTALLFLAT  PELSIIHCDL  KPENILLCNP  KRS..AIKIV
dmmnb_aaf487    LNLTRKFAQQ  LCTALLFLST  PELNIIHCDL  KPENILLCNP  KRS..AIKIV
wormt04c10_q    LNLARKFAQQ  LGKTLLFLSS  PELSIIHCDL  KPENVLLVNA  KRS..QIRVI
dmsmi35a_q9v    MSLIRRFCNS  IVKCLRLLY.  .KENIIHCDL  KPENILLKQR  GSS..SIKVI
humdyrk4_dyr    LSIVRRFTLS  VLKCLQMLS.  .VEKIIHCDL  KPENIVLYQK  GQA..SVKVI
humdyrk2_np_    LPLVRKFAHS  ILQCLDALH.  .KNRIIHCDL  KPENILLKQQ  GRS..GIKVI
humdyrk3_np_    VQLVRKFAQS  ILQSLDALH.  .KNKIIHCDL  KPENILLKHH  GRS..STKVI
wormf49e11_q    LMLVRKFAYS  MLLCLDLLQ.  .KNRLIHCDL  KPENVLLKQQ  GRS..GIKVI
kab7_schpo.k    LIVVKSFALQ  GLQALRLLQ.  .GQNIIHCDL  KPENLLLSHP  LKA..RIKLI
pom1_schpo.k    IVVIKSITRQ  LIQCLTLLN.  .EKHVIHCDL  KPENILLCHP  FKS..QVKVI
humhipk4.kd.    ARHIRTVTLQ  VLTALARLK.  .ELAIIHADL  KPENIMLVDQ  TRCPFRVKVI
monkeyhipk4_    ARHIRTVTLQ  VLRALARLK.  .ELAIIHADL  KPENIMLVDQ  TRCPFRVKVI
mushipk4.kd.    ARHIRTVTLQ  VLRALARLK.  .ELAIIHADL  KPENIMLVDQ  TRCPFRVKVI
rathipk4_xp_    ARHIRTVTLQ  VLRALARLK.  .ELAIIHADL  KPENIMLVDQ  TRCPFRVKVI
```

FIGURE 7 CONTINUED

```
                                                                        200
musdyrkla_np  DFGSSCQLGQ  R...IYQYIQ  SRFYRSPEVL  LGMPYDLAID  MWSLGCILVE
ratdyrkla_np  DFGSSCQLGQ  R...IYQYIQ  SRFYRSPEVL  LGMPYDLAID  MWSLGCILVE
humdyrkla_np  DFGSSCQLGQ  R...IYQYIQ  SRFYRSPEVL  LGMPYDLAID  MWSLGCILVE
humdyrklb_np  DFGSSCQLGQ  R...IYQYIQ  SRFYRSPEVL  LGTPYDLAID  MWSLGCILVE
musdyrklb_np  DFGSSCQLGQ  R...IYQYIQ  SRFYRSPEVL  LGTPYDLAID  MWSLGCILVE
dmmnb_aaf487  DFGSSCQLGQ  R...IYHYIQ  SRFYRSPEVL  LGIQYDLAID  MWSLGCILVE
wormt04c10_q  DFGSSCQTGH  R...IYQYIQ  SRFYRSPEVL  LGIAYDTKID  MWSLGCILVE
dmsmi35a_q9v  DFGSSCYVDR  K...IYTYIQ  SRFYRSPEVI  LGLQYGTAID  MWSLGCILAE
humdyrk4_dyr  DFGSSCYEHQ  K...VYTYIQ  SRFYRSPEVI  LGHPYDVAID  MWSLGCITAE
humdyrk2_np_  DFGSSCYEHQ  R...VYTYIQ  SRFYRAPEVI  LGARYGMPID  MWSLGCILAE
humdyrk3_np_  DFGSSCFEYQ  K...LYTYIQ  SRFYRAPEII  LGSRYSTPID  IWSFRCILAE
wormf49e11_q  DFGSSCFDDQ  R...IYTYIQ  SRFYRAPEVI  LGTKYGMPID  MWSLGCILAE
kab7_schpo.k  DFGSSCFYNE  K...VYTYLQ  SRFYRAPEII  LGLEYGKEID  IWSFGCILAE
pom1_schpo.k  DFGSSCFEGE  C...VYTYIQ  SRFYRSPEVI  LGMGYGTPID  VWSLGCIIAE
humhipk4.kd.  DFGSASIFSE  VRYVKEPYIQ  SRFYRAPEIL  LGLPFCEKVD  VWSLGCVMAE
monkeyhipk4_  DFGSASIFSE  VRYVKEPYIQ  SRFYRAPEIL  LGLPFCEKVD  VWSLGCVMAE
mushipk4.kd.  DFGSASIFSE  VRYVKEPYIQ  SRFYRAPEIL  LGLPFCEKVD  VWSLGCVMAE
rathipk4_xp_  DFGSASIFSE  VRYVKEPYIQ  SRFYRAPEIL  LGLPFCEKVD  VWSLGCVMAE 201                                                       250
musdyrkla_np  MHTGEPLFSG  ANEVDQMNKI  VEVLGIPPAH  ILDQAPKARK  FFEKLPDGTW
ratdyrkla_np  MHTGEPLFSG  ANEVDQMNKI  VEVLGIPPAH  ILDQAPKARK  FFEKLPDGTW
humdyrkla_np  MHTGEPLFSG  ANEVDQMNKI  VEVLGIPPAH  ILDQAPKARK  FFEKLPDGTW
humdyrklb_np  MHTGEPLFSG  SNEVDQMNRI  VEVLGIPPAA  MLDQAPKARK  YFERLPGGGW
musdyrklb_np  MHTGEPLFSG  SNEVDQMSRI  VEVLGIPPAP  MLEQAPKARK  YFERLPGGGW
dmmnb_aaf487  MHTGEPLFSG  CNEVDQMNKI  VEVLGMPPKY  LLDQAHKTRK  FFDKIVADGS
wormt04c10_q  MHTGEPLFAG  SSEVDQMMKI  VEVLGMPPKE  MLDIGPKTHK  YFDKTEDGIY
dmsmi35a_q9v  LYTGFPLFPG  ENEVEQLACI  MEVLGLPPKV  LISVARRRRL  FFDSRDAPRC
humdyrk4_dyr  LYTGYPLFPG  ENEVEQLACI  MEVLGLPPAG  FIQTASRRQT  FFDSKGFPKN
humdyrk2_np_  LLTGYPLLPG  EDEGDQLACM  IELLGMPSQK  LLDASKRAKN  FVSSKGYPRY
humdyrk3_np_  LLTGQPLFPG  EDEGDQLACM  MELLGMPPPK  LLEQSKRAKY  FINSKGIPRY
wormf49e11_q  LLTGYPLLPG  EDENDQLALI  IELLGMPPPK  SLETAKRART  FITSKGYPRY
kab7_schpo.k  LFTGVPLFPG  GNETEQLGYI  MEVLGPPPMA  LIRNSTRSKA  YFDSEGKPHP
pom1_schpo.k  MYTGFPLFPG  ENEQEQLACI  MEIFGPPDHS  LIDKCSRKKV  FFDSSGKPRP
humhipk4.kd.  LHLGWPLYPG  NNEYDQVRYI  CETQGLPKPH  LLHAACKAHH  FFKRNPHPDA
monkeyhipk4_  LHLGWPLYPG  NNEYDQVRYI  CETQGLPKPH  LLHAARKAHH  FFKRNPHPDA
mushipk4.kd.  LHLGWPLYPG  NNEYDQVRYI  CETQGLPKPH  LLHAARKAHH  FFKRNPHPDA
rathipk4_xp_  LHLGWPLYPG  NNEYDQVRYI  CETQGLPKPH  LLHAARKAHH  FFKRNPHPDA
```

FIGURE 7 CONTINUED

```
                                                                       300
musdyrk1a_np   SLKKT..... ..........K DGKREYKPPG TRKLHNILGV ETGGPGGRRA
ratdyrk1a_np   SLKKT..... ..........K DGKREYKPPG TRKLHNILGV ETGGPGGRRA
humdyrk1a_np   NLKKT..... ..........K DGKREYKPPG TRKLHNILGV ETGGPGGRRA
humdyrk1b_np   TLRRT..... ..........K ELRKDYQGPG TRRLQEVLGV QTGGPGGRRA
musdyrk1b_np   TLRRT..... ..........K ELR....... .......... ..........
dmmnb_aaf487   YVLKK..... ..........N QNGRKYKPPG SRKLHDILGV ETGGPGGRRL
wormt04c10_q   YCKKTR.... ..........D GYRHTYKAPG ARKLHEILGV TSGGPGGRRL
dmsmi35a_q9v   ITNT...... .......... .......... ..........KG RKRSPGSKS.
humdyrk4_dyr   ITNN...... .......... .......... ..........RG KKRYPDSKD.
humdyrk2_np_   CTVTT..... .......... ....LSDGSV VLNGGRSRRG KLRGPPESRE
humdyrk3_np_   CSVTT..... .......... ....QADGRV VLVGGRSRRG KKRGPPGSKD
wormf49e11_q   CTATS..... .......... ....MPDGSV VLAGARSKRG KMRGPPASRS
kab7_schpo.k   ITDS...... .......... .......... .......... HNRLLVPSTR
pom1_schpo.k   FVSS...... .......... .......... .......... KGVSRRPFSK
humhipk4.kd.   ANPWQLKSSA DYLAETKVRP LERRKYMLKS LDQIETVNGG SVASRLTFPD
monkeyhipk4_   ANPWQLKSSA DYLAETKVRP LERRKYMLKS LDQIETVNGG SVASRLTFPD
mushipk4.kd.   TNPWQLKSSA DYLAETKVRP LERRKYMLKS LDQIETVNGG GAVSRLSFPD
rathipk4_xp_   TNPWQLKSSA DYLAETKVRP LERRKYMLKS LDQIETVNGG GAVNRLSFPD 301                                             340
musdyrk1a_np   GESGHTVADY LKFKDLILRM LDYDPKTRIQ PYYALQHSFF
ratdyrk1a_np   GESGHTVADY LKFKDLILRM LDYDPKTRIQ PYYALQHSFF
humdyrk1a_np   GESGHTVADY LKFKDLILRM LDYDPKTRIQ PYYALQHSFP
humdyrk1b_np   GEPGHSPADY LRFQDLVLRM LEYEPAARIS PLGALQHGFP
musdyrk1b_np   .......... ...KDLVLRM LEYEPAARIS PLGALQHGFP
dmmnb_aaf487   DEPGHSVSDY LKFKDLILRM LDFDPKTRVT PYYALQHNFF
wormt04c10_q   GEPGHSVEDY SKFKDLIKRM LQFDPKQRIS PYYVVRHPFL
dmsmi35a_q9v   .LAHILHCQD RYFIDFLQRC LEWDPAERMT PDEAAHHEFL
humdyrk4_dyr   .LTMVLKTYD TSFLDFLRRC LVWEPSLRMT PDQALKHAWI
humdyrk2_np_   WGNALKGCDD PLFLDFLKQC LEWDPAVRMT PGQALRHPWL
humdyrk3_np_   WGTALKGCDD YLFIEFLKRC LHWDPSARLT PAQALRHPWI
wormf49e11_q   WSTALKNMGD ELFVDFLKRC LDWDPETRMT PAQALKHKWL
kab7_schpo.k   TFSQLLNTKQ ASFLDFLSKC LKWDPKDRIT VDSALQHEFI
pom1_schpo.k   SLHQVLQCKD VSFLSFISDC LKWDPDERMT PQQAAQHDFL
humhipk4.kd.   REALAEHADL KSMVELIKRM LTWESHERIS PSAALRHPFV
monkeyhipk4_   REALAEHADL KSMVELIKRM LTWESHERIS PSAALRHPFV
mushipk4.kd.   REALAEHADL KSMVELIKRM LTWESHERIS PSAALRHPFV
rathipk4_xp_   REALAEHADL KSMVELIKRM LTWESHERIS PSAALRHPFV
```

METHODS OF MODULATING APOPTOSIS USING INHIBITORS OF BRAIN-LOCALIZED PROTEIN KINASES HOMOLOGOUS TO HOMEODOMAIN-INTERACTING PROTEIN KINASES

RELATED APPLICATIONS

This application is a division of application Ser. No. 10/808,522, filed on Mar. 25, 2004 which claims the benefit of U.S. Provisional Application Ser. No. 60/456,958, filed Mar. 25, 2003, and U.S. Provisional Application Ser. No. 60/491,251, filed Jul. 31, 2003, both of which are incorporated herein by reference in their entireties.

INCORPORATION OF SEQUENCE LISTING

The Sequence Listing filed on Oct. 28, 2009, created on Oct. 28, 2009, named 019970018001corr5to3ST25.txt, having a size in bytes of 164 kb, is hereby incorporated by reference in its entirety herein.

BACKGROUND OF THE INVENTION

Field of the Invention

The present invention is directed to novel proteins homologous to homeodomain-interacting protein kinases (HIPKs), as well as nucleic acid molecules encoding such novel proteins.

Kinases are signal transmission proteins that regulate many different cell processes (e.g., proliferation, differentiation, and signaling) by adding phosphate groups to proteins. Uncontrolled signaling has been implicated in a variety of disease conditions including inflammation, cancer, arteriosclerosis, and psoriasis. Reversible protein phosphorylation is one of the main strategies for controlling activities of eukaryotic cells. It is estimated that more than 1000 of the 10,000 proteins active in a typical mammalian cell are phosphorylated. The high-energy phosphate, which drives activation, is generally transferred from adenosine triphosphate (ATP) molecules to a particular protein by protein kinases and removed from that protein by protein phosphatases. Phosphorylation occurs in response to extracellular signals (e.g., hormones, neurotransmitters, growth and differentiation factors), cell cycle checkpoints, and environmental or nutritional stresses, and is roughly analogous to turning on a molecular switch. When the switch goes on, the appropriate protein kinase activates, e.g., a metabolic enzyme, regulatory protein, receptor, cytoskeletal protein, ion channel or pump, or transcription factor.

Malfunctions of cellular signaling have been associated with many diseases. Regulation of signal transduction by cytokines and association of signal molecules with protooncogenes and tumor suppressor genes have been the subjects of intense research. Many therapeutic strategies can now be developed through the synthesis of compounds that activate or inactivate protein kinases (Sridhar et al. (2000) *Pharm. Res.* 17:1345-53).

The importance of kinases in the etiology of diseases has been well established. Kinase proteins are a major target for drug action and development. In January 2002 there were more than 100 clinical trials involving the modulation of kinases ongoing in the USA (Dumas (2001) *Curr. Opin. Drug Discov. Devel.* 4-378-89; Levitzki and Gazit (1995) *Science* 267:1782-88). Trials are ongoing in a wide variety of therapeutic indications including asthma, Parkinson's disease, inflammation, psoriasis, rheumatoid arthritis, spinal cord injuries, muscle conditions, osteoporosis, graft-versus-host disease, cardiovascular disorders, autoimmune disorders, retinal detachment, stroke, epilepsy, ischemia/reperfusion, breast cancer, ovarian cancer, glioblastoma, non-Hodgkin's lymphoma, colorectal cancer, non-small cell lung cancer, brain cancer, Kaposi's sarcoma, pancreatic cancer, various solid tumors, liver cancer, and other tumors. Numerous kinds of modulators of kinase activity are currently in clinical trials, including antisense molecules, antibodies, small molecules, and gene therapy.

Accordingly, it is valuable to the field of pharmaceutical development to identify and characterize previously unknown members of the kinase family. The present invention advances the state of the art by providing previously unidentified human kinase proteins which are structurally related to homeodomain-interacting protein kinases (HIPKs). HIPKs (HIPK1, HIPK2, and HIPK3) were originally identified via a yeast two-hybrid screen and shown to be nuclear serine/threonine kinases that function as transcriptional corepressors for homeodomain transcription factors (Kim et al. (1998) *J. Biol. Chem.* 273:25875-79). Although HIPK1 was originally identified as a homeodomain-interacting protein, the primary activities of HIPK2 and HIPK3 appear to be in pathways of cell death or proliferation. For example, HIPK2 was recently shown to regulate the proapoptotic function of p53 (Hofmann et al. (2002) *Nature Cell Biol.* 4:1-10; D'Orazi et al. (2002) *Nature Cell Biol.* 4:11-19), while HIPK3 was shown to bind Fas and induce FADD phosphorylation, thereby promoting formation of a HIPK3/FADD/Fas complex (Rochat-Steiner et al. (2000) *J. Exp. Med.* 192:1165-74).

Many therapeutic strategies are aimed at critical components in signal transduction pathways. Approaches for regulating kinase gene expression include specific antisense oligonucleotides for inhibiting posttranscriptional processing of messenger RNA, naturally occurring products and their chemical derivatives to inhibit kinase activity, and monoclonal antibodies to inhibit receptor-linked kinases. In some cases, kinase inhibitors also allow other therapeutic agents additional time to become effective and act synergistically with current treatments (Sridhar et al., supra).

Among the areas of pharmaceutical research that are currently receiving a great deal of attention are the role of phosphorylation in transcriptional control, apoptosis, protein degradation, nuclear import and export, cytoskeletal regulation, and checkpoint signaling (Hunter (1998-99) *Harvey Lect.* 94:81-119). The accumulating knowledge about signaling networks and the proteins involved will be put to practical use in the development of potent and specific pharmacological modulators of phosphorylation-dependent signaling that can be used for therapeutic purposes. The rational structure-based design and development of highly specific kinase modulators is becoming routine, and drugs that intercede in signaling pathways are becoming a major class of drugs.

The kinases comprise one of the largest known protein groups, a superfamily of enzymes with widely varied functions and specificities. They are usually named after their substrate, their regulatory molecules, or some aspect of a mutant phenotype. With regard to substrates, the protein kinases may be roughly divided into two groups: those that phosphorylate serine or threonine residues (serine/threonine kinases; STKs), and those that phosphorylate tyrosine residues (protein tyrosine kinases; PTKs). A few protein kinases have dual specificity and phosphorylate threonine and tyrosine residues. Almost all kinases contain a similar 250-300 amino acid catalytic domain. The N-terminal domain, which contains subdomains I-IV, generally folds into a twolobed structure, which binds and orients the ATP (or GTP) donor molecule. The larger C-terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The two groups of kinases may be further categorized into families by the different amino acid sequences (generally between 5 and 100 residues) located on either side of, or inserted into loops of, the kinase domain. These added amino acid sequences allow for the regulation of each kinase as it recognizes and interacts with its target protein. The primary structure of the kinase domains is conserved and can be further subdivided into eleven (I-XI) subdomains. Each of these eleven subdomains contains specific residues and motifs or patterns of amino acids that are characteristic of that subdomain and are highly conserved (Hardie and Hanks (1995) *The Protein Kinase Facts Book*, Vol. I, pp. 7-20, Academic Press, San Diego, Calif.).

Serine/Threonine Kinases

The second messenger-dependent protein kinases primarily mediate the effects of second messengers such as cyclic AMP (cAMP), cyclic GMP, inositol triphosphate, phosphatidylinositol, 3,4,5-triphosphate, cyclic-ADP ribose, arachidonic acid, diacylglycerol and calcium-calmodulin. The cAMP-dependent protein kinases (PKA) are important members of the STK family. Cyclic AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cAMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, e.g., pp. 416-31, McGraw-Hill, New York, N.Y.).

Calcium-calmodulin (CaM)-dependent protein kinases (CaM kinases) are also members of the STK family. Calmodulin is a calcium receptor that mediates many calcium-regulated processes by binding to target proteins in response to the binding of calcium. The principle target protein in these processes is CaM kinase. CaM kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter-related proteins synapsin I and II, the gene transcription regulator, CREB, and the cystic fibrosis conductance regulator protein, CFTR (Haribabu et al. (1995) *EMBO J.* 14:3679-86). CaM kinase II also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or may be phosphorylated by another kinase as part of a kinase cascade.

Another ligand-activated protein kinase is 5'-AMP-activated protein kinase (AMPK) (Gao et al. (1996) *J. Biol. Chem.* 271:8675-81). Mammalian AMPK is a regulator of fatty acid and sterol synthesis through phosphorylation of the enzymes acetyl-CoA carboxylase and hydroxymethylglutaryl (HMG)-CoA reductase, and mediates responses of these pathways to cellular stresses such as heat shock and depletion of glucose and ATP. AMPK is a heterotrimeric complex comprised of a catalytic alpha subunit and two noncatalytic beta and gamma subunits that are believed to regulate the activity of the alpha subunit. Subunits of AMPK have a much wider distribution in nonlipogenic tissues (such as brain, heart, spleen, and lung) than expected. This distribution suggests that its role may extend beyond regulation of lipid metabolism alone.

The mitogen-activated protein kinases (MAP kinases) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan and Weinberg (1993) *Nature* 365:781-83). MAP kinase signaling pathways are present in mammalian cells as well as in yeast. The extracellular stimuli that activate mammalian pathways regulated by MAP kinases include epidermal growth factor (EGF), ultraviolet light, hyperosmolar medium, heat shock, endotoxic lipopolysaccharide (LPS), and proinflammatory cytokines such as tumor necrosis factor (TNF) and interleukin-1 (IL-1).

EGF receptor (EGFR) is found in over half of breast tumors unresponsive to hormone therapy. EGF is found in many tumors, and EGF may be required for tumor cell growth. Antibody to EGF was shown to block the growth of tumor xenografts in mice, while an antisense oligonucleotide for amphiregulin inhibited growth of a pancreatic cancer cell line.

Tamoxifen, a protein kinase C inhibitor with antiestrogen activity, is currently a standard treatment for hormone-dependent breast cancer. The use of this compound may increase the risk of developing cancer in other tissues such as the endometrium. Raloxifene, a related compound, has been shown to protect against osteoporosis. The tissue specificity of inhibitors must be considered when identifying therapeutic targets.

Cell proliferation and differentiation in normal cells are under the regulation and control of multiple MAP kinase cascades. Aberrant and deregulated functioning of MAP kinases can initiate and support carcinogenesis. Insulin and insulin-like growth factor-I (IGF-I) also activate a mitogenic MAP kinase pathway that may be important in acquired insulin resistance occurring in type 2 diabetes.

Many cancers become refractory to chemotherapy by developing a survival strategy involving the constitutive activation of the phosphatidylinositol-3 (PI-3) kinase-protein kinase B/Akt signaling cascade. This survival-signaling pathway thus becomes an important target for the development of specific inhibitors that would block its function. PI-3 kinase/Akt signaling is equally important in diabetes. The pathway activated by receptor tyrosine kinases (RTKs) subsequently regulates glycogen synthase 3, producing alterations in glycogen synthesis and glucose uptake. Since Akt has decreased activity in type 2 diabetes, it provides a therapeutic target.

Protein kinase inhibitors provide much of our knowledge about regulation and coordination of physiological functions. Endogenous peptide inhibitors occur in vivo. A pseudosubstrate sequence within PKC acts to inhibit the kinase in the absence of its lipid activator. A PKC inhibitor such as chelerythrine acts on the catalytic domain to block substrate interaction, while calphostin acts on the regulatory domain to mimic the pseudosubstrate sequence and block ATPase activity, or by inhibiting cofactor binding. The ability to inhibit specific PKC isozymes is limited.

Although some protein kinases have, to date, no known system of physiological regulation, many are activated or inactivated by autophosphorylation or phosphorylation by upstream protein kinases. The regulation of protein kinases also occurs transcriptionally, posttranscriptionally, and post-translationally. The mechanism of posttranscriptional regulation is alternative splicing of precursor mRNA. Protein kinase C-βI and -βII are two isoforms of a single PKC-β gene derived from differences in the splicing of the exon encoding the C-terminal 50-52 amino acids. Splicing can be regulated by a kinase cascade in response to peptide hormones such as insulin and IGF-I. PKC-βI and -βII have different specificities for phosphorylating members of the MAP kinase family, for glycogen synthase 3b, for nuclear transcription factors such as TLS/Fus, and for other nuclear kinases. By inhibiting the posttranscriptional alternative splicing of PKC-βII mRNA, PKC-PβII-dependent processes are inhibited.

The development of antisense oligonucleotides to inhibit the expression of various protein kinases has been successful. Antisense oligonucleotides are short lengths of synthetically manufactured, chemically modified DNA or RNA designed to specifically interact with mRNA transcripts encoding target proteins. The interaction of the antisense moiety with mRNA inhibits protein translation and, in some cases, post-transcriptional processing (e.g., alternative splicing and stability) of mRNA. Antisense oligonucleotides have been developed to alter alternative splicing of bcl-xlong to short mRNA forms and for inhibiting the translation of PKC-α and PKC-ζ.

Protein kinase C isoforms have been implicated in cellular changes observed in the vascular complications of diabetes. Hyperglycemia is associated with increased levels of PKC-α and -β isoforms in renal glomeruli of diabetic rats. Oral administration of a PKC-β inhibitor prevented the increased mRNA expression of TGF-β1 and extracellular matrix component genes. Administration of the specific PKC-β inhibitor (LY333531) also normalized levels of cytokines, caldesmon and hemodynamics of retinal and renal blood flow. Overexpression of the PKC-β isoform in the myocardium resulted in cardiac hypertrophy and failure. The use of LY333531 to prevent adverse effects of cardiac PKC-β overexpression in diabetic subjects is under investigation. The compound is also in Phase II/III clinical trials for diabetic retinopathy and diabetic macular edema indicating that it may be pharmacodynamically active.

PRK (proliferation-related kinase) is a serum/cytokine inducible STK that is involved in regulation of the cell cycle and cell proliferation in human megakaryocytic cells (Li et al. (1996) *J. Biol. Chem.* 271:19402-08). PRK is related to the polo family of STKs implicated in cell division. PRK is downregulated in lung tumor tissue and may be a protooncogene whose deregulated expression in normal tissue leads to oncogenic transformation. Altered PRK expression is implicated in a variety of disease conditions including cancer, inflammation, immune disorders, and disorders affecting growth and development.

DNA-dependent protein kinase (DNA-PK) is involved in the repair of double-strand breaks in mammalian cells. This enzyme requires ends of double-stranded DNA or transitions from single-stranded to double-stranded DNA in order to act as a serine/threonine kinase. Cells with defective or deficient DNA-PK activity are unable to repair radiation-induced DNA double-strand breaks and consequently are very sensitive to the lethal effects of ionizing radiation. Inhibition of DNA-PK has the potential to increase the efficacy of antitumor treatment with radiation or chemotherapeutic agents.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Cellular inhibitors of CDKs play a major role in cell-cycle progression. Alterations in the expression, function, and structure of cyclin and CDK are encountered in the cancer phenotype. Therefore CDKs may be important targets for new cancer therapeutic agents.

Often chemotherapy resistant cells tend to escape apoptosis. Under certain circumstances, inappropriate CDK activation may even promote apoptosis by encouraging the progression of the cell cycle under unfavorable conditions, e.g., attempting mitosis while DNA damage is largely unrepaired.

Purines and purine analogs act as CDK inhibitors. Flavopiridol (L86-8275) is a flavonoid that causes 50% growth inhibition of tumor cells at 25-160 nM (Kaur et al. (1992) *J. Natl. Cancer Inst.* 84:1736-40). It also inhibits EGFR and PKA ($IC_{50}$: approximately 100 μM). Flavopiridol induces apoptosis and inhibits lymphoid, myeloid, colon, and prostate cancer cells grown in vivo as tumor xenografts in nude mice.

Staurosporine and its derivative, UCN-01, in addition to inhibiting protein kinase C, inhibit cyclin B/CDK ($IC_{50}$: 3-6 nM). Staurosporine is toxic, but its derivative 7-hydroxystaurosporine (UCN-01) has antitumor properties and is in clinical trials. UCN-01 affects the phosphorylation of CDKs and alters the cell-cycle checkpoint functioning. These compounds illustrate that multiple intracellular targets may be affected as the concentration of an inhibitor is increased within cells.

Protein Tyrosine Kinases

Protein tyrosine kinases (PTKs) specifically phosphorylate tyrosine residues on their target proteins and may be divided into transmembrane, receptor PTKs (RTKs) and nontransmembrane, nonreceptor PTKs. Transmembrane protein tyrosine kinases are receptors for most growth factors. Binding of growth factor to the receptor activates the transfer of a phosphate group from ATP to selected tyrosine side chains of the receptor and other specific proteins. Growth factors (GFs) associated with receptor PTKs include epidermal GF (EGF), platelet-derived GF (PDGF), fibroblast GF (FGF), hepatocyte GF (HGF), insulin and insulin-like GFs (IGFs), nerve GF (NGF), vascular endothelial GF (VEGF), and macrophage colony stimulating factor (MCSF).

Because RTKs stimulate tumor cell proliferation, inhibitors of RTKs may inhibit the growth and proliferation of cancers by preventing tumor angiogenesis and can eliminate support from the host tissue by targeting RTKs located on vascular cells (e.g., blood vessel endothelial cells (VEGF receptor, or VEGFR) and stromal fibroblasts (FGF receptor)).

VEGF stimulates endothelial cell growth during angiogenesis, and increases the permeability of tumor vasculature so that proteins and other growth factors become accessible to the tumor. Broad-spectrum antitumor efficacy of an oral dosage form of an inhibitor of VEGF signaling has been reported. Thus, inhibition of VEGF receptor signaling presents an important therapeutic target. An extracellular receptor can also be a target for inhibition. For example, the EGF receptor family and its ligands are overexpressed and exist as an autocrine loop in many tumor types.

Increasing knowledge of the structure and activation mechanism of RTKs and the signaling pathways controlled by tyrosine kinases provided the possibility for the development of target-specific drugs and new anticancer therapies. Approaches towards the prevention or interception of deregulated RTK signaling include the development of selective components that target either the extracellular ligand-binding domain or the intracellular tyrosine kinase or substrate-binding region.

One of the most successful strategies for selectively killing tumor cells is the use of monoclonal antibodies (mAbs) that are directed against the extracellular domain of RTKs that are critically involved in cancer and are expressed at the surface of tumor cells. In recent years, recombinant antibody technology has made enormous progress in the design, selection and production of newly engineered antibodies, and it is possible to generate humanized antibodies, human-mouse chimeric or bispecific antibodies for targeted cancer therapy. Mechanistically, anti-RTK mAbs might work by blocking the ligand-receptor interaction and therefore inhibiting ligand-induced RTK signaling and increasing RTK downregulation and internalization. In addition, the binding of mAbs to certain epitopes on the cancer cells induces immune-mediated responses, such as opsonization and complement-mediated lysis, and triggers antibody-dependent cellular cytotoxicity (ADCC) by macrophages or natural killer cells. In recent years, it has become evident that mAbs control tumor growth by altering the intracellular-signaling pattern inside the targeted tumor cell, leading to growth inhibition and/or apoptosis. In contrast, bispecific antibodies can bridge selected surface molecules on a target cell with receptors on an effector cell triggering cytotoxic responses against the target cell. Despite the toxicity that has been seen in clinical trials of bispecific antibodies, advances in antibody engineering, characterization of tumor antigens, and immunology might help to predict rationally designed bispecific antibodies for anticancer therapy.

Another promising approach to inhibit aberrant RTK signaling are small molecule drugs that selectively interfere with the intrinsic tyrosine kinase activity and thereby block receptor autophosphorylation and activation of downstream signal transducers. The tyrphostins, which belong to the quinazolines, are one important group of such inhibitors that compete with ATP for the ATP binding site at the tyrosine kinase domain of the receptor; some members of the tyrphostins have been shown to specifically inhibit the EGFR. Potent and selective inhibitors of receptors involved in neovascularization have also been developed and are now undergoing clinical evaluation. Using the advantages of structure-based drug design, crystallographic structure information, combinatorial chemistry, and high-throughput screening, new structural classes of tyrosine kinase inhibitors (TKIs) with increased potency and selectivity, higher in vitro and in vivo efficacy, and decreased toxicity have emerged.

Recombinant immunotoxins provide another possibility of target-selective drug design. They are composed of a bacterial or plant toxin either fused or chemically conjugated to a specific ligand, such as the variable domains of the heavy and light chains of mAbs, or to a growth factor. For example, immunotoxins may contain the bacterial toxins *Pseudomonas* exotoxin A or diphtheria toxin, or the plant toxins ricin A or clavin. These recombinant molecules can selectively kill their target cells when internalized after binding to specific cell-surface receptors.

The use of antisense oligonucleotides represents another strategy to inhibit the activation of RTKs. Antisense oligonucleotides are short pieces of synthetic DNA or RNA that are designed to interact with the mRNA to block the transcription and thus the expression of specific proteins. These compounds interact with the mRNA by Watson-Crick base pairing and are therefore highly specific for the target protein. On the other hand, bioavailability may be poor since oligonucleotides can be degraded upon internalization by cellular endonucleases and exonucleases. Nevertheless, several preclinical and clinical studies suggest that antisense therapy might be therapeutically useful for the treatment of solid tumors.

A recent search of a public website cataloging clinical trials, many of which are actively recruiting patients, provided a list of over 100 clinical trials in response to the search term "kinase." A summary of some of the most successful drugs against receptor tyrosine kinase (RTK) signaling that are currently being evaluated in clinical phases or have already been approved by the FDA is shown in Table 1.

TABLE 1

| RTK | Drug | Company | Description | Status |
| --- | --- | --- | --- | --- |
| human epidermal growth factor receptor-2 (HER2) | trastuzumab (Herceptin ®) | Genentech | mAb directed against HER2 | Approved in 1998 |
| EGFR | gefitinib (Iressa ®; ZD1839) | AstraZeneca | TKI that inhibits EGFR signaling | Approved in 2003 |
| EGFR | cetuximab (Erbitux ®; C225) | ImClone | mAb directed against EGFR | Approved in 2004 |
| EGFR | erlotinib (Tarceva ®; OSI-774) | OSI Pharmaceuticals | TKI that inhibits EGFR signaling | Phase II/III |
| VEGFR2 | investigational oral drug (name not available) | Pfizer | TKI that inhibits VEGFR2 signaling | Phase I/II |
| VEGFR2 | ZD6474 | AstraZeneca | TKI that inhibits VEGFR2 signaling | Phase II |
| PDGFR | imatinib mesylate (Gleevec ®; STI571) | Novartis | TKI that inhibits PDGFR signaling (among several other actions) | Approved in 2001/ 2002 |

Therefore, the potential of RTKs and their relevant signaling as selective anticancer targets for therapeutic intervention has been recognized. As a consequence, a variety of successful target-specific drugs such as mAbs and RTK inhibitors have been developed and are currently being evaluated in clinical trials.

Nonreceptor PTKs lack transmembrane regions and instead form complexes with the intracellular regions of cell surface receptors. Such receptors that function through nonreceptor PTKs include those for cytokines, hormones (e.g., growth hormone and prolactin) and antigen-specific receptors on T and B lymphocytes.

Many of these PTKs were first identified as the products of mutant oncogenes in cancer cells where their activation was no longer subject to normal cellular controls. About one third of the known oncogenes encode PTKs, and it is well known that cellular transformation (oncogenesis) is often accompanied by increased tyrosine phosphorylation activity (Charbonneau and Tonks (1992) *Annu. Rev. Cell. Biol.*, 8:463-93).

Many tyrosine kinase inhibitors are derived from natural products including flavopiridol, genistein, erbstatin, lavendustin A, staurosporine, and UCN-01. Inhibitors directed at the ATP binding site are also available. Signals from RTKs can also be inhibited at other target sites, such as nuclear tyrosine kinases, membrane anchors (inhibition of farnesylation), and transcription factors.

Targeting the signaling potential of growth-promoting tyrosine kinases such as EGFR, HER2, PDGFR, src, and abl will block tumor growth, whereas blocking IGF-I and TRK will interfere with tumor cell survival. Inhibiting these kinases will lead to tumor shrinkage and apoptosis. Fkl-1/KDR and src are kinases necessary for neovascularization (angiogenesis) of tumors, and inhibition of these kinases will slow tumor growth, thereby decreasing metastases.

Inhibitors of RTKs stabilize the tumor in terms of cell proliferation, allowing normal cell loss via apoptosis, and prevent cell migration, invasion, and metastases. These drugs are likely to increase the time required for tumor progression, and may inhibit or attenuate the aggressiveness of the disease, but may not initially result in measurable tumor regression.

An example of cancer arising from a defective tyrosine kinase is a class of anaplastic lymphoma kinase (ALK)-positive lymphomas referred to as "ALKomas," which display inappropriate expression of a neural-specific tyrosine kinase.

Iressa® (gefitinib; ZD1839) is an orally active, selective EGFR inhibitor. This compound disrupts signaling involved in cancer cell proliferation, cell survival and tumor growth support by the host. Clinical trials with this agent demonstrated that it was clinically efficacious and well tolerated by patients. The compound has shown promising cytotoxicity towards several cancer cell lines. It recently has been approved by the FDA for advanced nonsmall-cell lung cancer.

Many growth factors and cytokines regulate cellular functions via the Janus kinase (JAK) signal transducers and activators of transcription (Stat). The JAK inhibitor tyrphostin AG490 prevents Stat3 activation and suppresses the growth of human prostate cancer cells.

Since the majority of protein kinases, both STKs and PTKs, are expressed in the brain, often in neuron-specific fashion, protein phosphorylation must play a key role in the development, maintenance, and function of the vertebrate central nervous system (Hunter (1998-99) *Harvey Lect.* 94:81-119). There is substantial evidence that many neurological disorders, such as Alzheimer's disease, Parkinson's disease, Huntington's disease, age-related neurodegeneration, depression, bipolar disorder, and obsessive-compulsive disorder, result from deficiencies in neurogenesis itself, or in the balance between neurogenesis and neurodegeneration (Duman et al. (1999) *Biol. Psychiatry* 46:1181-91; Jacobs et al. (2000) *Mol. Psychiatry* 5:262-69; Gage (2002) *J. Neurosci.* 22:612-13). Thus, neuron-specific kinases are well established as targets for the development of pharmacologically active modulators useful in the treatment of neurological diseases.

SUMMARY OF THE INVENTION

The invention provides isolated protein kinase polypeptides and the isolated nucleic acid molecules that encode them. The invention also provides genetically engineered expression vectors, host cells, and transgenic animals comprising the nucleic acid molecules of the invention. The invention additionally provides antisense and RNA interference (RNAi) molecules to the nucleic acid molecules of the invention. The invention further provides inhibitors, activators, and antibodies capable of binding to the protein kinase polypeptides of the invention, and provides uses for these inhibitors, activators, and antibodies in the prevention and treatment of neurological disorders.

BRIEF DESCRIPTION OF THE DRAWINGS

FIG. 1 shows preferred siRNA molecules targeted to human HIPK4 mRNA for use in RNAi. Target segments [SEQ ID NOs:18-34; 69-88; 129-143; and 174-179] of the HIPK4 transcripts are grouped according to their first two nucleotides (AA, CA, GA, or TA) and are shown in the 5'->3' orientation. "GC Ratio" refers to the percentage of total G+C nucleotides in each target segment; "Position" refers to the nucleotide position in the human HIPK4 cDNA (SEQ ID NO:1) immediately preceding the beginning of each target segment. Preferred siRNA molecules (siRNA duplexes) are shown on the right side of the figure. Both the sense strand [SEQ ID NOs:35-51; 89-108; 144-158; and 180-185] and the corresponding antisense strand [SEQ ID NOs:52-68; 109-128; 159-173; and 186-191] for each siRNA duplex are shown in the 5'->3' orientation. For example, the siRNA molecule directed to the first target segment presented in the figure (i.e., SEQ ID NO:18) is the siRNA duplex of the sense and antisense strands identified (i.e., SEQ ID NO:35 and SEQ ID NO:52, respectively).

FIGS. 2A, 2B, 2C, and 2D show the predicted amino acid sequences of human HIPK4 (SEQ ID NO:2), its predicted ATP binding domain, its predicted serine/threonine binding domain, and its predicted protein kinase domain, respectively.

FIGS. 3A, 3B, 3C, and 3D show the predicted amino acid sequences of mouse HIPK4 (SEQ ID NO:5), its predicted ATP binding domain, its predicted serine/threonine binding domain, and its predicted protein kinase domain, respectively.

FIGS. 4A, 4B, 4C, and 4D show the predicted amino acid sequences of monkey HIPK4 (SEQ ID NO:8), its predicted ATP binding domain, its predicted serine/threonine binding domain, and its predicted protein kinase domain, respectively.

FIGS. 5A, 5B, 5C, and 5D show the predicted amino acid sequences of rat HIPK4 (SEQ ID NO:17), its predicted ATP binding domain, its predicted serine/threonine binding domain, and its predicted protein kinase domain, respectively.

DETAILED DESCRIPTION OF THE INVENTION

Figure 6B:
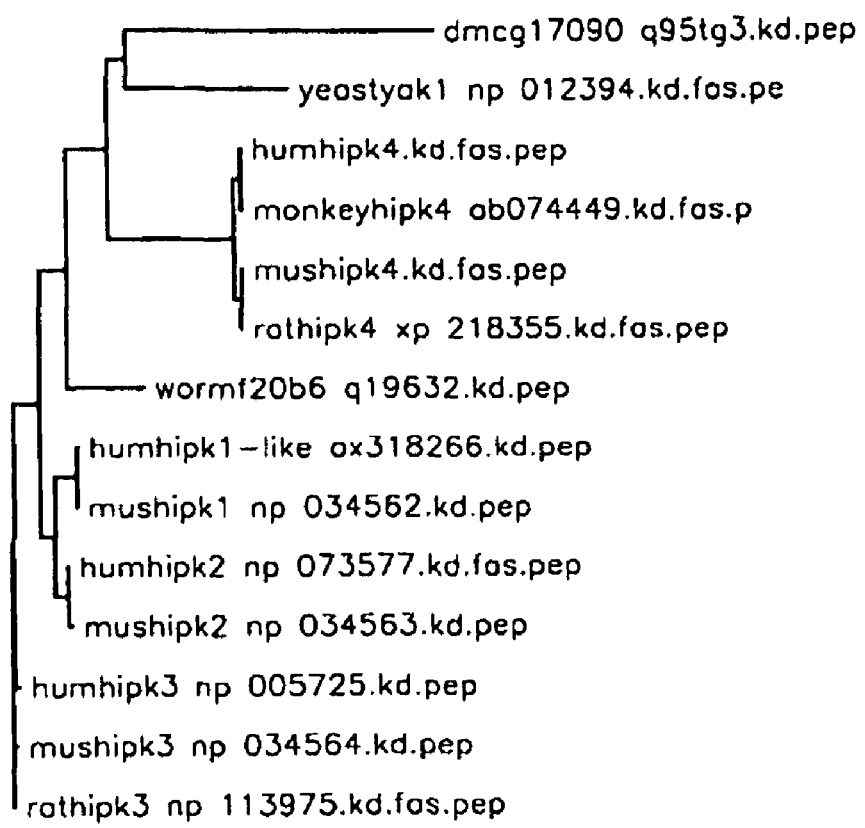
FIG. 6 shows a comparison of the amino acid sequences (FIG. 6A) of the conserved kinase catalytic domains of human HIPK4 (humHIPK4; from SEQ ID NO:2), mouse HIPK4 (musHIPK4; from SEQ ID NO:5), monkey HIPK4 (monkeyHIPK4; from SEQ ID NO:8), and rat HIPK4 (ratHIPK4; from SEQ ID NO:17) with the kinase catalytic domains of several known HIPKs (musHIPK3; ratHIPK3; humHIPK3; humHIPK1-like; musHIPK1; humHIPK2; musHIPK2; wormF20B6; yeastYAK1; and dmCG17090). A phylogenetic tree of the aligned sequences, including public accession codes/numbers, is presented in FIG. 6B.

The present invention provides novel isolated and purified polynucleotides and polypeptides homologous to the kinase catalytic domains of various known HIPKs.

For example, the invention provides purified and isolated polynucleotides encoding a novel protein kinase, herein designated "HIPK4." This protein kinase has an approximate molecular weight of 69 kD. Preferred DNA sequences of the invention include genomic and cDNA sequences and chemically synthesized DNA sequences.

The nucleotide sequence of a cDNA encoding this novel protein kinase, designated human HIPK4 cDNA, is set forth in SEQ ID NO:1. Polynucleotides of the present invention also include polynucleotides that hybridize under stringent conditions to SEQ ID NO:1, or its complement, and/or encode polypeptides that retain substantial biological activity of full-length human HIPK4. Polynucleotides of the present invention also include continuous portions of the sequence set forth in SEQ ID NO:1 comprising at least 21 consecutive nucleotides.

The deduced amino acid sequence of human HIPK4 is set forth in SEQ ID NO:2. Polypeptides of the present invention also include continuous portions of the sequence set forth in SEQ ID NO:2 comprising at least seven consecutive amino acids. A preferred polypeptide of the present invention includes any continuous portion of the sequence set forth in SEQ ID NO:2 that retains substantial biological activity (i.e., an active fragment) of full-length human HIPK4. Polynucleotides of the present invention also include, in addition to those polynucleotides of human origin described above, polynucleotides that encode the amino acid sequence set forth in SEQ ID NO:2 or a continuous portion thereof, and that differ from the polynucleotides of human origin described above only due to the well-known degeneracy of the genetic code.

The nucleotide sequence of a genomic DNA encoding this novel protein kinase, designated human HIPK4 genomic DNA, is set forth in SEQ ID NO:3. Polynucleotides of the present invention also include polynucleotides that hybridize under stringent conditions to SEQ ID NO:3, or its complement, and/or encode polypeptides that retain substantial biological activity of full-length human HIPK4. Polynucleotides of the present invention also include continuous portions of the sequence set forth in SEQ ID NO:3 comprising at least 21 consecutive nucleotides.

The nucleotide sequence of a cDNA encoding this novel protein kinase, designated mouse HIPK4 cDNA, is set forth in SEQ ID NO:4. Polynucleotides of the present invention also include polynucleotides that hybridize under stringent conditions to SEQ ID NO:4, or its complement, and/or encode polypeptides that retain substantial biological activity of full-length mouse HIPK4. Polynucleotides of the present invention also include continuous portions of the sequence set forth in SEQ ID NO:4 comprising at least 21 consecutive nucleotides.

The deduced amino acid sequence of mouse HIPK4 is set forth in SEQ ID NO:5. Polypeptides of the present invention also include continuous portions of the sequence set forth in SEQ ID NO:5 comprising at least seven consecutive amino acids. A preferred polypeptide of the present invention includes any continuous portion of the sequence set forth in SEQ ID NO:5 that retains substantial biological activity (i.e., an active fragment) of full-length mouse HIPK4. Polynucleotides of the present invention also include, in addition to those polynucleotides of mouse origin described above, polynucleotides that encode the amino acid sequence set forth in SEQ ID NO:5 or a continuous portion thereof, and that differ from the polynucleotides of mouse origin described above only due to the well-known degeneracy of the genetic code.

The nucleotide sequence of a genomic DNA encoding this novel protein kinase, designated mouse HIPK4 genomic DNA, is set forth in SEQ ID NO:6. Polynucleotides of the present invention also include polynucleotides that hybridize under stringent conditions to SEQ ID NO:6, or its complement, and/or encode polypeptides that retain substantial biological activity of full-length mouse HIPK4. Polynucleotides of the present invention also include continuous portions of the sequence set forth in SEQ ID NO:6 comprising at least 21 consecutive nucleotides.

The nucleotide sequence of a cDNA encoding this novel protein kinase, designated monkey HIPK4 cDNA, is set forth in SEQ ID NO:7. Polynucleotides of the present invention also include polynucleotides that hybridize under stringent conditions to SEQ ID NO:7, or its complement, and/or encode polypeptides that retain substantial biological activity of full-length monkey HIPK4. Polynucleotides of the present invention also include continuous portions of the sequence set forth in SEQ ID NO:7 comprising at least 21 consecutive nucleotides.

The deduced amino acid sequence of monkey HIPK4 is set forth in SEQ ID NO:8. Polypeptides of the present invention also include continuous portions of the sequence set forth in SEQ ID NO:8 comprising at least seven consecutive amino acids. A preferred polypeptide of the present invention includes any continuous portion of the sequence set forth in SEQ ID NO:8 that retains substantial biological activity (i.e., an active fragment) of full-length monkey HIPK4. Polynucleotides of the present invention also include, in addition to those polynucleotides of monkey origin described above, polynucleotides that encode the F amino acid sequence set forth in SEQ ID NO:8 or a continuous portion thereof, and that differ from the polynucleotides of monkey origin described above only due to the well-known degeneracy of the genetic code.

The nucleotide sequence of a cDNA encoding this novel protein kinase, designated rat HIPK4 cDNA, is set forth in SEQ ID NO:16. Polynucleotides of the present invention also include polynucleotides that hybridize under stringent conditions to SEQ ID NO:16, or its complement, and/or encode polypeptides that retain substantial biological activity of full-length rat HIPK4. Polynucleotides of the present invention also include continuous portions of the sequence set forth in SEQ ID NO:16 comprising at least 21 consecutive nucleotides.

The deduced amino acid sequence of rat HIPK4 is set forth in SEQ ID NO:17. Polypeptides of the present invention also include continuous portions of the sequence set forth in SEQ ID NO:17 comprising at least seven consecutive amino acids. A preferred polypeptide of the present invention includes any continuous portion of the sequence set forth in SEQ ID NO:17 that retains substantial biological activity (i.e., an active fragment) of full-length rat HIPK4. Polynucleotides of the present invention also include, in addition to those polynucleotides of rat origin described above, polynucleotides that encode the amino acid sequence set forth in SEQ ID NO:17 or a continuous portion thereof, and that differ from the polynucleotides of rat origin described above only due to the well-known degeneracy of the genetic code.

The isolated polynucleotides of the present invention may be used as hybridization probes and primers to identify and isolate nucleic acids having sequences identical to, or similar to, those encoding the disclosed polynucleotides. Hybridization methods for identifying and isolated nucleic acids include polymerase chain reaction (PCR), Southern hybridization, and Northern hybridization, and are well known to those skilled in the art.

Hybridization reactions can be performed under conditions of different stringencies. The stringency of a hybridization reaction includes the difficulty with which any two nucleic acid molecules will hybridize to one another. Preferably, each hybridizing polynucleotide hybridizes to its corresponding polynucleotide under reduced stringency conditions, more preferably stringent conditions, and most preferably highly stringent conditions. Examples of stringency conditions are shown in Table 2 below: highly stringent conditions are those that are at least as stringent as, for example, conditions A-F; stringent conditions are at least as stringent as, for example, conditions G-L; and reduced stringency conditions are at least as stringent as, for example, conditions M-R.

TABLE 2

| Stringency Condition | Polynucleotide Hybrid | Hybrid Length (bp)[1] | Hybridization Temperature and Buffer[2] | Wash Temperature and Buffer[2] |
| --- | --- | --- | --- | --- |
| A | DNA:DNA | >50 | 65° C.; 1 × SSC -or- 42° C.; 1 × SSC, 50% formamide | 65° C.; 0.3 × SSC |
| B | DNA:DNA | <50 | $T_B$*; 1 × SSC | $T_B$*; 1 × SSC |
| C | DNA:RNA | >50 | 67° C.; 1 × SSC -or- 45° C.; 1 × SSC, 50% formamide | 67° C.; 0.3 × SSC |
| D | DNA:RNA | <50 | $T_D$*; 1 × SSC | $T_D$*; 1 × SSC |
| E | RNA:RNA | >50 | 70° C.; 1 × SSC -or- 50° C.; 1 × SSC, 50% formamide | 70° C.; 0.3 × SSC |
| F | RNA:RNA | <50 | $T_F$*; 1 × SSC | $T_F$; 1 × SSC |
| G | DNA:DNA | >50 | 65° C.; 4 × SSC -or- 42° C.; 4 × SSC, 50% formamide | 65° C.; 1 × SSC |
| H | DNA:DNA | <50 | $T_H$*; 4 × SSC | $T_H$*; 4 × SSC |
| I | DNA:RNA | >50 | 67° C.; 4 × SSC -or- 45° C.; 4 × SSC, 50% formamide | 67° C.; 1 × SSC |
| J | DNA:RNA | <50 | $T_J$*; 4 × SSC | $T_J$*; 4 × SSC |
| K | RNA:RNA | >50 | 70° C.; 4 × SSC -or- 50° C.; 4 × SSC, 50% formamide | 67° C.; 1 × SSC |
| L | RNA:RNA | <50 | $T_L$*; 2 × SSC | $T_L$*; 2 × SSC |
| M | DNA:DNA | >50 | 50° C.; 4 × SSC -or- 40° C.; 6 × SSC, 50% formamide | 50° C.; 2 × SSC |
| N | DNA:DNA | <50 | $T_N$*; 6 × SSC | $T_N$*; 6 × SSC |
| O | DNA:RNA | >50 | 55° C.; 4 × SSC -or- 42° C.; 6 × SSC, 50% formamide | 55° C.; 2 × SSC |
| P | DNA:RNA | <50 | $T_P$*; 6 × SSC | $T_P$*; 6 × SSC |

TABLE 2-continued

| Stringency Condition | Poly-nucleotide Hybrid | Hybrid Length (bp)[1] | Hybridization Temperature and Buffer[2] | Wash Temperature and Buffer[2] |
|---|---|---|---|---|
| Q | RNA:RNA | >50 | 60° C.; 4 × SSC -or- 45° C.; 6 × SSC, 50% formamide | 60° C.; 2 × SSC |
| R | RNA:RNA | <50 | $T_R^*$; 4 × SSC | $T_R^*$; 4 × SSC |

[1]The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.
[2]SSPE (1 × SSPE is 0.15 M NaCl, 10 mM NaH$_2$PO$_4$, and 1.25 mM EDTA, pH 7.4) can be substituted for SSC (1 × SSC is 0.15 M NaCl and 15 mM sodium citrate) in the hybridization and wash buffers; washes are performed for 15 minutes after hybridization is complete.
$T_B^*$-$T_R^*$: The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6(log$_{10}$Na$^+$) + 0.41(% G + C) − (600/N), where N is the number of bases in the hybrid, and Na$^+$ is the concentration of sodium ions in the hybridization buffer (Na$^+$ for 1 × SSC = 0.165 M).
Additional examples of stringency conditions for polynucleotide hybridization are provided in Sambrook et al. (1989) Molecular Cloning: A Laboratory Manual, Chs. 9 & 11, Cold Spring Harbor Laboratory Press, Cold Spring Harbor, NY, and Ausubel et al., eds. (1995) Current Protocols in Molecular Biology, Sects. 2.10 & 6.3-6.4, John Wiley & Sons, Inc., herein incorporated by reference.

The isolated polynucleotides of the present invention may be used as hybridization probes and primers to identify and isolate DNAs having sequences encoding allelic variants of the disclosed polynucleotides. Allelic variants are naturally occurring alternative forms of the disclosed polynucleotides that encode polypeptides that are identical to or have significant similarity to the polypeptides encoded by the disclosed polynucleotides. Preferably, allelic variants have at least 90% sequence identity (more preferably, at least 95% identity; most preferably, at least 99% identity) with the disclosed polynucleotides. In one embodiment of the invention, an isolated nucleic acid molecule comprising a sequence at least 96.3% identical to SEQ ID NO:1 is provided.

The isolated polynucleotides of the present invention may also be used as hybridization probes and primers to identify and isolate DNAs having sequences encoding polypeptides homologous to the disclosed polynucleotides. These homologs are polynucleotides and polypeptides isolated from different species than those of the disclosed polypeptides and polynucleotides, or within the same species, but with significant sequence similarity to the disclosed polynucleotides and polypeptides. Preferably, polynucleotide homologs have at least 60% sequence identity (more preferably, at least 75% identity; most preferably, at least 90% identity) with the disclosed polynucleotides, whereas polypeptide homologs have at least 30% sequence identity (more preferably, at least 45% identity; most preferably, at least 60% identity) with the disclosed polypeptides. Preferably, homologs of the disclosed polynucleotides and polypeptides are those isolated from mammalian species. In one embodiment of the invention, an isolated nucleic acid molecule comprising a sequence at least 96.3% identical to SEQ ID NO:1 is provided. In another embodiment of the invention, a purified polypeptide, the amino acid sequence of which comprises a sequence at least 97.2% identical to SEQ ID NO:2, is provided.

The isolated polynucleotides of the present invention may also be used as hybridization probes and primers to identify cells and tissues that express the polypeptides of the present invention and the conditions under which they are expressed.

Additionally, the isolated polynucleotides of the present invention may be used to alter (i.e., enhance, reduce, or modify) the expression of the genes corresponding to the polynucleotides of the present invention in an organism.

These "corresponding genes" are the genomic DNA sequences of the present invention (e.g., SEQ ID NO:3 or SEQ ID NO:6) that are transcribed to produce the mRNAs from which the cDNA polynucleotides of the present invention (e.g., SEQ ID NO:1 or SEQ ID NO:4) are derived.

Altered expression of the genes of the present invention in a cell or organism may be achieved through the use of various inhibitory polynucleotides, such as antisense polynucleotides and ribozymes that bind and/or cleave the mRNA transcribed from the genes of the invention (e.g., Galderisi et al. (1999) *J. Cell Physiol.* 181:251-57; Sioud (2001) *Curr. Mol. Med.* 1:575-88).

The antisense polynucleotides or ribozymes of the invention can be complementary to an entire coding strand of a gene of the invention, or to only a portion thereof. Alternatively, antisense polynucleotides or ribozymes can be complementary to a noncoding region of the coding strand of a gene of the invention. The antisense polynucleotides or ribozymes can be constructed using chemical synthesis and enzymatic ligation reactions using procedures well known in the art. The nucleoside linkages of chemically synthesized polynucleotides can be modified to enhance their ability to resist nuclease-mediated degradation, as well as to increase their sequence specificity. Such linkage modifications include, but are not limited to, phosphorothioate, methylphosphonate, phosphoroamidate, boranophosphate, morpholino, and peptide nucleic acid (PNA) linkages (Galderisi et al., supra; Heasman (2002) *Dev. Biol.* 243:209-14; Micklefield (2001) *Curr. Med. Chem.* 8:1157-79). Alternatively, these molecules can be produced biologically using an expression vector into which a polynucleotide of the present invention has been subcloned in an antisense (i.e., reverse) orientation.

The inhibitory polynucleotides of the present invention also include triplex-forming oligonucleotides (TFOs) which bind in the major groove of duplex DNA with high specificity and affinity (Knauert and Glazer (2001) *Hum. Mol. Genet.* 10:2243-51). Expression of the genes of the present invention can be inhibited by targeting TFOs complementary to the regulatory regions of the genes (i.e., the promoter and/or enhancer sequences) to form triple helical structures that prevent transcription of the genes.

In a preferred embodiment, the inhibitory polynucleotide of the present invention is a short interfering RNA (siRNA).

siRNAs are short (preferably 19-25 nucleotides; most preferably 19 or 21 nucleotides), double-stranded RNA molecules that cause sequence-specific degradation of target mRNA. This degradation is known as RNA interference (RNAi) (e.g., Bass (2001) *Nature* 411:428-29). Originally identified in lower organisms, RNAi has been effectively applied to mammalian cells and has recently been shown to prevent fulminant hepatitis in mice treated with siRNAs targeted to Fas mRNA (Song et al. (2003) *Nature Med.* 9:347-51).

The siRNA molecules of the present invention can be generated by annealing two complementary single-stranded RNA molecules together (one of which matches a portion of the target mRNA) (Fire et al., U.S. Pat. No. 6,506,559) or through the use of a single hairpin RNA molecule which folds back on itself to produce the requisite double-stranded portion (Yu et al. (2002) *Proc. Natl. Acad. Sci. USA* 99:6047-52). The siRNA molecules can be chemically synthesized (Elbashir et al. (2001) *Nature* 411:494-98) or produced by in vitro transcription using single-stranded DNA templates (Yu et al., supra). Alternatively, the siRNA molecules can be produced biologically, either transiently (Yu et al., supra; Sui et al. (2002) *Proc. Natl. Acad. Sci. USA* 99:5515-20) or stably (Paddison et al. (2002) *Proc. Natl. Acad. Sci. USA* 99:1443-48), using an expression vector(s) containing the sense and antisense siRNA sequences. Recently, reduction of levels of target mRNA in primary human cells, in an efficient and sequence-specific manner, was demonstrated using adenoviral vectors that express hairpin RNAs, which are further processed into siRNAs (Arts et al. (2003) *Genome Res.* 13:2325-32).

The siRNA molecules targeted to the polynucleotides of the present invention can be designed based on criteria well known in the art (e.g., Elbashir et al. (2001) *EMBO J.* 20:6877-88). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; and the target segment preferably should be in the ORF region of the target mRNA and preferably should be at least 75 bp after the initiation ATG and at least 75 bp before the stop codon. Based on these criteria, preferred siRNA molecules of the present invention have been designed and are shown in FIG. 1. Other siRNA molecules targeted to the polynucleotides of the present invention can be designed by one of ordinary skill in the art using the aforementioned criteria or other known criteria (e.g., Reynolds et al. (2004) *Nature Biotechnol.* 22:326-30).

Altered expression of the genes of the present invention in a cell or organism may also be achieved through the creation of nonhuman transgenic animals into whose genomes polynucleotides of the present invention have been introduced. Such transgenic animals include animals that have multiple copies of a gene (i.e., the transgene) of the present invention. A tissue-specific regulatory sequence(s) may be operably linked to the transgene to direct expression of a polypeptide of the present invention to particular cells or a particular developmental stage. Methods for generating transgenic animals via embryo manipulation and microinjection, particularly animals such as mice, have become conventional and are well known in the art (e.g., Bockamp et al. (2002) *Physiol. Genomics* 11:115-32).

Altered expression of the genes of the present invention in an organism may also be achieved through the creation of animals whose endogenous genes corresponding to the polynucleotides of the present invention have been disrupted through insertion of extraneous polynucleotide sequences (i.e., a knockout animal). The coding region of the endogenous gene may be disrupted, thereby generating a nonfunctional protein. Alternatively, the upstream regulatory region of the endogenous gene may be disrupted, resulting in the altered expression of the still-functional protein. Methods for generating knockout animals include homologous recombination and are well known in the art (e.g., Wolfer et al. (2002) *Trends Neurosci.* 25:336-40).

The isolated polynucleotides of the present invention may be operably linked to an expression control sequence such as the pMT2 and pED expression vectors for recombinant production of the polypeptides of the present invention. General methods of expressing recombinant proteins are well known in the art.

A number of cell types may act as suitable host cells for recombinant expression of the polypeptides of the present invention. Mammalian host cells include, e.g., COS cells, CHO cells, 293 cells, A431 cells, 3T3 cells, CV-1 cells, HeLa cells, L cells, BHK21 cells, HL-60 cells, U937 cells, HaK cells, Jurkat cells, normal diploid cells, cell strains derived from in vitro culture of primary tissue, and primary explants.

Alternatively, it may be possible to recombinantly produce the polypeptides of the present invention in lower eukaryotes such as yeast or in prokaryotes. Potentially suitable yeast strains include *Saccharomyces cerevisiae*, *Schizosaccharomyces pombe*, *Kluyveromyces* strains, and *Candida* strains. Potentially suitable bacterial strains include *Escherichia coli*, *Bacillus subtilis*, and *Salmonella typhimurium*. If the polypeptides of the present invention are made in yeast or bacteria, it may be necessary to modify them by, e.g., phosphorylation or glycosylation of appropriate sites, in order to obtain functionality. Such covalent attachments may be accomplished using well-known chemical or enzymatic methods.

The polypeptides of the present invention may also be recombinantly produced by operably linking the isolated polynucleotides of the present invention to suitable control sequences in one or more insect expression vectors, such as baculovirus vectors, and employing an insect cell expression system. Materials and methods for baculovirus/Sf9 expression systems are commercially available in kit form (e.g., the MaxBac® kit, Invitrogen, Carlsbad, Calif.).

Following recombinant expression in the appropriate host cells, the polypeptides of the present invention may then be purified from culture medium or cell extracts using known purification processes, such as gel filtration and ion exchange chromatography. Purification may also include affinity chromatography with agents known to bind the polypeptides of the present invention. These purification processes may also be used to purify the polypeptides of the present invention from natural sources.

Alternatively, the polypeptides of the present invention may also be recombinantly expressed in a form that facilitates purification. For example, the polypeptides may be expressed as fusions with proteins such as maltose-binding protein (MBP), glutathione-S-transferase (GST), or thioredoxin (TRX). Kits for expression and purification of such fusion proteins are commercially available from New England BioLabs (Beverly, Mass.), Pharmacia (Piscataway, N.J.), and Invitrogen (Carlsbad, Calif.), respectively. The polypeptides of the present invention can also be tagged with a small epitope and subsequently identified or purified using a specific antibody to the epitope. A preferred epitope is the FLAG epitope, which is commercially available from Eastman Kodak (New Haven, Conn.).

The polypeptides of the present invention may also be produced by known conventional chemical synthesis. Methods for chemically synthesizing the polypeptides of the present invention are well known to those skilled in the art. Such chemically synthetic polypeptides may possess biological properties in common with the natural, purified polypeptides, and thus may be employed as biologically active or immunological substitutes for the natural polypeptides.

The polypeptides of the present invention also encompass molecules that are structurally different from the disclosed polypeptides (e.g., which have a slightly altered sequence), but which have substantially the same biochemical properties as the disclosed polypeptides (e.g., are changed only in functionally nonessential amino acid residues). Such molecules include naturally occurring allelic variants and deliberately engineered variants containing alterations, substitutions, replacements, insertions, or deletions. Techniques and kits for such alterations, substitutions, replacements, insertions, or deletions are well known to those skilled in the art.

Antibody molecules to the polypeptides of the present invention may be produced by methods well known to those skilled in the art. For example, monoclonal antibodies can be produced by generation of hybridomas in accordance with known methods. Hybridomas formed in this manner are then screened using standard methods, such as enzyme-linked immunosorbent assay (ELISA), to identify one or more hybridomas that produce an antibody that specifically binds with the polypeptides of the present invention.

A full-length polypeptide of the present invention may be used as the immunogen, or, alternatively, antigenic peptide fragments of the polypeptides may be used. An antigenic peptide of a polypeptide of the present invention comprises at least seven continuous amino acid residues and encompasses an epitope such that an antibody raised against the peptide forms a specific immune complex with the polypeptide. Preferably, the antigenic peptide comprises at least 10 amino acid residues, more preferably at least 15 amino acid residues, even more preferably at least 20 amino acid residues, and most preferably at least 30 amino acid residues.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody display libraries can be found in the literature.

Polyclonal sera and antibodies may be produced by immunizing a suitable subject with a polypeptide of the present invention. The antibody titer in the immunized subject may be monitored over time by standard techniques, such as with ELISA using immobilized marker protein. If desired, the antibody molecules directed against a polypeptide of the present invention may be isolated from the subject or culture media and further purified by well known techniques, such as protein A chromatography, to obtain an IgG fraction.

Fragments of antibodies to the polypeptides of the present invention may be produced by cleavage of the antibodies in accordance with methods well known in the art. For example, immunologically active F(ab') and F(ab')$_2$ fragments may be generated by treating the antibodies with an enzyme such as pepsin.

Additionally, chimeric, humanized, and single-chain antibodies to the polypeptides of the present invention, comprising both human and nonhuman portions, may be produced using standard recombinant DNA techniques. Humanized antibodies may also be produced using transgenic mice that are incapable of expressing endogenous immunoglobulin heavy and light chain genes, but that can express human heavy and light chain genes.

The polynucleotides and polypeptides of the present invention may also be used in screening assays to identify pharmacological agents or lead compounds for agents capable of modulating HIPK4 activity, either substrate binding and/or kinase activity. Such screening assays are well known in the art (e.g., Turek et al. (2001) *Anal. Biochem.* 299:45-53). For example, samples containing HIPK4 (either natural or recombinant) can be contacted with one of a plurality of test compounds (either small organic molecules or biological agents), and the activity of HIPK4 in each of the treated samples can be compared to the activity of HIPK4 in untreated samples or in samples contacted with different test compounds to determine whether any of the test compounds provides: (1) a substantially decreased level of HIPK4 activity, thereby indicating an inhibitor of HIPK4 activity, or (2) a substantially increased level of HIPK4 activity, thereby indicating an activator of HIPK4 activity. In a preferred embodiment, the identification of test compounds capable of modulating HIPK4 activity is performed using high-throughput screening assays, such as provided by BIACORE® (Biacore International AB, Uppsala, Sweden), BRET (bioluminescence resonance energy transfer), and FRET (fluorescence resonance energy transfer) assays, as well as ELISA.

The present invention is illustrated by the following examples related to human, mouse, monkey and rat cDNAs, designated human HIPK4 cDNA, mouse HIPK4 cDNA, monkey HIPK4 cDNA, and rat HIPK4 cDNA, respectively, encoding novel protein kinase polypeptides designated HIPK4.

EXAMPLES

The Examples which follow are set forth to aid in the understanding of the invention but are not intended to, and should not be construed to, limit its scope in any way. The Examples do not include detailed descriptions of conventional methods, such as those employed in the construction of vectors and plasmids, the insertion of genes encoding polypeptides into such vectors and plasmids, the introduction of such vectors and plasmids into host cells, or the expression of polypeptides from such vectors and plasmids in host cells. Such methods are well known to those of ordinary skill in the art and are described in numerous publications.

Example 1

Identification of HIPK4 DNA Sequences

Example 1.1

Identification of Human HIPK4 Genomic and cDNA Sequences

Human HIPK4 was initially predicted by structural-based genome data mining using novel computational techniques based on bioinformatics principles described in Baxevanis and Guellette, eds., *Bioinformatics: A Practical Guide to the Analysis of Genes and Proteins*, Wiley InterScience, New York (2001), herein incorporated by reference in its entirety.

Briefly, X-ray crystal structures of the catalytic domains of known mammalian and yeast serine/threonine and tyrosine protein kinases were collected from the SCOP database (scop.berkeley.edu) and aligned according to their structural identities/similarities using the ProCeryon package (www.proceryon.com). This alignment was converted into a "scoring matrix" which carries the structural profile of the kinase catalytic domains. DNA sequences encoding the predicted protein sequences aligning to the scoring matrix were extracted from public human genomic sequence databases, such as Celera and GenBank. The extracted nucleic acid sequences were clustered to eliminate repetitive entries. The putative kinase domains were then sequentially run through a series of queries and filters to identify novel protein kinase sequences. Specifically, the identified sequences were used to search a nucleotide and amino acid repository of known human protein kinases using BLASTN and BLASTX. The output was parsed into a spreadsheet to facilitate elimination of known genes by manual inspection. The selected hits were then queried using BLASTN against the NCBI nr and est databases to confirm their novelty and also to select the closest homologs.

Extensions of the partial DNA sequences were performed using the Genewise program to predict potential open reading frames based on homology to the closest homologs. Genewise requires two input sequences: the homologous protein and the genomic DNA containing the gene of interest. The homologs were identified by BLASTP searches of the NCBI nr protein database with the novel kinase hits described above. The genomic DNA was identified by BLASTN searches of the Celera and GenBank databases. The extended "virtual" cDNA sequences were then used to isolate the corresponding physical clones from cDNA libraries.

One such virtual cDNA sequence identified was homologous to known HIPKs of different species. This virtual cDNA sequence was used to isolate a physical clone with an open reading frame of 1848 bp (coding sequence of 1851 bp) from a human full-length testis library using GeneTrapper technology (Invitrogen, Carlsbad, Calif.). This novel HIPK-like clone was termed human HIPK4. The human HIPK4 cDNA sequence, and its deduced amino acid sequence, are set forth in SEQ ID NOs: 1 and 2, respectively. Based on known kinases, the 616 amino acid human HIPK4 polypeptide (FIG. 2A) is predicted to have an ATP binding domain ranging from amino acids 17-40 (FIG. 2B), a serine/threonine binding domain ranging from amino acids 132-144 (FIG. 2C), and a protein kinase domain ranging from amino acids 11-347 (FIG. 2D).

In additional experiments, isolation and sequencing of clones from a human fetal brain cDNA library corresponding to this HIPK-like sequence also revealed an open reading frame of 1848 bp (coding sequence of 1851 bp); in some clones, the sequence was identical to that isolated from the testis library, whereas in other clones a polymorphism was identified (G at position 905 changed to A, resulting in arginine at position 302 changed to glutamine). In brief detail, primer oligonucleotides were synthesized (based on virtual cDNA sequence) and used in a PCR with human fetal brain cDNA as template. The human fetal brain cDNA library was utilized per manufacturer's instructions (Clontech, Palo Alto, Calif.). The sequences of the forward (SEQ ID NO:9) and reverse (SEQ ID NO:10) primers for PCR were:

```
5' AACCGCATCATCAAGAACGAG 3'    (forward primer)

5' GTCAGGGAAGGTTAGCCGACT 3'    (reverse primer).
```

A product of the expected size was isolated, and the DNA sequence was determined and found to be identical to the predicted sequence for that region. Additional primer oligonucleotides were synthesized and used in RACE (rapid amplification of cDNA ends) reactions in an attempt to identify the remaining portions of the cDNA. The forward (sense) primer was used in RACE reactions to identify the 3' end of the sequence; the reverse (antisense) primer was used to identify the 5' end. The sequences of the forward (SEQ ID NO:11) and reverse (SEQ ID NO:12) primers for the RACE reactions were:

```
5' AGACGAAGGTGCGCCCATTGGAG 3'    (forward primer)

5' CTGGCGGATCCGAAGTCAATCAC 3'    (reverse primer).
```

Comparison of the human HIPK4 cDNA sequences with the genomic DNA used for the GeneWise extension described above revealed that the human HIPK4 locus, which maps to human chromosome 19q13.1 (position numbers 38656144-38668459, according to Celera mapping), contains 4 exons and 3 introns, with 5' and 3' regions flanking the start and stop codons, respectively (see Table 3, below). The human HIPK4 genomic DNA sequence is set forth in SEQ ID NO:3.

TABLE 3

| Region in SEQ ID NO: 3 | Sequence Attribute | Length (nt) | Position in SEQ ID NO: 1 |
|---|---|---|---|
| 1-2000 | 5'-sequence[1] | 2000 | — |
| 2001-2465 | Exon 1 | 465 | 1-465 |
| 2466-7762 | Intron 1 | 5297 | — |
| 7763-8119 | Exon 2 | 357 | 466-822 |
| 8120-10734 | Intron 2 | 2615 | — |
| 10735-11580 | Exon 3 | 846 | 823-1668 |
| 11581-12133 | Intron 3 | 553 | — |
| 12134-12313 | Exon 4 | 180 | 1669-1848 |
| 12314-12316 | Stop | 3 | 1849-1851 |
| 12317-14316 | 3'-sequence[2] | 2000 | — |

[1]5'-sequence includes 5'-UTR (untranslated region) and/or genomic sequences
[2]3'-sequence includes 3'-UTR (untranslated region) and/or genomic sequences The human HIPK4 polymorphism identified in a fetal brain library (see above) was also found in a public database. A search of public single nucleotide polymorphism (SNP) databases revealed that human HIPK4 contains 25 SNPs. Only one of the SNPs in the public databases occurs in the coding region of human HIPK4 (G/A at position 10817 in SEQ ID NO:3 (in exon 3), equivalent to position 905 in SEQ ID NO:1).

CLUSTAL W sequence alignment analysis revealed that the deduced amino acid sequence of human HIPK4 shows significant homology to the kinase catalytic domains of known HIPKs (FIG. 6). The predicted kinase catalytic domain of human HIPK4 (FIG. 2D) has the highest homology to the kinase catalytic domains of human HIPK2 and HIPK3 (~50% identity; ~66% similarity), but it is also homologous to the kinase catalytic domains of other known HIPKs, including mouse HIPK1, HIPK2, and HIPK3, rat HIPK3, *C. elegans* HIPK1, and *S. cerevisiae* yak1. Interestingly, human HIPK4 lacks the homeodomain-interacting domain of the known HIPKs, which is a family signature of these kinases (e.g., Kim et al. (1998) *J. Biol. Chem.* 273:25875-79).

Figure 7B:
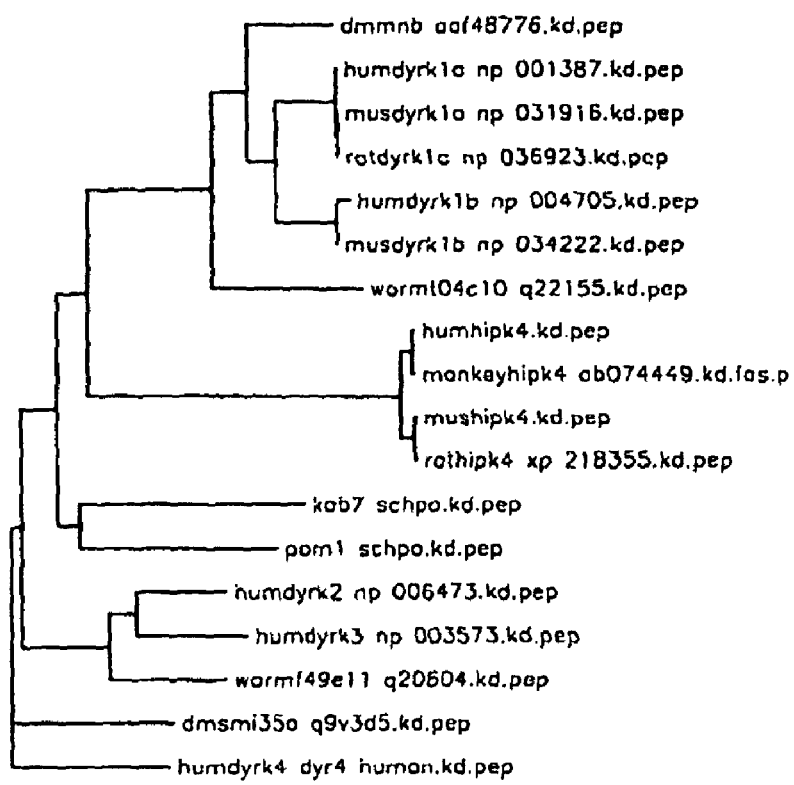
FIG. 7 shows a comparison of the amino acid sequences (FIG. 7A) of the conserved kinase catalytic domains of human HIPK4 (humHIPK4; from SEQ ID NO:2), mouse HIPK4 (musHIPK4; from SEQ ID NO:5), monkey HIPK4 (monkeyHIPK4; from SEQ ID NO:8), and rat HIPK4 (ratHIPK4; from SEQ ID NO:17) with the kinase catalytic domains of several known DYRKs, or dual-specificity tyrosine phosphorylated and regulated kinases (musDYRK1A; ratDYRK1A; humDYRK1A; humDYRK1B; musDYRK1B; dmMNB; wormT04C10; dmSMI35A; humDYRK4; humDYRK2; humDYRK3; wormF49E11; KAB7_SCHPO; and POM1_SCHPO). A phylogenetic tree of the aligned sequences, including public accession codes/numbers, is presented in FIG. 7B.

Human HIPK2 has been predicted to be a member of the dual-specificity tyrosine phosphorylated and regulated kinase (DYRK) family based on conservation of their kinase catalytic domains (Hofmann et al. (2000) *Biochimie* 82:1123-27). DYRKs are serine/threonine kinases believed to be involved in the regulation of growth and development, particularly in the brain (Himpel et al. (2000) *J. Biol. Chem.* 275:2431-38). Mutations in the *Drosophila* DYRK homolog, protein kinase MNB, results in specific defects in the development of the central nervous system (Tejedor et al. (1995) *Neuron* 14:287-301). Likewise, overexpression of the human DYRK homolog, DYRK1A, which maps to the "Down syndrome critical region" of chromosome 21, causes neurodevelopmental delay, motor abnormalities, and cognitive deficits in mice similar to those seen in Down syndrome (Altafaj et al. (2001) *Hum. Mol. Genet.* 10:1915-23). Based on the strong homology of HIPK4 to known HIPKs at the kinase catalytic domain, HIPK4 is also predicted to be a member of the DYRK kinase family. CLUSTAL W sequence alignment analysis of the deduced amino acid sequence of human HIPK4 and known members of the DYRK family revealed significant homology at the kinase catalytic domain (FIG. 7). In particular, human HIPK4 possesses the consensus sequence, Y— hydrophobic aliphatic residue—T/S—R— aromatic residue—Y—R—S/A-P-E (see FIG. 7, amino acids 168-178), thought to confer proline specificity at the P+1 site in DYRK substrates (see Himpel et al., supra).

Example 1.2

Identification of Mouse HIPK4 Genomic and cDNA Sequences

A mouse HIPK4 virtual cDNA was extracted from public murine genomic DNA databases based on the human HIPK4 cDNA sequence. This virtual cDNA sequence was used to isolate a physical clone, with an open reading frame of 1848 bp (coding sequence of 1851 bp), from a mouse full-length testis library using GeneTrapper technology (Invitrogen, Carlsbad, Calif.). This mouse HIPK4 cDNA sequence, which shares 87% identity with the human HIPK4 cDNA sequence, is set forth in SEQ ID NO:4. The deduced amino acid sequence of mouse HIPK4, which is 87% identical and 89% similar to the deduced amino acid sequence of human HIPK4, is set forth in SEQ ID NO:5. Like human HIPK4, the 616 amino acid mouse HIPK4 polypeptide (FIG. 3A) is predicted to have an ATP binding domain ranging from amino acids 17-40 (FIG. 3B), a serine/threonine binding domain ranging from amino acids 132-144 (FIG. 3C), and a protein kinase domain ranging from amino acids 11-347 (FIG. 3D).

Similar to human HIPK4, the deduced amino acid sequence of mouse HIPK4 shows significant homology to the kinase catalytic domains of known HIPKs (FIG. 6). The predicted kinase catalytic domain of mouse HIPK4 (FIG. 3D) has the highest homology to the kinase catalytic domains of mouse HIPK1, HIPK2, and HIPK3 (50% identity; 66% similarity), but it is also homologous to the kinase catalytic domains of other know HIPKs, including human HIPK1 and HIPK2, rat HIPK3, *C. elegans* HIPK1, and *S. cerevisiae* yak1. Like human HIPK4, mouse HIPK4 lacks the homeodomain-interacting domain of the known HIPKs (FIG. 6) and contains the proline specificity consensus sequence of known DYRKs (FIG. 7).

Comparison of the mouse HIPK4 cDNA sequence with the genomic DNA used to extract the "virtual" cDNA described above revealed that the mouse HIPK4 locus, which maps to mouse chromosome 7A3 (position numbers 19103968-19115318, according to Celera mapping), contains 4 exons and 3 introns (see Table 4, below). A comparison of Table 3 and Table 4 shows that exonic size and intronic position are well conserved between the human and mouse HIPK4 DNA sequences. The mouse HIPK4 genomic DNA sequence is set forth in SEQ ID NO:6.

TABLE 4

| Region in SEQ ID NO: 6 | Sequence Attribute | Length (nt) | Position in SEQ ID NO: 4 |
|---|---|---|---|
| 1-2000 | 5'-sequence[1] | 2000 | — |
| 2001-2465 | Exon 1 | 465 | 1-465 |
| 2466-6779 | Intron 1 | 4314 | — |
| 6780-7136 | Exon 2 | 357 | 466-822 |
| 7137-7432 | Intron 2 | 296 | — |
| 7433-8281 | Exon 3 | 849 | 823-1671 |
| 8282-9171 | Intron 3 | 890 | — |
| 9172-9348 | Exon 4 | 177 | 1672-1848 |
| 9349-9351 | Stop | 3 | 1849-1851 |
| 9352-11351 | 3'-sequence[2] | 2000 | — |

[1]5'-sequence includes 5'-UTR (untranslated region) and/or genomic sequences
[2]3'-sequence includes 3'-UTR (untranslated region) and/or genomic sequences A search of public SNP databases revealed that mouse HIPK4 contains 12 SNPs, of which 2 (both silent) occur in the coding region of mouse HIPK4 (A/G at position 2045 in SEQ ID NO:6 (in exon 1), equivalent to position 45 in SEQ ID NO:4; and G/C at position 2444 in SEQ ID NO:6 (in exon 1), equivalent to position 444 in SEQ ID NO:4).

Example 1.3

Identification of Monkey HIPK4 cDNA Sequence

The cDNA sequence of human HIPK4 was used to search against public nucleic acid databases using BLASTN. An open reading frame of 1848 bp (coding sequence of 1851 bp) was identified that corresponded to *Macaca fascicularis* (crab-eating macaque) testis cDNA clone QtsA-20664 (GenBank AB074449). This monkey HIPK4 ortholog, which shares 96.2% identity with the human HIPK4 cDNA sequence and 86% identity with the mouse HIPK4 cDNA, is set forth in SEQ ID NO:7. The deduced amino acid sequence of monkey HIPK4, which is 97.1% identical and 97.7% similar to the deduced amino acid sequence of human HIPK4, and 87% identical and 90% similar to the deduced amino acid sequence of mouse HIPK4, is set forth in SEQ ID NO:8. Like human and mouse HIPK4, the 616 amino acid monkey HIPK4 polypeptide (FIG. 4A) is predicted to possess an ATP binding domain ranging from amino acids 17-40 (FIG. 4B), a serine/threonine binding domain ranging from amino acids 132-144 (FIG. 4C), and a protein kinase domain ranging from amino acids 11-347 (FIG. 4D).

Similar to human and mouse HIPK4, the deduced amino acid sequence of monkey HIPK4 shows significant homology to the kinase catalytic domains of known HIPKs (FIG. 6). The predicted kinase catalytic domain of monkey HIPK4 (FIG. 4D) has the highest homology to the kinase catalytic domains of human HIPK2 and HIPK3 (~50% identity, ~66% similarity), but it is also homologous to the kinase catalytic domains of other known HIPKs, including mouse HIPK1, HIPK2, and HIPK3, rat HIPK3, *C. elegans* HIPK1, and *S. cerevisiae* yak1. Like human and mouse HIPK4, monkey HIPK4 lacks the homeodomain-interacting domain of the known HIPKs (FIG. 6) and contains the proline specificity consensus sequence of known DYRKs (FIG. 7).

Example 1.4

Identification of Rat HIPK4 cDNA Sequence

A search of public nucleic acid databases using the human HIPK4 cDNA sequence also identified an open reading frame of 1848 bp (coding sequence of 1851 bp) that corresponded to a predicted *Rattus norvegicus* sequence (GenBank XM218355) similar to monkey HIPK4 identified in Example 1.3 above. Three ESTs (GenBank BF543284, BF389548, and AI716144) supported regions of the predicted sequence, including the final predicted exon and the 3' UTR, suggesting that this rat sequence is an actual expressed HIPK4. This rat HIPK4 ortholog, which shares 83% identity with the human HIPK4 cDNA sequence, 95% identity with the mouse HIPK4 cDNA, and 84% identity with the monkey HIPK4 CDNA, is set forth in SEQ ID NO:16. The deduced amino acid sequence of rat HIPK4, which is 87% identical and 88% similar to the deduced amino acid sequence of human HIPK4, 98% identical and 98% similar to the deduced amino acid sequence of mouse HIPK4, and 87% identical and 89% similar to the deduced amino acid sequence of monkey HIPK4, is set forth in SEQ ID NO:17. Like human, mouse, and monkey HIPK4, the 616. amino acid rat HIPK4 polypeptide (FIG. 5A) is predicted to possess an ATP binding domain ranging from amino acids 17-40 (FIG. 5B), a serine/threonine binding domain ranging from amino acids 132-144 (FIG. 5C), and a protein kinase domain ranging from amino acids 11-347 (FIG. 5D).

Similar to human, mouse, and monkey HIPK4, the deduced amino acid sequence of rat HIPK4 shows significant homology to the kinase catalytic domains of known HIPKs (FIG. 6). The predicted kinase catalytic domain of rat HIPK4 (FIG. 5D) has the highest homology to the kinase catalytic domains of human HIPK2 and HIPK3 (~50% identity, ~66% similarity), but it is also homologous to the kinase catalytic domains of other known HIPKs, including mouse HIPK1, HIPK2, and HIPK3, rat HIPK3, *C. elegans* HIPK1, and *S. cerevisiae* yak1. Like human, mouse, and monkey HIPK4, rat HIPK4 lacks the homeodomain-interacting domain of the known HIPKs (FIG. 6) and contains the proline specificity consensus sequence of known DYRKs (FIG. 7).

Example 2

Tissue Expression of the Human HIPK4

Example 2.1

Northern Analysis

Tissue expression of HIPK4 was first assessed by Northern analysis using a Clontech Multiple Tissue Northern (MTN) Blot (Palo Alto, Calif.). MTN blots contain approximately 1 µg of polyA⁺RNA/lane from twelve human tissues. The RNA is run on a denaturing formaldehyde 1.0% agarose gel, transferred to a nylon membrane, and fixed by UV irradiation. Based upon the cDNA sequence of human HIPK4 (SEQ ID NO:2), PCR primers were designed to amplify a 521 nt fragment (SEQ ID NO:13) from human genomic DNA. The primers were designed to amplify coding sequence corresponding to exon 3 of human HIPK4, thereby avoiding the highly conserved kinase domain and reducing the possibility of non-specific hybridization. The sequences of the forward (SEQ ID NO:14) and reverse (SEQ ID NO:15) primers were:

```
5' ACGAGACCACCCACTACTAC 3'    (forward primer)

5' GAGATGCTCTCCTTCCTCCC 3'    (reverse primer)
```

The amplified fragment was gel purified and sequence confirmed. The fragment was labeled with [$\alpha^{32}$P]dCTP by random priming to produce the Northern probe.

The MTN blot was hybridized with 1-2×10$^6$ cpm/mL $^{32}$P probe in QuickHyb® buffer (Stratagene, La Jolla, Calif.) along with 150 µg denatured sonicated salmon sperm DNA at 68° C. for 2-4 hours. The blot was washed with 2×SSC/1% SDS and 0.1×SSC/1% SDS multiple times at 65° C. Following the washes, the blot was exposed to film for multiple exposures. A very strong HIPK4 transcript approximately 5 kb in size was detected in brain tissue, while weaker transcripts of approximately 5 kb and 3 kb were detected in skeletal muscle.

Example 2.2

Tissue Array Analysis

The tissue expression of human HIPK4 was further analyzed using a Clontech Multiple Tissue Expression (MTE) array. MTE arrays are dot blots containing normalized loadings of polyA⁺RNA from 72 different human tissues and eight different control RNAs and DNAs.

The MTE blot was hybridized with 1-2×10$^6$ cpm/mL $^{32}$P probe as produced in Example 2.1 in QuickHyb® buffer along with 150 µg denatured sonicated salmon sperm DNA and 30 µg denatured human Cot-1 DNA at 65° C. for approximately 18 hours. The blot was washed with 2×SSC/1% SDS and 0.1×SSC/1% SDS multiple times at 65° C. Following the washes, the blot was exposed to film for multiple exposures. Prominent HIPK4 expression was detected in multiple subcortical, mid-brain regions known to be involved in age-related neurodegenerative diseases (e.g., Alzheimer's and Parkinson's) and in mood disorders (e.g., depression), including hippocampus, amygdala, and caudate nucleus. Weaker signals above background were also detected in testis, skeletal muscle, and lung.

Example 2.3

Cancer Array Analysis

The expression of human HIPK4 in various human cancers was assessed using a Clontech Cancer Profiling Array (CPA). CPAs are dot blots of 241 paired cDNA samples from tumor and adjacent normal tissue from individual patients.

The CPA blot was hybridized with 1-2×10$^6$ cpm/mL $^{32}$P probe as produced in Example 2.1 in ExpressHyb® buffer (Clontech) along with 150 µg denatured sonicated salmon sperm DNA and 30 µg denatured human Cot-1 DNA at 65° C. for approximately 18 hours. The blot was washed with 2×SSC/1% SDS and 0.1×SSC/1% SDS multiple times at 65° C. Following the washes, the blot was exposed to film for multiple exposures. Human HIPK4 appeared to be somewhat downregulated in kidney tumors. The results of these tissue expression studies indicate that human HIPK4 is a novel kinase that is strongly expressed in brain and may be improperly expressed in tumors. Thus, human HIPK4 is a potential target for the development of human therapeutic agents, particularly those useful for treating neurological diseases and cancers.

Example 3

Inhibition of HIPK4 Expression Using Antisense Oligonucleotides or RNAi

The ability of antisense oligonucleotides complementary to HIPK4 nucleic acid sequences, or siRNA duplexes (RNAi) matching HIPK4 nucleic acid sequences, to inhibit expression of HIPK4 can be assessed in vitro by treating cells in tissue culture that naturally or recombinantly express HIPK4. Decreases in HIPK4 RNA levels can be detected by Northern analysis or RNA protection assays or other methods known in the art, while decreases in HIPK4 protein levels can be detected by Western analysis (e.g., below) or immunoassay or other methods known in the art.

For Western analysis, cells are plated at an appropriate concentration in 96-well tissue culture-treated plates. For the SW480 colon carcinoma cell line, 30,000 cells/well is an appropriate cell concentration. The desired antisense oligonucleotide or siRNA duplex is transfected into the cells using an appropriate transfection reagent. Criteria for selecting and designing these oligonucleotides or duplexes are well known in the art (see, e.g., Elbashir et al. (2001) *EMBO J.* 20:6877-88). For SW480 cells, Lipofectamine 2000 (Invitrogen) is an appropriate transfection reagent. The following two master mixes/well are prepared in quantities sufficient to run samples in triplicate:

Mix 1: 30 µl OptiMEM reduced serum media (Invitrogen)+ 0.35 µl Lipofectamine

Mix 2: 30 µl OptiMEM+500 nM antisense oligonucleotide or 200 nM siRNA duplex.

Mix 2 for control cells lacks antisense oligonucleotide or siRNA duplex.

Mix 1 is added to Mix 2 and incubated at room temperature for 20 min. While the incubation is proceeding, cells are washed with 100 µl/well OptiMEM. Cells are refed with 100 µl/well OptiMEM, returned to a humidified environment and incubated at 37° C., 5% $CO_2$.

The OptiMEM is removed from the cells and the Lipofectamine mixture containing the antisense oligonucleotide or siRNA duplex is added. The cells are incubated at 37° C., 5% $CO_2$, in a humidified environment for 4 h. The Lipofectamine mixture is removed and the cells refed with antibiotic-free media. The cells are incubated at 37° C., 5% $CO_2$, in a humidified environment for 5 days.

The media is removed, the cells are washed with 1× phosphate-buffered saline, and 120 µl protein sample in Laemmli buffer is added to each well. The cells are scraped from the well, replicates are pooled, and the DNA is sheared by passing the samples through a 20-gauge needle.

Ten µl of each sample is loaded onto a 4-20% acrylamide Tris/glycine gel (Novex, Invitrogen, Carlsbad, Calif.). The gel is run for 2 h at a constant 90 V in Tris/glycine/SDS (TGS). The separated proteins are transferred to Hybond ECL nitrocellulose (Amersham Biosciences Corp, Piscataway, N.J.) in 1×TGS, 20% methanol for 2 h at a constant 30 V using a Novex transfer unit.

The membranes are removed and rinsed in reverse-osmosis deionized water. The membranes are blocked in blocking buffer (1× Tris-buffered saline (TBS), 1% NP40, 5% nonfat dry milk) for 1 h at room temperature with shaking. A primary antibody that recognizes HIPK4 is diluted approximately 1:1000 in blocking buffer and added to the membrane at 4° C. overnight with shaking.

The membrane is washed three times in wash buffer (1×TBS, 1% NP40) for 15 min at room temperature with shaking. The membrane is then washed once in 1×TBS for 5 min at room temperature with shaking. The horseradish peroxidase-conjugated secondary antibody appropriate for the primary antibody is diluted approximately 1:5000 in blocking buffer and added to the membrane for 2 h at room temperature with shaking, The membrane is washed three times in wash buffer for 15 min at room temperature with shaking. The membrane is then washed once in 1×TBS for 5 min at room temperature with shaking. The blot is then developed using ECL reagents according to manufacturer's recommendations. A decrease in the amount of HIPK4 protein in treated cells compared with control cells would indicate that the antisense oligonucleotide or siRNA duplex was effective in inhibiting expression of HIPK4.

Example 4

Overexpression of Human HIPK4 Suppresses Programmed Cell Death (PCD)

Human HIPK4 cDNA expression plasmids were generated to investigate the effects of overexpression in standard cell death assays. The human HIPK4 coding sequence was amplified by PCR with primers containing appropriate restriction sites from a human fetal brain cDNA library (Clontech) and cloned into a pEGFP-N vector (Clontech) to provide a plasmid expressing the HIPK4 protein fused at its carboxy terminus to enhanced green fluorescent protein (EGFP). Transfections into HeLa cells and the human neuroblastoma line SH-SY5Y were performed by standard lipid-based protocols.

Cells expressing EGFP were scored for nuclear morphology at 48 h posttransfection to assess the effects of human HIPK4 on programmed cell death (PCD). The overexpression of human HIPK4 did not induce PCD in either SH-SY5Y cells or HeLa cells as compared to EGFP alone. Cells were also treated 48 h posttransfection with staurosporine (STS), a potent inducer of PCD, for 4 h to evaluate potential protective effects of human HIPK4 expression. Human HIPK4 inhibited the induction of PCD by STS in both SH-SY5Y cells (250 nM STS) and HeLa cells (1 µM STS) by 30-40%. Human HIPK4 expression also reduced PCD in HeLa cells by ~40% following 24 h treatment with 100 µM etoposide, an agent with a different mechanism of action than STS. These data demonstrate that human HIPK4 has a general protective activity against apoptosis, evident in different cell lines and with different initiating injuries.

Because it was important to determine whether the protective effect of human HIPK4 was a result of protein kinase activity, amino acids lysine-40 and aspartate-136 of human HIPK4, predicted to be functionally essential for kinase activity based on homology to known kinases (Bairoch and Claverie (1988) *Nature* 331:22), were substituted by site-directed mutagenesis (serine for lysine-40 (SEQ ID NOs:192-195), and tryptophan for aspartate-136 (SEQ ID NOs:194-197)) using the QuickChange™ System (Stratagene) according to Manufacturer's recommendations. Substitution of lysine-40 and aspartate-136, individually (SEQ ID NOs: 192-193 and 196-197, respectively) or together (SEQ ID NOs:194-195), almost completely abrogated the protective effect of human HIPK4 in HeLa cells against injury by 1 µM STS, indicating that the anti-PCD activity of human HIPK4 is mediated by its predicted protein kinase function.

The protective effects of human HIPK4 were also examined in a model system of neurodegeneration. Rat cerebral granular neurons (CGNs) grown in culture were transfected with an expression vector for human HIPK4/EGFP fusion protein or EGFP vector alone by a calcium phosphate method (Xia et al. (1996) *J. Neurosci.* 16:5425-36). BCl-$x_L$ expressed as an EGFP fusion protein served as a neuroprotective positive control (Boise et al. (1993) *Cell* 74:597-608). Transfected CGNs were injured 48 h posttransfection by transfer to growth media containing low levels of $K^+$ (5 mM) and no serum for 24 h. CGNs expressing EGFP were scored for apoptosis by nuclear morphology. CGNs expressing HIPK4 were substantially protected from apoptotic injury as compared to vector alone (~60% greater cell survival); in fact, this level of protection was equivalent to that seen in CGNs transfected with the antiapoptotic BCl-$x_L$ protein.

What is claimed is:

1. A method of enhancing apoptosis in a cell population in a cell culture comprising:
   (a) providing the cell population with a vector comprising the polynucleotide set forth in SEQ ID NO: 194, wherein the polynucleotide is operably linked to an expression control sequence; and
   (b) expressing the polynucleotide in the cell population, such that the cell population produces the polypeptide encoded by the polynucleotide,
   wherein the polypeptide enhances apoptosis in the cell population.

2. The method of claim 1, wherein the cell population is a cancer cell population.

3. The method of claim 1, wherein the cell population is a neuronal cell population.

4. The method of claim 1, wherein the cell population is selected from COS cells, CHO cells, 293 cells, A431 cells, 3T3 cells, CV-1 cells, HeLa cells, L cells, BHK21 cells, HL-60 cells, U937 cells, HaK cells, Jurkat cells, SH-SY5Y, normal diploid cells, cell strains derived from in vitro culture of primary tissue, and primary explants.

* * * * *

SEQUENCE LISTING

<160> NUMBER OF SEQ ID NOS: 197

<210> SEQ ID NO 1
<211> LENGTH: 1851
<212> TYPE: DNA
<213> ORGANISM: Homo sapiens
<220> FEATURE:
<221> NAME/KEY: CDS
<222> LOCATION: (1)..(1848)

<400> SEQUENCE: 1

| | | | | | | | | | | | | | | | | |
|---|---|---|---|---|---|---|---|---|---|---|---|---|---|---|---|---|
| atg | tcc | acc | atc | cag | tcg | gag | act | gac | tgc | tac | gac | atc | atc | gag | gtc | 48 |
| Met | Ser | Thr | Ile | Gln | Ser | Glu | Thr | Asp | Cys | Tyr | Asp | Ile | Ile | Glu | Val | |
| 1 | | | | 5 | | | | | 10 | | | | | 15 | | |

| ttg | ggc | aag | ggg | acc | ttc | ggg | gag | gta | gcc | aag | ggc | tgg | cgg | cgg | agc | 96 |
|---|---|---|---|---|---|---|---|---|---|---|---|---|---|---|---|---|
| Leu | Gly | Lys | Gly | Thr | Phe | Gly | Glu | Val | Ala | Lys | Gly | Trp | Arg | Arg | Ser | |
| | | | 20 | | | | | 25 | | | | | 30 | | | |

| acg | ggc | gag | atg | gtg | gcc | atc | aag | atc | ctc | aag | aat | gac | gcc | tac | cgc | 144 |
|---|---|---|---|---|---|---|---|---|---|---|---|---|---|---|---|---|
| Thr | Gly | Glu | Met | Val | Ala | Ile | Lys | Ile | Leu | Lys | Asn | Asp | Ala | Tyr | Arg | |
| | | 35 | | | | | 40 | | | | | 45 | | | | |

| aac | cgc | atc | atc | aag | aac | gag | ctg | aag | ctg | ctg | cac | tgc | atg | cga | ggc | 192 |
|---|---|---|---|---|---|---|---|---|---|---|---|---|---|---|---|---|
| Asn | Arg | Ile | Ile | Lys | Asn | Glu | Leu | Lys | Leu | Leu | His | Cys | Met | Arg | Gly | |
| | 50 | | | | | 55 | | | | | 60 | | | | | |

| cta | gac | cct | gaa | gag | gcc | cac | gtc | atc | cgc | ttc | ctt | gag | ttc | ttc | cat | 240 |
|---|---|---|---|---|---|---|---|---|---|---|---|---|---|---|---|---|
| Leu | Asp | Pro | Glu | Glu | Ala | His | Val | Ile | Arg | Phe | Leu | Glu | Phe | Phe | His | |
| 65 | | | | | 70 | | | | | 75 | | | | | 80 | |

| gac | gcc | ctc | aag | ttc | tac | ctg | gtc | ttt | gag | ctg | ctg | gag | caa | aac | ctt | 288 |
|---|---|---|---|---|---|---|---|---|---|---|---|---|---|---|---|---|
| Asp | Ala | Leu | Lys | Phe | Tyr | Leu | Val | Phe | Glu | Leu | Leu | Glu | Gln | Asn | Leu | |
| | | | | 85 | | | | | 90 | | | | | 95 | | |

| ttc | gag | ttc | cag | aag | gag | aac | aac | ttc | gcg | ccc | ctc | ccc | gcc | cgc | cac | 336 |
|---|---|---|---|---|---|---|---|---|---|---|---|---|---|---|---|---|
| Phe | Glu | Phe | Gln | Lys | Glu | Asn | Asn | Phe | Ala | Pro | Leu | Pro | Ala | Arg | His | |
| | | | | 100 | | | | | 105 | | | | | 110 | | |

| atc | cgt | aca | gtc | acc | ctg | cag | gtg | ctc | aca | gcc | ctg | gcc | cgg | ctc | aag | 384 |
|---|---|---|---|---|---|---|---|---|---|---|---|---|---|---|---|---|
| Ile | Arg | Thr | Val | Thr | Leu | Gln | Val | Leu | Thr | Ala | Leu | Ala | Arg | Leu | Lys | |
| | | | 115 | | | | | 120 | | | | | 125 | | | |

| gag | ctg | gct | atc | atc | cac | gct | gat | ctc | aag | cct | gag | aac | atc | atg | ctg | 432 |
|---|---|---|---|---|---|---|---|---|---|---|---|---|---|---|---|---|
| Glu | Leu | Ala | Ile | Ile | His | Ala | Asp | Leu | Lys | Pro | Glu | Asn | Ile | Met | Leu | |
| | | 130 | | | | | 135 | | | | | 140 | | | | |

| gtg | gac | cag | acc | cgc | tgc | ccc | ttc | agg | gtc | aag | gtg | att | gac | ttc | gga | 480 |
|---|---|---|---|---|---|---|---|---|---|---|---|---|---|---|---|---|
| Val | Asp | Gln | Thr | Arg | Cys | Pro | Phe | Arg | Val | Lys | Val | Ile | Asp | Phe | Gly | |
| 145 | | | | | 150 | | | | | 155 | | | | | 160 | |

| tcc | gcc | agc | att | ttc | agc | gag | gtg | cgc | tac | gtg | aag | gag | cca | tac | atc | 528 |
|---|---|---|---|---|---|---|---|---|---|---|---|---|---|---|---|---|
| Ser | Ala | Ser | Ile | Phe | Ser | Glu | Val | Arg | Tyr | Val | Lys | Glu | Pro | Tyr | Ile | |
| | | | | 165 | | | | | 170 | | | | | 175 | | |

| cag | tcg | cgc | ttc | tac | cgg | gcc | cct | gag | atc | ctg | ctg | ggg | ctg | ccc | ttc | 576 |
|---|---|---|---|---|---|---|---|---|---|---|---|---|---|---|---|---|
| Gln | Ser | Arg | Phe | Tyr | Arg | Ala | Pro | Glu | Ile | Leu | Leu | Gly | Leu | Pro | Phe | |
| | | | | 180 | | | | | 185 | | | | | 190 | | |

| tgc | gag | aag | gtg | gac | gtg | tgg | tcc | ctg | ggc | tgc | gtc | atg | gct | gag | ctg | 624 |
|---|---|---|---|---|---|---|---|---|---|---|---|---|---|---|---|---|
| Cys | Glu | Lys | Val | Asp | Val | Trp | Ser | Leu | Gly | Cys | Val | Met | Ala | Glu | Leu | |
| | | | 195 | | | | | 200 | | | | | 205 | | | |

| cac | ctg | ggc | tgg | cct | ctc | tac | ccc | ggc | aac | aac | gag | tac | gac | cag | gtg | 672 |
|---|---|---|---|---|---|---|---|---|---|---|---|---|---|---|---|---|
| His | Leu | Gly | Trp | Pro | Leu | Tyr | Pro | Gly | Asn | Asn | Glu | Tyr | Asp | Gln | Val | |
| | | 210 | | | | | 215 | | | | | 220 | | | | |

| cgc | tac | atc | tgc | gaa | acc | cag | ggc | ctg | ccc | aag | cca | cac | ctg | ttg | cac | 720 |
|---|---|---|---|---|---|---|---|---|---|---|---|---|---|---|---|---|
| Arg | Tyr | Ile | Cys | Glu | Thr | Gln | Gly | Leu | Pro | Lys | Pro | His | Leu | Leu | His | |
| 225 | | | | | 230 | | | | | 235 | | | | | 240 | |

| gcc | gcc | tgc | aag | gcc | cac | cac | ttc | ttc | aag | cgc | aac | ccc | cac | cct | gac | 768 |
|---|---|---|---|---|---|---|---|---|---|---|---|---|---|---|---|---|
| Ala | Ala | Cys | Lys | Ala | His | His | Phe | Phe | Lys | Arg | Asn | Pro | His | Pro | Asp | |
| | | | | 245 | | | | | 250 | | | | | 255 | | |

```
gct gcc aac ccc tgg cag ctc aag tcc tcg gct gac tac ctg gcc gag      816
Ala Ala Asn Pro Trp Gln Leu Lys Ser Ser Ala Asp Tyr Leu Ala Glu
        260                 265                 270 acg aag gtg cgc cca ttg gag cgc cgc aag tat atg ctc aag tcg ttg      864
Thr Lys Val Arg Pro Leu Glu Arg Arg Lys Tyr Met Leu Lys Ser Leu
275                 280                 285 gac cag att gag aca gtg aat ggt ggc agt gtg gcc agt cgg cta acc      912
Asp Gln Ile Glu Thr Val Asn Gly Gly Ser Val Ala Ser Arg Leu Thr
        290                 295                 300 ttc cct gac cgg gag gcg ctg gcg gag cac gcc gac ctc aag agc atg      960
Phe Pro Asp Arg Glu Ala Leu Ala Glu His Ala Asp Leu Lys Ser Met
305                 310                 315                 320 gtg gag ctg atc aag cgc atg ctg acc tgg gag tca cac gaa cgc atc     1008
Val Glu Leu Ile Lys Arg Met Leu Thr Trp Glu Ser His Glu Arg Ile
                325                 330                 335 agc ccc agt gct gcc ctg cgc cac ccc ttc gtg tcc atg cag cag ctg     1056
Ser Pro Ser Ala Ala Leu Arg His Pro Phe Val Ser Met Gln Gln Leu
        340                 345                 350 cgc agt gcc cac gag acc acc cac tac tac cag ctc tcg ctg cgc agc     1104
Arg Ser Ala His Glu Thr Thr His Tyr Tyr Gln Leu Ser Leu Arg Ser
355                 360                 365 tac cgc ctc tcg ctg caa gtg gag ggg aag ccc ccg acg ccc gtc gtg     1152
Tyr Arg Leu Ser Leu Gln Val Glu Gly Lys Pro Pro Thr Pro Val Val
        370                 375                 380 gcc gca gaa gat ggg acc ccc tac tac tgt ctg gct gag gag aag gag     1200
Ala Ala Glu Asp Gly Thr Pro Tyr Tyr Cys Leu Ala Glu Glu Lys Glu
385                 390                 395                 400 gct gcg ggt atg ggc agt gtg gcc ggc agc agc ccc ttc ttc cga gag     1248
Ala Ala Gly Met Gly Ser Val Ala Gly Ser Ser Pro Phe Phe Arg Glu
                405                 410                 415 gag aag gca cca ggt atg caa aga gcc atc gac cag ctg gat gac ctg     1296
Glu Lys Ala Pro Gly Met Gln Arg Ala Ile Asp Gln Leu Asp Asp Leu
        420                 425                 430 agt ctg cag gag gct ggg cat ggg ctg tgg ggt gag acc tgc acc aat     1344
Ser Leu Gln Glu Ala Gly His Gly Leu Trp Gly Glu Thr Cys Thr Asn
435                 440                 445 gcg gtc tcc gac atg atg gtc ccc ctc aag gca gcc atc act ggc cac     1392
Ala Val Ser Asp Met Met Val Pro Leu Lys Ala Ala Ile Thr Gly His
        450                 455                 460 cat gtg ccc gac tcg ggc cct gag ccc atc ctg gcc ttc tac agc agc     1440
His Val Pro Asp Ser Gly Pro Glu Pro Ile Leu Ala Phe Tyr Ser Ser
465                 470                 475                 480 cgc ctg gca ggc cgc cac aag gcc cgc aag cca cct gcg ggt tcc aag     1488
Arg Leu Ala Gly Arg His Lys Ala Arg Lys Pro Pro Ala Gly Ser Lys
                485                 490                 495 tcc gac tcc aac ttc agc aac ctc att cgg ctg agc cag gtc tcg cct     1536
Ser Asp Ser Asn Phe Ser Asn Leu Ile Arg Leu Ser Gln Val Ser Pro
        500                 505                 510 gag gat gac agg ccc tgc cgg ggc agc agc tgg gag gaa gga gag cat     1584
Glu Asp Asp Arg Pro Cys Arg Gly Ser Ser Trp Glu Glu Gly Glu His
515                 520                 525 ctc ggg gcc tct gct gag cca ctg gcc atc ctg cag cga gat gag gat     1632
Leu Gly Ala Ser Ala Glu Pro Leu Ala Ile Leu Gln Arg Asp Glu Asp
        530                 535                 540 ggg ccc aac att gac aac atg acc atg gaa gct gag agg cca gac cct     1680
Gly Pro Asn Ile Asp Asn Met Thr Met Glu Ala Glu Arg Pro Asp Pro
545                 550                 555                 560 gag ctc ttc gac ccc agc agc tgt cct gga gaa tgg ctg agt gag cca     1728
Glu Leu Phe Asp Pro Ser Ser Cys Pro Gly Glu Trp Leu Ser Glu Pro
                565                 570                 575
```

```
gac tgc acc ctg gag agc gtc agg ggc cca cgg gct cag ggg ctc cca    1776
Asp Cys Thr Leu Glu Ser Val Arg Gly Pro Arg Ala Gln Gly Leu Pro
            580                 585                 590 ccc cgc cgc tcc cac cag cat ggt cca ccc cgg ggg gcc acc agc ttc    1824
Pro Arg Arg Ser His Gln His Gly Pro Pro Arg Gly Ala Thr Ser Phe
            595                 600                 605 ctc cag cat gtc acc ggg cac cac tga                                1851
Leu Gln His Val Thr Gly His His
            610                 615

<210> SEQ ID NO 2
<211> LENGTH: 616
<212> TYPE: PRT
<213> ORGANISM: Homo sapiens

<400> SEQUENCE: 2

Met Ser Thr Ile Gln Ser Glu Thr Asp Cys Tyr Asp Ile Ile Glu Val
1               5                   10                  15

Leu Gly Lys Gly Thr Phe Gly Glu Val Ala Lys Gly Trp Arg Arg Ser
                20                  25                  30

Thr Gly Glu Met Val Ala Ile Lys Ile Leu Lys Asn Asp Ala Tyr Arg
            35                  40                  45

Asn Arg Ile Ile Lys Asn Glu Leu Lys Leu Leu His Cys Met Arg Gly
    50                  55                  60

Leu Asp Pro Glu Glu Ala His Val Ile Arg Phe Leu Glu Phe Phe His
65                  70                  75                  80

Asp Ala Leu Lys Phe Tyr Leu Val Phe Glu Leu Leu Glu Gln Asn Leu
                85                  90                  95

Phe Glu Phe Gln Lys Glu Asn Asn Phe Ala Pro Leu Pro Ala Arg His
            100                 105                 110

Ile Arg Thr Val Thr Leu Gln Val Leu Thr Ala Leu Ala Arg Leu Lys
        115                 120                 125

Glu Leu Ala Ile Ile His Ala Asp Leu Lys Pro Glu Asn Ile Met Leu
    130                 135                 140

Val Asp Gln Thr Arg Cys Pro Phe Arg Val Lys Val Ile Asp Phe Gly
145                 150                 155                 160

Ser Ala Ser Ile Phe Ser Glu Val Arg Tyr Val Lys Glu Pro Tyr Ile
                165                 170                 175

Gln Ser Arg Phe Tyr Arg Ala Pro Glu Ile Leu Leu Gly Leu Pro Phe
            180                 185                 190

Cys Glu Lys Val Asp Val Trp Ser Leu Gly Cys Val Met Ala Glu Leu
        195                 200                 205

His Leu Gly Trp Pro Leu Tyr Pro Gly Asn Asn Glu Tyr Asp Gln Val
    210                 215                 220

Arg Tyr Ile Cys Glu Thr Gln Gly Leu Pro Lys Pro His Leu Leu His
225                 230                 235                 240

Ala Ala Cys Lys Ala His His Phe Phe Lys Arg Asn Pro His Pro Asp
                245                 250                 255

Ala Ala Asn Pro Trp Gln Leu Lys Ser Ser Ala Asp Tyr Leu Ala Glu
            260                 265                 270

Thr Lys Val Arg Pro Leu Glu Arg Arg Lys Tyr Met Leu Lys Ser Leu
        275                 280                 285

Asp Gln Ile Glu Thr Val Asn Gly Gly Ser Val Ala Ser Arg Leu Thr
    290                 295                 300

Phe Pro Asp Arg Glu Ala Leu Ala Glu His Ala Asp Leu Lys Ser Met
```

-continued

```
            305                 310                 315                 320
    Val Glu Leu Ile Lys Arg Met Leu Thr Trp Glu Ser His Glu Arg Ile
                    325                 330                 335

Ser Pro Ser Ala Ala Leu Arg His Pro Phe Val Ser Met Gln Gln Leu
                340                 345                 350

Arg Ser Ala His Glu Thr Thr His Tyr Tyr Gln Leu Ser Leu Arg Ser
                355                 360                 365

Tyr Arg Leu Ser Leu Gln Val Glu Gly Lys Pro Pro Thr Pro Val Val
            370                 375                 380

Ala Ala Glu Asp Gly Thr Pro Tyr Tyr Cys Leu Ala Glu Glu Lys Glu
    385                 390                 395                 400

Ala Ala Gly Met Gly Ser Val Ala Gly Ser Ser Pro Phe Phe Arg Glu
                    405                 410                 415

Glu Lys Ala Pro Gly Met Gln Arg Ala Ile Asp Gln Leu Asp Asp Leu
                420                 425                 430

Ser Leu Gln Glu Ala Gly His Gly Leu Trp Gly Glu Thr Cys Thr Asn
                435                 440                 445

Ala Val Ser Asp Met Met Val Pro Leu Lys Ala Ala Ile Thr Gly His
            450                 455                 460

His Val Pro Asp Ser Gly Pro Glu Pro Ile Leu Ala Phe Tyr Ser Ser
    465                 470                 475                 480

Arg Leu Ala Gly Arg His Lys Ala Arg Lys Pro Pro Ala Gly Ser Lys
                    485                 490                 495

Ser Asp Ser Asn Phe Ser Asn Leu Ile Arg Leu Ser Gln Val Ser Pro
                500                 505                 510

Glu Asp Asp Arg Pro Cys Arg Gly Ser Ser Trp Glu Glu Gly Glu His
                515                 520                 525

Leu Gly Ala Ser Ala Glu Pro Leu Ala Ile Leu Gln Arg Asp Glu Asp
            530                 535                 540

Gly Pro Asn Ile Asp Asn Met Thr Met Glu Ala Glu Arg Pro Asp Pro
    545                 550                 555                 560

Glu Leu Phe Asp Pro Ser Ser Cys Pro Gly Glu Trp Leu Ser Glu Pro
                    565                 570                 575

Asp Cys Thr Leu Glu Ser Val Arg Gly Pro Arg Ala Gln Gly Leu Pro
                580                 585                 590

Pro Arg Arg Ser His Gln His Gly Pro Pro Arg Gly Ala Thr Ser Phe
                595                 600                 605

Leu Gln His Val Thr Gly His His
            610                 615

<210> SEQ ID NO 3
<211> LENGTH: 14317
<212> TYPE: DNA
<213> ORGANISM: Homo sapiens

<400> SEQUENCE: 3
gagttgaggt tttgtcatgt tggcaaggct ggtctcaaac tcctgacctc aggtgatccg    60
cccaccttgg cctctcaaag tgctgggatt acaggcgtaa gccaccactc ctggccaggc   120
actttaaaaa cttctttgtg ccttgatttt ctcttccata aatccctac tttgtatgtt    180 gtaaggatca gataagactt ctaaagaact tcatccttgt ttaaatgttt tgatgttaca   240
ttttctttta cttttttttt tttttttgag acggagtttc actcttgttg cccaggctgg   300
agtgcaatgg cgcaatcttg gctcactgca accccacctc ccgcgttcaa gcagttctca   360
```

```
tacctcagcc tgccgacctc agcctcttga gtagctggga ctacaggcat gtgctaacac    420
acccggctaa ttttgtattt ttagtagaga cggggtttct ccatgttggt caggctggtc    480
tcgaactccc gacctcaggt gatccacctg cctcagcctc ccaaagtgct gggattacag    540
gcatgagcca ccgagcccgg cccgctgtta aatattctaa tctggctgga gtggtggctc    600
atgtctacaa tcccagcact ttggaaggtt gaggcaggag gatcacttga ggccaggagg    660
atcacttgag accagcctgg acaacatagt gagacccccat ttctacaaaa aattaaaaag    720
ataaataaaa atgaacactt tttttttttt tttgagatgg agtctcgctc tgtcacccag    780
gctggagtgc agtggtgcaa tctcggctca ctgcaacctc cacctcccgg gttcaagcta    840
ttcttctgcc ttagcctccc gagtagctgg gactacaggc gcctccact atgcctggct    900 aattttagt attttagta gagacagagt ttcaccgtgt tagccaggat ggtctcgatc    960
tcctgacctt atgatctgcc ttccttggcc tcccaaagtg ctgggattac aggcgtgacc   1020
caccgcaccc agccaaaaat aaatacattt tctaatttgg cctcaacatc tcccccaagc   1080
tgcttcttat ccatgtccat ttctcgggga ctgccccttc atcccagagc cctaggcccg   1140
ttcttagaca gctcccgcct ttccctcaaa ccgtcggtct cacggctgct ctcctggcc   1200 ttttgagtgt ctcatccatt ggcctcgccc tctcctcccc aacctctccc atctgtgccc   1260
tgtcctggac tctttccctg gcttgggct tccactctta cccgctccaa cctatccctt   1320
ttcatacagt aactttctga cactcatatc tgaccctgcc ctcccctgct caaagccctt   1380
ctgtggctcc ccagtgccct cagaacagaa tccaaactcc ttagcctggc attcagggcc   1440
ttttacaacc tcaccccaca gtagccacag actgggacag gagttttctg aacacagaca   1500
cacacacatc acatctccca agctcaagaa gcccacctttt cctcactcct gccttatccc   1560
cattcctgta tgcccaaggc ccacgattag accccctct gtcaacactt cacctgtttg   1620
gtctttgcaa gattccgcca ctgggcgggg aggggggccc agcctggtac cccacccca   1680 ctccagccag ggctcaggtc tccaacaaca gaaccagagc cactcaacag cgctggaacc   1740
cattcggtgg ggcctggggc ccctcatccc aagccaggag ggtttctggg gaggggtgca   1800 gccccctggca gactgacagt gtggcctggg ggtttggggg tgccagggaa gcaggggcca   1860
acctcatagg aggagacacg agtgcggttc tctttccccc actgggggc ctgctgtgtc   1920 agcagccagg cgggaggcct gggcggcaga gccagtggta caggggcctg gcagggcgg   1980 tgtctggcag cagcggcacc atgtccacca tccagtcgga gactgactgc tacgacatca   2040
tcgaggtctt gggcaagggg accttcgggg aggtagccaa gggctggcgg cggagcacgg   2100
gcgagatggt ggccatcaag atcctcaaga tgacgcctta ccgcaaccgc atcatcaaga   2160
acgagctgaa gctgctgcac tgcatgcgag gcctagaccc tgaagaggcc cacgtcatcc   2220
gcttccttga gttcttccat gacgccctca gttctacct ggtctttgag ctgctggagc   2280 aaaaccttt cgagttccag aaggagaaca acttcgcgcc cctccccgcc cgccacatcc   2340
gtacagtcac cctgcaggtg ctcacagccc tggcccggct caaggagctg gctatcatcc   2400
acgctgatct caagcctgag aacatcatgc tggtggacca gacccgctgc cccttcaggg   2460
tcaaggtgag taggggtcgt ctagggtggc tgcgtcccta gttccttgtc ttttccccag   2520
cttcttccag ccctagattt tttttttaat tttttaaaat tattattatt attatttttg   2580
agacggagtt tcattctgtt acccaggctt gagtgcagtg gcgcaatctc agctcactgc   2640
aactccgcct cctgggttca agtgattatc ctgcctcagc ctcccgagtt gctgggatta   2700
cagggatgcg ccaccacgcc cagctaattt ttttttttgta cttatcagag acggggtgat   2760
```

```
gatggcatga tcttggttca ctgcctccgc ctcccgggtt caagcgattc tcctgcctca    2820
gcctcctgag tagctgggaa tacaggtgcc cgccacccat gcccggctaa tttttgtatt    2880
tttagtagag atggggtttc gccatgttgg ccaggctggt ctcaaactcc tgaccttgtg    2940
atccacctgc ctcagcctcc caaagtgctg ggattacagg cgtgagccac cacgcccagc    3000 caattttgt gttttttggt agaaacagga tttcatcatg ttgcccaggc tggtctcaaa     3060
gtcctgagtt caagcaatct gcccaccttg gcctcaacaa agtgctggaa ttacaagtgt    3120
gagccaccat gcccagtcct ctgtctgctt ttgagtttga tactgtctgg atgcttctga    3180
accaggggca ccctgagggc aaggctgggg ctgacttaat catcgctgtg tccctgacat    3240
ctcccagcac tgcagtcatg gagccagtgc taaatgaatg cttgccagag acacagagac    3300
agaaaaaggt ggattattct gccccaagag gtggaaggac agagacccag ggaagcaggg    3360
acttccacaa acacagcagg ggacagacag gacggatcca cagcacctgg ccggcattat    3420 caccccccact gtctctgtgg aaggaatgaa ttcattccac aaacatagac taagtgccca    3480
gggtcactca gcctcttggg tactgaagcc ctggcactct gggatcagaa tagcaattaa    3540
taaccatttc atgatactgc tttctgcaag tgaaaggtga gggatggcca ggtgcggtgg    3600
ctcacgcctg taatcccagc actttgggag gccgaggcgg gtggatcacc tgaggtcagg    3660
agttcaagac cagcctgacc aatatggtga aacctcgtct ctgctaaaag tataaaaatt    3720
agccgggtgt ggtggcgggc acctgtaatc ctagctactc agaggctga agcagataaa     3780 tcgcttagaa cccgggaggc agaggttgca gtgagctgag attacgccac tgcactccag    3840
cctgggcgac agaggaagtc cctctgtctc agaaaaaaaa aaaaaaaaaa ctaaactaaa    3900
attagctagg cgtggtggca catacctgga atcccagtta gttgggggc agaggcagga     3960 gactcacttg aacttgggag gcagaggttt tgcagtgagc tgagatcacg ccactgcact    4020
ccagcctggg cgacagagct cgactctgtc tcaacacaaa acaaaaacaa aaaactgaga    4080
aatggctgaa tgaaaagcag aaaaactcag agaaggaaac aggctggcca ggtgtggtgg    4140
cccaagcctg taatcccagc actttgggag gctgaggcag gtggatcacc tgaggtcaga    4200
agctcaagac cagcctggcc aacatggtga atcctgtct ctattaaaaa tacaaaactt      4260
agccagatgt ggtggggtgc acctgtaatc cagctactt gggaggctga tgcaggagaa     4320
tcgcttgaac ccatatgggg gcggaggttg cagtgagccg agatcatgcc gctgcactcc    4380
agcttggaca aaagagtgaa gccacctgaa aagaaaaag aaaaagaaac aggccaagag     4440
agagtcacgg agattcaggg tgaaaatggc agacagctcc accagaggca tggggagaga    4500
caaaggcttt cggccattcg caatgttggt tccgcagctg ttggccaagc acctgtcatg    4560
tgtcaaaggc ctgtgacgag tgtgaacagt gcctgaagag gaagacagaa gaggaccggg    4620
acttcaggga ggtgtcttcc tagtggacga cacagagaca gagatggaaa gagagagaga    4680
gacactgaga gacaagagac aggcaagtga tggagaggca gttgcaaaga aagaacgaga    4740
ggtacaaatg gccaggcaca gtggctcatg cctagaatct caggactttg ggaggccgag    4800
gtgggaggat tactagagcc caggagttca agaccagcct gggtaacatg gtgaaaaccc    4860
atctctacta aaaatacaaa aattagccgg gcatggtggc atgtgactgt agtcccagct    4920
acttgggagg ctgaggcagg agaatcgctt gaacgtggag ggtggaggtt gccttgagcc    4980
gagattgcgc cactgcattc cagcctgggt gacagggtga gccactgtct caaatgagag    5040
acagagagag agagatacaa gcaagagatg gaaagagaat gaaggaactc aaagcccata    5100
```

```
catacattca ttcattcact cattatttac tgagccctg ctgtgtgcca agccctgttc    5160
taggcatcta gggatacagt attgaacaaa atggataaat tctttgccct cgtgggactg   5220
acatcctcgc tggggagaga aatgctgaga gaggccaggt gcagggcctc atgcctataa   5280
tcccagcatg ttgggaggct gaggcaggag gatcacttga gcccaggagc catcctgggc   5340
aacatagtga gacccatctc tatctctaca aaaagttaaa aaattagctg ggtatggagg   5400
tgcatgcctg tggtcccagc tactcaggag gctgaggcgg gaggatcttg tgagccctgg   5460
agttcgcggc tacagtgagc tacgatggtg ccactgtact ccagcctggg tgatagagca   5520
agaccctgtc tctaaaaagg aaaaaagggc tgggcgccgt ggctcacgcc tgtaatccca   5580
acactttggg aggctgaggc gggcagatca tctgagtcag gagtttgaga ccagcctggc   5640
taacatggtg aaaccccgcc tgtctctacc aaaaatgcaa aagattagcg cttgtaatcc   5700
cagctactca ggaggctgag gcaggagaat cacttgaatc cagtaggtgg aggttgcagt   5760
gagccaagat cacaccactg ctctccagcc tggccaacag agcgagactc cgtcacaaaa   5820
aaataaataa ttaaaaaata aaattaaaat aaaaaattaa gagatatagt gtgtgaaatg   5880
gcattaagag caatggtgga cctgggtgcg gtggctcacg cctgtcctag cactttggga   5940
ggccgaggcg agtggatcac ctgcggtcag gagttcgaga ccagcctggc catcatcgtg   6000
aaaccccgtc tctactaaaa atataaaaat tagctgcgca tggtggtgtg cacctgtaat   6060
cccagctact gggaggctg aagcaggaga atcactggaa cctgggagga ggaggttgca    6120
gtgagccaag attgcaccat tgcactccag cctgggtgac aagagcaaaa ctctgtctca   6180
aaaacctccg actcaaaaaa aaaaaaaaaa aaaaaaaaa gaaaagaaaa gaaaagaaa    6240 aacaggggcc tggccgggga tagaaaggat ggggactgat ggctgatgct ttcacagaat   6300
gattagggaa ggtctcactg agaaggtgat catttttttt tgtcctgcct ttcaccttt    6360 gatagaaagg tgacatttga gtaaagacct gaaggaggtg aggcagggag ccctgtgctc   6420
atgcagggaa gagcattcca ggcagaggga acagcgagtg caaaagccct gagctgggaa   6480
tgtctgactt gttcaaggaa tagtgaggag acccttgtgg ctggaggagg gtgagtgatg   6540
gggagagtgg gagatgtggc agagaggtga cagagcagac attggagacc tgtgggccac   6600
ggtgaggact ttggcttttg tcacaggatg tggctatgag caggggagga cccaatctat   6660
cccgggcggc cacaggatcc ctctggatgc ttgtgacaga cagactaggg ggcagaggag   6720
aggagcaggg agaccagcga ggagaccccc gcgttggtct aggttggaaa ggatgcagga   6780
taggaccagg gtcggggctg tggatggcat gcagaggag cagattctag atctgttggc    6840
tgatggacaa ggtgtggggt gcaagaggaa gagtagggtc ctaaccctcc tttgcatagt   6900
tctagtggag agaaacagag acagagtcag tcactcgaac cagacacaaa ggctggaaga   6960
gacagagata gggacttaac aactacggcc acagctgggt gcggtggctc atgcctgtaa   7020
ttccagcact tagggaggct gaggagggca gatcatctga ggtcaggagt ttaagaccag   7080
cctggccaac agggtgaaac cccgtctcta ctaaaaatac aaaaattagc agggcatggt   7140
ggtgtgcacc tgtagaccca gctattcagg agactgagc tggagaatca cttgaaccca   7200
ggaggcagag gttgcaatga gccaagattg cgccactgca ctttagcctg gcgacagag   7260 tgagactcgg tctcaaaaaa aaaaaaaaaa ccaacaaagg ctgggtgcgg tggctcacgc   7320
ctgtaatccc agcactttgg gaggccgagg cgggtgggtc acatgaggtc aggagttcga   7380
gaccagcctg gccaacatag tgaaaccccca tctctactaa aaatacaaaa aattagccgg   7440
gtgtggtggt gggcgcctgc aatcccagct actcaggagg ctaaggcagg agaatcgctt   7500
```

```
gaaccgggga ggtggaggtt gcagtgtgct gagatcgtgc cattgcactc cagactgggc    7560
aacaagagtg agactctgtc tcaaacaaac aaacaaacaa acaaacaaaa accaacaaag    7620
caactaaaga atcacagacc cagagatggc cagagtcaaa tagcagatgc aggaagatgc    7680
caggtgaaag atgccggggt ggcccagctc ggctgtccct gctgcttgac ctgcccactc    7740
gccctcttcc ccaccccgca caggtgattg acttcggatc cgccagcatt ttcagcgagg    7800
tgcgctacgt gaaggagcca tacatccagt cgcgcttcta ccgggcccct gagatcctgc    7860
tggggctgcc cttctgcgag aaggtggacg tgtggtccct gggctgcgtc atggctgagc    7920
tgcacctggg ctggcctctc taccccggca acaacgagta cgaccaggtg cgctacatct    7980
gcgaaaccca gggcctgccc aagccacacc tgttgcacgc cgcctgcaag gcccaccact    8040
tcttcaagcg caaccccac cctgacgctg ccaacccctg gcagctcaag tcctcggctg    8100
actacctggc cgagacgaag gtaagggaaa agttgggtga gggcagtcag tgtgggggct    8160
gttacatgaa aaaaaattct agggtgggca acgtggctca cacctgtaat tccagcactt    8220
tgggaggctg tggtgggagg atcccttgag cctaggggtt tgagaccagc ctggggaaca    8280
tagtgagacc tcctctttat aaaacatgga aaaaaaatc agctgggcac ggtggtatgg    8340
gcctattgtc ccagatacat gggaggctga ggcaggagaa ttccttgagc ctgggaggtc    8400
caggctacag tgaactatga tcatgccact acacttgagc ctgggtgaca gagcaagact    8460
ctgtttcaaa aagaaaaatc tatcagacca gaagaatgga gtgaaagaa caaaaaacag    8520 aggctgggtg tggtggctta cgcctgtaat cccagcactt tgggagtccg aggtgggtgg    8580
atcacgaggt caggagttta agaccagcct ggccaagatg atgaaaccca gtctctacta    8640
aaaacacaaa aaattagctg gcgcagtgg cagacgcctg taattccagc tactcggcgg    8700
gctgaggcag gagaatcgct tgaacccaga gggcggaggt tgcagtgagc cgagatccca    8760
ccactgcact ccagcctggg caacagagtg agactccgtc tcaaaaaaaa aaaaaaaaa    8820 gaaagaaaag aaaaatattt ttttctttt tttttaagac ggagtcttga tctgttgctc    8880
aggctggagt gcagtggtgc ggtctcagct cactgcaacc tctgcctccc aggttcaaga    8940
gattctcctg cctcagcctc ctgagtagct gggcttacag gcacccacca tcacacccgg    9000
caattttttt gtattttac tagagacggg gttttaccat gttggccagg ctggtctcag    9060
acacccgacc tcgtgatcca cccacctcga cctcccaaag cagtgagatt acaggcatga    9120
gccaccgcgc tcggccaaaa aaatatttt ttaataattg aaaaaaaaaa tttctgggct    9180
aaacctcaat gaggactgga acttgggggt cagcctaggg cattttcaca gcaagaaaga    9240
gctgcatgag atcaaatgtg ggactggtca gcaactgcag caagatagat ctgggggaga    9300
aactgcaggg agaattagat gtttggaagt cagatgtggg ggctgctcta gcaagagaga    9360
tctgggtcat actataagtg tgacaggacg attgggcag cttctctgcc agcttcagct    9420
ccggggtcag caacttgtgt ggcaagaggg attagaccac agagaatata tgaggtctga    9480
gattggctat gagaattgcg agagaggcca ggtgcagtgg cttatgcctg tagtccacgc    9540
actttggtgg gggccaaggc aggaggatca cttgaagtca ttgtgggcga catagcaaga    9600
ctgtgtctct agaaaaaatt tttttaaaa tttagccagg catggtggca cacaccggta    9660
gttccaagct acttgggagg ctgaggtggg aagatcactt gaacccagga gttggcagtt    9720
gcagtgagct atgattgcac cactacaccc cagtctgggc gacacagcaa gaccctgttt    9780
aaaaaaaagg atctaaggcc aggcacagtg gctcacacct gtaatcccag cactttggga    9840
```

```
ggccgaggtg ggtggatcac ctgaggtcag gagttcgaga acagcctggc caacatggtg    9900
aaacccatc tctactaaaa atacaaaaat tagctgggca tggtggtgga cacctgtaat     9960
tccagctgct caggaggctg aggcaggaga atcgcttgaa cctgggaggt ggaggttgca   10020
gtgagccgag attgtaccac tgcactccag cctgggcaac aagagtgaaa ctctgtctca   10080
cacacataca aaaaaaaaa aaaaaaaaa aaaaaaagg gatctgagtg agacctcagg      10140
tgagtctaga ggtttggggc agcagccagt ctgctacctc tgtggctttg cccctcccat   10200
ctgtgcagca agagcctggg ttagacagca gaggggacta ggagtttgag gtcataggtc   10260
ttgatttcac agcaagaagg gtctggatgg gaccacaggt gagactaaaa gtcaatggca   10320
gtttaatagc aggggggtgac aaactactat agcaagaagg gtctgggttt gaccaccagg  10380
aggcctggga tcaagtgtgg agctgtggca gtaagaggga cctggatttg attccaggga  10440
ggactagaga ttccgggcag cccttctgct agctgctggt aggggctgca cccatggtgc   10500
tgaagggac tggaggtctg gggcaagggg tggaacttgg gccagtgatt tgggttcgat   10560
tagaggggct tgggtgtgac ggatccaggg tggccctcct agcagccaga gagctccaag   10620
gcagatcatg ggcagacctg gaagtcgggg ctacatgtgg gtgccacagc aggagtgccc  10680
agggccctag ccctgcacaa tggtcaaccc tgcccccttc tccatgcccc gccaggtgcg  10740
cccattggag cgccgcaagt atatgctcaa gtcgttggac cagattgaga cagtgaatgg  10800
tggcagtgtg gccagtcggc taaccttccc tgaccgggag gcgctggcgg agcacgccga  10860
cctcaagagc atggtggagc tgatcaagcg catgctgacc tgggagtcac acgaacgcat  10920
cagccccagt gctgccctgc gccacccctt cgtgtccatg cagcagctgc gcagtgccca  10980
cgagaccacc cactactacc agctctcgct gcgcagctac cgcctctcgc tgcaagtgga  11040
ggggaagccc cccacgcccg tcgtggccgc agaagatggg accccctact actgtctggc  11100
tgaggagaag gaggctgcgg gtatgggcag tgtggccggc agcagcccct tcttccgaga  11160
ggagaaggca ccaggtatgc aaagagccat cgaccagctg gatgacctga gtctgcagga  11220
ggctgggcat gggctgtggg gtgagacctg caccaatgcg gtctccgaca tgatggtccc  11280
cctcaaggca gccatcactg gccaccatgt gcccgactcg ggccctgagc ccatcctggc  11340
cttctacagc agccgcctgg caggccgcca aaggcccgc aagccaccctg cgggttccaa   11400
gtccgactcc aacttcagca acctcattcg gctgagccag gtctcgcctg aggatgacag  11460
gccctgccgg ggcagcagct gggaggaagg agagcatctc ggggcctctg ctgagccact  11520
ggccatcctg cagcgagatg aggatgggcc caacattgac aacatgacca tggaagctga  11580
ggtgagccgg gtgcgttcag gatacgatta gggtgggagg aggctcagca cacactcacc  11640
cgtgctcagg atatgattag tgtgtgagga ggctcaacac acactcaccc atgttcagga  11700
tacaattagg gacttaggag gctcagcaca cacctaatac cgtcaagata tgataaggct  11760
cagcacttac tcagctactt ccaggctgtg acaaaaactc agggcacagt aatctactta  11820
taagaagctt gataaagagc ctgggcaaca tagtgagatc ccgtctgcac caaaaaatta  11880
gaaatattag ctggttttgg tggcatgcac ctgtagtccc agctactcag gaggctgagg  11940
tgggaggatc acttgagcca gggaggtcga ggctgcagtg agctgtcatc acatcactac  12000
aaaggggcaa taaaggccca gcactggtaa gaccctagca catgctcacc ctcatcagga  12060
ggaggtgaca gaggctcagc agacactaat acactaacac tgcttggctg atgcccctct  12120
ctcttccccc acagaggcca gaccctgagc tcttcgaccc cagcagctgt cctggagaat  12180
ggctgagtga gccagactgc accctggaga gcgtcagggg cccacgggct cagggctcc   12240
```

```
caccccgccg ctcccaccag catggtccac cccgggggc caccagcttc ctccagcatg    12300
tcaccgggca ccactgatgg tgattccacc cctgcccatc actggggct gcgctagctg     12360
ggctggcatt ccctcccaac ctgaactgct cctcagagcc atctcctgaa cccacaaatt    12420
attcttacag aaagatagtt atccagaaat tctcattccc cgtctgcggt gcggtgcgtg    12480
cctgcacacc tctcctaaac acagcagggc tttggagtct ggcccatgct ccttggccag    12540
aaggacagca ggaaagggg ctgcaccccg ctggccctgc gctcgcctt ggccctgctg     12600
cctctgtcta tttcaatata gaactgttca gcagtcctgc ttcaagcctg ctctcactgc    12660
ctggggcttg gactggccct gggggaatg ggggctccag gctggcaccc agtgacttgc     12720
tctgcgatgc tgggcccagc tgaccactgg cttaggcggg agcctgggct gctgtcacac    12780
taggagggaa aagctgtgct tggttgacta acccttgtcc taaatacgct atgtgcttgg    12840
cgtgttggga atccaccctc agaacatgct gtgttcagta tgtgttaatc aagtttgccg    12900
gatgctgggg tctccttgtc tgttgacctg tccttcctac atgtttacag ggttggcatg    12960
cactcaccca catttgggac gtgctgggtg taaatccact tggcaggcct aaattcacac    13020
ttggtgcaca ctctggtgct cagccatgct tgttcaccct tgggatgtgg caatggtttg    13080
gtccctgctg atcaatctgg gaacatgctt ctctgcagca catacccatg ctggctacat    13140
gagtgctaag tccatgccgg ccacagggt ggcacgctgc atgctcagca caggtcagcc     13200
catgtacact acatgttaag ggctcagcac atgccaaccc atgccagcac atgctgaggg    13260
ctcagtacat gctaacccac actggtcaca cactgagggc tcagcacatg ccagtgacat    13320
gttgagggct cagcacaaaa agatgtcccc accagaggcc catgccagct gtcccctacc    13380
cctgcacccc atctcacacc actcagtcag gcacaggctg tacagacaag ttatttactt    13440
attataaccc tgggcccttt ttgccctgga aagtgggggt gggccagggg gccaggccca    13500
gcatgcaccc ccatttcttt gggggctgat ccctccccca gctctgctgg gtcccggggc    13560
cacagcgtca ggccggtggg ggtggaggta gaggtgggag agcaggggag agagcctgag    13620
gagccacaat ggggcagaca gaagcggggg cgcggggaca gggaccgtga cccagagcac    13680
ctgggtccgc gggggcccag caggccttgg cctgcccact ggatcgggcc tcagagcagg    13740
cggcaggcgt tgcccacgct gtcagctgag gtgtcaaggt catggctgta agggagtcc     13800
cagtccctca ggaaaatggc ctccagctgg ctccgcaggc cgcccctccc attctgcgtc    13860
accagcagcg aggtgcccgc cgtctccgtg aagtagttgc cagaccagtt ggaggttcct    13920
agagaggaat gggtggagca taagggcacc ctcgggggc cgcccctggt gtctgaaccc     13980
cctcttcttc agcgccccgt ggtgctcaag acactcaccg atgtaggtgg cgcgttcagt    14040
caccatgtac ttgttgtggt tgacacgggc atatgggatt cgagcctggg cctcatccgc    14100
ggggaccaca aagagtttct gagtgggagg ggaggatggg aaggagtgtg agaggcaggg    14160
ggagtcggag gagccccggg atcagggagc agagtgtgga gcgagatctg tgggactcca    14220
ctgcttccca cagaatcctc gggggccaga acagggccag gtggaggggc cctctgagaa    14280
cgaaagctga aagggaggcc ccggtggtct catttgc                              14317
```

<210> SEQ ID NO 4
<211> LENGTH: 1851
<212> TYPE: DNA
<213> ORGANISM: Mus musculus
<220> FEATURE:
<221> NAME/KEY: CDS
<222> LOCATION: (1)..(1848)

<400> SEQUENCE: 4

```
atg gcc acc atc cag tca gag act gac tgc tac gac atc att gaa gtt      48
Met Ala Thr Ile Gln Ser Glu Thr Asp Cys Tyr Asp Ile Ile Glu Val
1               5                   10                  15 ctg ggc aag ggc act ttt gga gag gtg gcc aag ggc tgg cgt cgg agt      96
Leu Gly Lys Gly Thr Phe Gly Glu Val Ala Lys Gly Trp Arg Arg Ser
            20                  25                  30 aca ggt gaa atg gtg gcc atc aag atc ctg aag aac gat gcg tac cga     144
Thr Gly Glu Met Val Ala Ile Lys Ile Leu Lys Asn Asp Ala Tyr Arg
        35                  40                  45 agc cgc atc atc aag aat gag ctg aag ctg ctg cgc tgc gtg cga ggc     192
Ser Arg Ile Ile Lys Asn Glu Leu Lys Leu Leu Arg Cys Val Arg Gly
    50                  55                  60 ctg gac cct gac gag gcc cac gtt atc cgc ttc ctt gag ttc ttc cac     240
Leu Asp Pro Asp Glu Ala His Val Ile Arg Phe Leu Glu Phe Phe His
65                  70                  75                  80 gat gcc ctc aag ttc tac ctg gtc ttc gag ctt ttg gag caa aac ctc     288
Asp Ala Leu Lys Phe Tyr Leu Val Phe Glu Leu Leu Glu Gln Asn Leu
                85                  90                  95 ttt gag ttc cag aaa gag aac aac ttc gca ccc ctt cct gcc agg cac     336
Phe Glu Phe Gln Lys Glu Asn Asn Phe Ala Pro Leu Pro Ala Arg His
            100                 105                 110 atc cgc acg gtc aca ctg cag gta cta aga gcg ctg gcc cgg ctc aag     384
Ile Arg Thr Val Thr Leu Gln Val Leu Arg Ala Leu Ala Arg Leu Lys
        115                 120                 125 gaa ctg gcc atc atc cac gct gac ctc aag cct gaa aac att atg ttg     432
Glu Leu Ala Ile Ile His Ala Asp Leu Lys Pro Glu Asn Ile Met Leu
    130                 135                 140 gta gac cag acg cgc tgc ccc ttc agg gtc aag gtg atc gac ttt ggc     480
Val Asp Gln Thr Arg Cys Pro Phe Arg Val Lys Val Ile Asp Phe Gly
145                 150                 155                 160 tcg gcc agc ata ttc agt gag gta cgc tat gtg aag gag cct tac atc     528
Ser Ala Ser Ile Phe Ser Glu Val Arg Tyr Val Lys Glu Pro Tyr Ile
                165                 170                 175 cag tcc cgc ttc tac agg gcc cca gag atc ctg ctg ggg ctg ccc ttc     576
Gln Ser Arg Phe Tyr Arg Ala Pro Glu Ile Leu Leu Gly Leu Pro Phe
            180                 185                 190 tgt gag aag gtg gac gtg tgg tct ctg ggc tgt gtc atg gcc gag cta     624
Cys Glu Lys Val Asp Val Trp Ser Leu Gly Cys Val Met Ala Glu Leu
        195                 200                 205 cat ctg ggc tgg cct ctc tac cca ggc aac aat gag tat gac cag gtg     672
His Leu Gly Trp Pro Leu Tyr Pro Gly Asn Asn Glu Tyr Asp Gln Val
    210                 215                 220 cgc tac atc tgt gag acc cag ggc tta ccc aag ccc cat ttg ctg cat     720
Arg Tyr Ile Cys Glu Thr Gln Gly Leu Pro Lys Pro His Leu Leu His
225                 230                 235                 240 gcg gct cgc aag gct cac cac ttc ttc aag cgt aac ccc cac ccc gat     768
Ala Ala Arg Lys Ala His His Phe Phe Lys Arg Asn Pro His Pro Asp
                245                 250                 255 gcc acc aac ccc tgg cag ctg aag tcc tct gct gac tac cta gct gag     816
Ala Thr Asn Pro Trp Gln Leu Lys Ser Ser Ala Asp Tyr Leu Ala Glu
            260                 265                 270 acc aag gta cgt cct ctg gag cgc cgc aag tac atg ctc aaa tcc ttg     864
Thr Lys Val Arg Pro Leu Glu Arg Arg Lys Tyr Met Leu Lys Ser Leu
        275                 280                 285 gac cag att gag aca gtg aat ggt ggt gga gct gtg agc cgg ctg agt     912
Asp Gln Ile Glu Thr Val Asn Gly Gly Gly Ala Val Ser Arg Leu Ser
    290                 295                 300
```

```
ttt cca gac cgg gag gcc ctg gcg gaa cac gca gac ctc aag agc atg      960
Phe Pro Asp Arg Glu Ala Leu Ala Glu His Ala Asp Leu Lys Ser Met
305                 310                 315                 320 gtg gag ctg atc aaa cgc atg ctg aca tgg gag tcg cac gaa cgc atc     1008
Val Glu Leu Ile Lys Arg Met Leu Thr Trp Glu Ser His Glu Arg Ile
                325                 330                 335 agt ccc agt gcg gcc ctg cgt cac ccc ttc gtg tcc atg cag cag ctg     1056
Ser Pro Ser Ala Ala Leu Arg His Pro Phe Val Ser Met Gln Gln Leu
            340                 345                 350 cgg agt gcc cac gag gcc acc cgc tac tac cag ctg tcg ctc aga ggc     1104
Arg Ser Ala His Glu Ala Thr Arg Tyr Tyr Gln Leu Ser Leu Arg Gly
        355                 360                 365 tgt cgg ctg tcc ctg cag gtg gat ggc aag cca ccc cca cct gtc ata     1152
Cys Arg Leu Ser Leu Gln Val Asp Gly Lys Pro Pro Pro Pro Val Ile
370                 375                 380 gcc agc gca gag gac ggg cct ccc tac tac cgc ctg gct gag gag gag     1200
Ala Ser Ala Glu Asp Gly Pro Pro Tyr Tyr Arg Leu Ala Glu Glu Glu
385                 390                 395                 400 gag act gca ggc ctg ggt ggt gtg aca ggc agt ggg tcc ttc ttc agg     1248
Glu Thr Ala Gly Leu Gly Gly Val Thr Gly Ser Gly Ser Phe Phe Arg
                405                 410                 415 gag gac aag gct ccg gga atg cag agg gcc atc gac cag ctc gat gac     1296
Glu Asp Lys Ala Pro Gly Met Gln Arg Ala Ile Asp Gln Leu Asp Asp
            420                 425                 430 ctg agt ctg caa gag gcc aga cgg ggg ctg tgg agc gac aca cgg gcc     1344
Leu Ser Leu Gln Glu Ala Arg Arg Gly Leu Trp Ser Asp Thr Arg Ala
        435                 440                 445 gac atg gtc tct gac atg ctg gtt cca ctc aaa gtg gcc agt acc agc     1392
Asp Met Val Ser Asp Met Leu Val Pro Leu Lys Val Ala Ser Thr Ser
450                 455                 460 cac cga gtc cct gac tca ggc cca gag cct atc ctg gcc ttc tac ggc     1440
His Arg Val Pro Asp Ser Gly Pro Glu Pro Ile Leu Ala Phe Tyr Gly
465                 470                 475                 480 agc cga ttg acc ggc cgc cat aag gcc cgc aag gcc cca gca ggc tcc     1488
Ser Arg Leu Thr Gly Arg His Lys Ala Arg Lys Ala Pro Ala Gly Ser
                485                 490                 495 aaa tct gac tcc aac ttc agt aac ctc att cgg ctg agc cag gcc tca     1536
Lys Ser Asp Ser Asn Phe Ser Asn Leu Ile Arg Leu Ser Gln Ala Ser
            500                 505                 510 cct gag gat gcc ggg ccc tgt cgg ggc agt ggc tgg gag gaa gga gaa     1584
Pro Glu Asp Ala Gly Pro Cys Arg Gly Ser Gly Trp Glu Glu Gly Glu
        515                 520                 525 ggc cgc acg acc tcc aca gag ccg tct gtc atc cca caa cgg gaa gga     1632
Gly Arg Thr Thr Ser Thr Glu Pro Ser Val Ile Pro Gln Arg Glu Gly
530                 535                 540 gat ggg cct ggc atc aaa gac agg ccc atg gat gcc gag agg cca ggc     1680
Asp Gly Pro Gly Ile Lys Asp Arg Pro Met Asp Ala Glu Arg Pro Gly
545                 550                 555                 560 cct gag ctc ttt gat ccc agc agc tgt cct gga gag tgg ctg agt gag     1728
Pro Glu Leu Phe Asp Pro Ser Ser Cys Pro Gly Glu Trp Leu Ser Glu
                565                 570                 575 cca gaa tgg acc cta gag ggc atc cgg ggg tct cga gct caa ggg ctc     1776
Pro Glu Trp Thr Leu Glu Gly Ile Arg Gly Ser Arg Ala Gln Gly Leu
            580                 585                 590 cca gct cac cat ccc cac ccc cac ggg cca ccc agg acc acc agc ttt     1824
Pro Ala His His Pro His Pro His Gly Pro Pro Arg Thr Thr Ser Phe
        595                 600                 605 ctg cag cat gtt gga ggg cac cac tga                                 1851
Leu Gln His Val Gly Gly His His
            610                 615
```

<210> SEQ ID NO 5
<211> LENGTH: 616
<212> TYPE: PRT
<213> ORGANISM: Mus musculus

<400> SEQUENCE: 5

```
Met Ala Thr Ile Gln Ser Glu Thr Asp Cys Tyr Asp Ile Ile Glu Val
1               5                   10                  15

Leu Gly Lys Gly Thr Phe Gly Glu Val Ala Lys Gly Trp Arg Arg Ser
            20                  25                  30

Thr Gly Glu Met Val Ala Ile Lys Ile Leu Lys Asn Asp Ala Tyr Arg
        35                  40                  45

Ser Arg Ile Ile Lys Asn Glu Leu Lys Leu Leu Arg Cys Val Arg Gly
    50                  55                  60

Leu Asp Pro Asp Glu Ala His Val Ile Arg Phe Leu Glu Phe Phe His
65                  70                  75                  80

Asp Ala Leu Lys Phe Tyr Leu Val Phe Glu Leu Leu Glu Gln Asn Leu
                85                  90                  95

Phe Glu Phe Gln Lys Glu Asn Asn Phe Ala Pro Leu Pro Ala Arg His
            100                 105                 110

Ile Arg Thr Val Thr Leu Gln Val Leu Arg Ala Leu Ala Arg Leu Lys
        115                 120                 125

Glu Leu Ala Ile Ile His Ala Asp Leu Lys Pro Glu Asn Ile Met Leu
    130                 135                 140

Val Asp Gln Thr Arg Cys Pro Phe Arg Val Lys Val Ile Asp Phe Gly
145                 150                 155                 160

Ser Ala Ser Ile Phe Ser Glu Val Arg Tyr Val Lys Glu Pro Tyr Ile
                165                 170                 175

Gln Ser Arg Phe Tyr Arg Ala Pro Glu Ile Leu Leu Gly Leu Pro Phe
            180                 185                 190

Cys Glu Lys Val Asp Val Trp Ser Leu Gly Cys Val Met Ala Glu Leu
        195                 200                 205

His Leu Gly Trp Pro Leu Tyr Pro Gly Asn Asn Glu Tyr Asp Gln Val
    210                 215                 220

Arg Tyr Ile Cys Glu Thr Gln Gly Leu Pro Lys Pro His Leu Leu His
225                 230                 235                 240

Ala Ala Arg Lys Ala His His Phe Phe Lys Arg Asn Pro His Pro Asp
                245                 250                 255

Ala Thr Asn Pro Trp Gln Leu Lys Ser Ser Ala Asp Tyr Leu Ala Glu
            260                 265                 270

Thr Lys Val Arg Pro Leu Glu Arg Arg Lys Tyr Met Leu Lys Ser Leu
        275                 280                 285

Asp Gln Ile Glu Thr Val Asn Gly Gly Ala Val Ser Arg Leu Ser
    290                 295                 300

Phe Pro Asp Arg Glu Ala Leu Ala Glu His Ala Asp Leu Lys Ser Met
305                 310                 315                 320

Val Glu Leu Ile Lys Arg Met Leu Thr Trp Glu Ser His Glu Arg Ile
                325                 330                 335

Ser Pro Ser Ala Ala Leu Arg His Pro Phe Val Ser Met Gln Gln Leu
            340                 345                 350

Arg Ser Ala His Glu Ala Thr Arg Tyr Tyr Gln Leu Ser Leu Arg Gly
        355                 360                 365

Cys Arg Leu Ser Leu Gln Val Asp Gly Lys Pro Pro Pro Val Ile
```

```
              370                 375                 380
Ala Ser Ala Glu Asp Gly Pro Pro Tyr Tyr Arg Leu Ala Glu Glu
385                 390                 395                 400

Glu Thr Ala Gly Leu Gly Gly Val Thr Gly Ser Gly Ser Phe Phe Arg
                405                 410                 415

Glu Asp Lys Ala Pro Gly Met Gln Arg Ala Ile Asp Gln Leu Asp Asp
            420                 425                 430

Leu Ser Leu Gln Glu Ala Arg Arg Gly Leu Trp Ser Asp Thr Arg Ala
        435                 440                 445

Asp Met Val Ser Asp Met Leu Val Pro Leu Lys Val Ala Ser Thr Ser
    450                 455                 460

His Arg Val Pro Asp Ser Gly Pro Glu Pro Ile Leu Ala Phe Tyr Gly
465                 470                 475                 480

Ser Arg Leu Thr Gly Arg His Lys Ala Arg Lys Ala Pro Ala Gly Ser
                485                 490                 495

Lys Ser Asp Ser Asn Phe Ser Asn Leu Ile Arg Leu Ser Gln Ala Ser
            500                 505                 510

Pro Glu Asp Ala Gly Pro Cys Arg Gly Ser Gly Trp Glu Glu Gly Glu
        515                 520                 525

Gly Arg Thr Thr Ser Thr Glu Pro Ser Val Ile Pro Gln Arg Glu Gly
    530                 535                 540

Asp Gly Pro Gly Ile Lys Asp Arg Pro Met Asp Ala Glu Arg Pro Gly
545                 550                 555                 560

Pro Glu Leu Phe Asp Pro Ser Ser Cys Pro Gly Glu Trp Leu Ser Glu
                565                 570                 575

Pro Glu Trp Thr Leu Glu Gly Ile Arg Gly Ser Arg Ala Gln Gly Leu
            580                 585                 590

Pro Ala His His Pro His Pro His Gly Pro Pro Arg Thr Thr Ser Phe
        595                 600                 605

Leu Gln His Val Gly Gly His His
    610                 615

<210> SEQ ID NO 6
<211> LENGTH: 11351
<212> TYPE: DNA
<213> ORGANISM: Mus musculus

<400> SEQUENCE: 6
ttcttcccct ctgatttctc accaaaatgt caagcttctt cttatttat ttttattctt      60 tatttattgg tttttcaaga gagggctttt cagccttgga tgtcctggaa ctcagtagac     120
ccgactggcc ttgaactcac agagatctac ctgcatcccc ctccggagtg ctgggattaa     180
gagcatgtgc cacaactgcc tggcaagcag cctcatcttc tatggtttcc atacttcaga     240
gctgacagat ctccattcct gggggtggg gggaggagct tctggggatg cctccataca     300
ccatatacgc catatacacc atatatacca tatcatcat ataccata taaacatat         360 acaccatata ctggagctgt gggtatggca gttcccatcc tgtctctggc tcccaaatga     420
ctgacttaag cataagtgct ctaaaaaact ttttgttccc tgctaggcag tgcttgtgct     480
ctcctttaat cccagcactc tttaattcca gcagttagga ggcggaggca aggcagatct     540
ctgtgagttc gaggccagcc tgatctacag agttccaaga gagccaaggc tacacagaga     600
aaccttgtct gggggggggg gggaaccaa aagagcattt attgcttttt cagaggatct     660
gggttggatt cccagagccc accttgaagc tcacaaccat ctgtaactct agtcacagcg     720
```

-continued

| | |
|---|---|
| gatatatata tatatatatt tatagcctgg gaatggggca gtaagcggga tgtgaagtga | 780 |
| ataattaatt aattaattag ggggctggag agatgactca gcaggtaaga gcagtggctg | 840 |
| ctcttccaca ggtcctgagt tcaattccca gcaaccacat ggtggctcac aaccatctgt | 900 |
| aatgggattc tatgcccttt tctggtgtgt ctgaagacag ctgacatgca gtcatataaa | 960 |
| tagaataaat aaatctaaaa aaaaacccaa aacaaaacca tatattaaat agaaaaacgt | 1020 |
| atggaagaga aaaacaaga caaggagaaa tgccttttgt ttaacatcca tttcctgaac | 1080 |
| ctaatctcag tgtcttctcc cagctattgt cccttgtcca tgtcaccttc tcagggactg | 1140 |
| tcctacacct tgtcgtagat ggtttcttcc ctccctgatc ttctcaggac ctcagcctac | 1200 |
| cctcttgcct tatggagggt ctcacccagt cagggcctga acccctcacc agcctcatct | 1260 |
| gcctgggtcc tgccttagcc tccttgctgg ggtctggagc ctccatcctt gccttctaca | 1320 |
| gtttgccttt cttcatgtct gactgagtgg tcgttccctt acctgaagcc ctcatggctc | 1380 |
| cccagtgtct ggttcaaacg ttttagcct gcattcagtg cctttcacaa cctggatctt | 1440 |
| actttatcta catatcccct ccatgcttca cacacacaca cccacacaca cacacacaca | 1500 |
| cacacacaca cacagactct ctaactttct tcactctcat atgcctgtag gtatgtccca | 1560 |
| cttctgaact cccaaggtca accattaaaa tctcactcag tccaccctgt ccgtgcttct | 1620 |
| ccaggattcc ggtcagcggg tgggggaggg gtcccagcct ggtacccccac ccctccatt | 1680 |
| ccagcctggg actcaggtct ctaacaacag aatcaaagcc acttagcaac gctggaaccc | 1740 |
| attcagggg gcctgagccc cctcatccca agccaagagg gctttggggg aggggtgcag | 1800 |
| cccctggtag actcactgtg tggccaaggg ggtcaagggg cgtcagggag acagggctg | 1860 |
| aactcatata aggagagaca cgagtgtggt tatcttcccc ctgctaggag gactagctag | 1920 |
| gggccatcat cagggtggga ggtctaggca accaagccag ttgttgtaaa ggcagagtag | 1980 |
| tgactggcag ccaaggtacc atggccacca tccagtcaga gactgactgc tacgacatca | 2040 |
| ttgaagttct gggcaagggc acttttggag aggtggccaa gggctggcgt cggagtacag | 2100 |
| gtgaaatggt ggccatcaag atcctgaaga acgatgcgta ccgaagccgc atcatcaaga | 2160 |
| atgagctgaa gctgctgcgc tgcgtgcgag gcctggaccc tgacgaggcc cacgttatcc | 2220 |
| gcttccttga gttcttccac gatgccctca agttctacct ggtcttcgag cttttggagc | 2280 |
| aaaacctctt tgagttccag aaagagaaca acttcgcacc ccttcctgcc aggcacatcc | 2340 |
| gcacggtcac actgcaggta ctaagagcgc tggcccggct caaggaactg gccatcatcc | 2400 |
| acgctgacct caagcctgaa acattatgt tggtagacca gacccgctgc cccttcaggg | 2460 |
| tcaaggtgag tgaggctgcc tgggaaatgg cttttgcttag ttcttggatg ctctgctaac | 2520 |
| acatgggtct ccctagtcag ttccgtgacg cagctccggg tgtccctgaa ccccaagctg | 2580 |
| cccctccttg ctgctctctg gctgtcttct gtatcccatc ccaattcttg ctttgttttg | 2640 |
| ttttgttttc gagacagagt cgatgtgca caggctggcc ttgaactcac tgtgtagctg | 2700 |
| aggacgactt gaactcatgg cctatctgcc ctccctgcct ccacgaccta agtgctagtg | 2760 |
| gtcacctaag tcaccacagc cagctcgctt tgttgtgttt tgtttttga agacaggatc | 2820 |
| tcagggagtc caggctggtc tggaatttga gtgggtttcc cttctcaagt accgggatta | 2880 |
| caggcattca ccatcttacc tggcttctcc atctcaactc tgaggtcctt tctatcgaag | 2940 |
| actggaggtc ttctgtgcct cccctctagg tcctgagtct gcccaaccct gcccgtttgg | 3000 |
| cttacttctt ctggctcagg tctgggcctc gtgggtctgg cattctagtg ggggagatgg | 3060 |
| tagcagggta agaagtaaag cgtgttgtgg atgtgagacc agagaaaaca ggagagagag | 3120 |

```
gctgggaact gctcagacat gggaagtggt agacagggag gtcacacttc aggaggtctt      3180
gaggggaaga gaaggccatg gagaagggat gagtttccag gatgaaggag gagccagcac      3240
aaaggctcga ggtaggagca tgtctaagta ttctagcaac acacagggga gttctgtgca      3300
gttgaagcac aaatgatggg gagcaaagag ggagaaaagg acaccaagga ggtaggggtg      3360
gggttgcaca aatcctcata ggcacagtca agattggttt tgttttggta tgtatatctc      3420
cctccatggt ttcacaatgt atccctggct ggccttgaac ttactatgta gacgaggcag      3480
gcttcaaact catggcagat cctcctgcct ctgcctccca acaatggac tcaaagttac       3540 acaccaacac gctaggcttg cagacgaatt cagagcagca ggatgggctc tgacttaggg      3600
gctcatcttg gggggaagta ggaccaagaa agcagatggg gtgatccaag aggagtccca      3660
ggtaaaagat gtaactgggg cattcgtgga ttccgggcag attttagagc tagagacaac      3720
agaattagaa ttgattgatg ggtttcacag tgtgagggag aggggctggg gagatgctca      3780
gatagtaatg tccccgctga acaagcatgg aaacctcagt gcagacccct accatcccca      3840
tgaaaagacg gctgtggcag cacacctgta atatcagtgt aggggaggta gagacaggag      3900
gattcctaga gcttgatggc cagccagtct agccaatcag caggctcggg gttccaggag      3960
gggagggatc ttatctcata tataaaagtt agagagcgat agaagacatg cgatgcatgt      4020
gtgatgacac acatgtgcac acgcatacaa acatctacac atacatttag aaaaagaagg      4080
gccagcaaga tggctcagcc agttcaggtg cttgctgcca agcctaagga cttgagtcca      4140
gtagccagaa cccatatggt gggagcagag aactgacttc ctgactctgg aagttgtcct      4200
ctgacctcta cacatatacc actgcatttg catatccctc cccccactaa attcagttta      4260
aaaatgaaaa agtgtgaggg gcagctgggc attgtgcag cctcctatat ttccagcact       4320
gcacaagtgg aggcaggagg attaaaaatt caaggtcatc cttggctgtt aaacaagttc      4380
aaggtcagct tgcactttca aggtctgtct tgcactacct gagacctcat ctttaaagaa      4440
aagatgtgag agaggctgag tgggctcaag ttgagccaga gcctgcggat ctagacaaat      4500
gcaaggtggt tctagcctct gttcctgttc ctgaccctgg gtgggcacct aagctgtccc      4560
ttgttccccc tagatcccac ttctgctgag cctctgtctg ggcctcatca acctactcag      4620
acacccctct tgtgcctcct ccatcagagc tcagactcct ctgcctgctt atctgtcagc      4680
aaggcactgg tgatgactgg gctggcagca gcacccaagg gcagggctgg accaaagctg      4740
cctatactgt gcctctcccc gtgccccact gaatgttaga gacacagaga caggaagaga      4800
tgggtatttc tgccctgttg gatggaagga cagtgagccg agaggaagag agctctgtag      4860
acctaacagg gctcacacag cacctggggg tcgctggcac ccttcaagtg ctttcagaat      4920
gaagggactc cacatacact ggctcaactc tcagtgtcac tgaagtccta ggggcgttg      4980 agtccagact aataactatt tcatgattgg ccttgtgtgc atggaggtaa gaggtgacta      5040
aatggataaa taaatgaata aataaacgca gggaagctgc agcctgccct gagtcacagg      5100
aattcacagt gagactggaa gagcgccacc tggtggcgag aggaaaggca ggcgcctacc      5160
catggcccat ggattaccaa gaagcttggt aattacaagc tgaaggcctt cggggtgttg      5220
tcagtgtctg acggtaaaga tcttagagga cttggtttta ggatggtacc tttccagtcc      5280
atgacacaga aacaaagaca gagacactgg gagatgagga ttagctgaag aggcagtggg      5340
agagagagag agaaagagag agagagagac agagccactg ggtggtggca gcacatgctt      5400
ttaatatcag cacttgggag gtacaggtag aggtggattt ctgagttcta ggccatcctg      5460
```

```
gtctacagag tgagtttaag gaccaccagg gttacacaga gaaaccctgt cttgaaaaac    5520
aaatacacac acatacacac acacacacac atacatatac atacatatat atatgagaag    5580
ggagccagac ctggtgaaac atgcctataa tcccagatta ttgtacctc tacatttcct    5640 ctcttatgaa tgaccctgcc tgaagttcaa tctctaggac catggaagac agacacacaa    5700
atcaaaggga ggacaatact gattggtgta aatgcctac tagttccagg cctccagaga     5760
cacagccttg aataaaatac aaagctcttg ttgtcatggg actggagttc tattttttt     5820 ttcatttatt ttcttttat atgtgagtgc aaatgtatgg atgtatggtg ttccaagagg     5880
tcagagggct ttggattccc cctgaaacta gagttccaga caggtgtgag ctgccatgtg    5940
ggtgctggga gccaaacctg gattccctgc aagagcagcc agtgctcttt accactgagc    6000
catctctcag gcctagcggg ttaagtgctt gctgcacaca agcagaagag cctaaattca    6060
gatccccagg gaccccataa aagctgggct tgactttata atcccagggc tgagggatg     6120 taagggaaga caagaagatc ctgagggctc agtggcccgg ctatcttgcc aaagttgtga    6180
gtttcaggtt cactaagaga ccttgcctca caaaataagg ttacagcggt agaggaagat    6240
agaggacctt tggccttata catgcacaca tgggtgatga cacccacata tgcctataac    6300
acctccaaca cacacaacac ccccctcag ggaaatatat atatagtatg tgaaatgatg    6360
ttaaaatcat agctgggagc tgggtgaaag aacaggaatt caaggacatc cttggctaca    6420
taaccaggtt gaagccagcc tgggctatat gagaccctgt ctcaaaacta accaacaaaa    6480
aggacagagg atatgggtga atacttgcct actatgcact acagcagggg gagggtccca    6540
actattatag gcacaagttc aagcagagaa tcagacagag ccagacctga cacctgacac    6600
agaagcaata gctagaggac agaggcaggg tcattcataa gaaggaagt gtagaaggta     6660 caagagctag gcagacacag gagatacaca gggatgagtc ccaggagggg cctatcctgt    6720
catctctacc actccaccaa cccagctgcc ctgtgctcca tccctctgt cctccatagg     6780 tgatcgactt tggctcggcc agcatattca gtgaggtacg ctatgtgaag gagccttaca    6840
tccagtcccg cttctacagg gccccagaga tcctgctggg gctgcccttc tgtgagaagg    6900
tggacgtgtg gtctctgggc tgtgtcatgg ccagctacac tctgggctgg cctctctacc    6960
caggcaacaa tgagtatgac caggtgcgct acatctgtga gacccagggc ttacccaagc    7020
cccatttgct gcatgcggct cgcaaggctc accacttctt caagcgtaac ccccacccg     7080 atgccaccaa cccctggcag ctgaagtcct ctgctgacta cctagctgag accaaggtat    7140
gggggagcat gcagggtgaa gacagcctgt gctgggggt ggggacgata ctatatcgcc     7200
atgtctcttt ggctggactg agggtctagg tgaaatgtgg agcctgagtt aggtcacata    7260
tcctccctgt agcagtggga gagtgatgga ttggaaatca agaatctggt atgagggga     7320 cgactggaga attgaaatag caagagaact tccagtcata tcatgggcag aagtcagggg    7380
gtgattttga gtctagatac atggcaggct ggtgtccccc acccccacc aggtacgtcc     7440 tctggagcgc cgcaagtaca tgctcaaatc cttggaccag attgagacag tgaatggtgg    7500
tggagctgtg agccggctga gttttccaga ccggggaggcc ctggcggaac acgcagacct    7560
caagagcatg gtggagctga tcaaacgcat gctgacatgg gagtcgcacg aacgcatcag    7620
tcccagtgcg gccctgcgtc accccttcgt gtccatgcag cagctgcgga gtgcccacga    7680
ggccacccgc tactaccagc tgtcgctcag aggctgtcgg ctgtccctgc aggtggatgg    7740
caagccaccc ccacctgtca tagccagcgc agaggacggg cctccctact accgcctggc    7800
tgaggaggag gagactgcag gcctgggtgg tgtgacaggc agtgggtcct tcttcaggga    7860
```

-continued

```
ggacaaggct ccgggaatgc agagggccat cgaccagctc gatgacctga gtctgcaaga    7920
ggccagacgg gggctgtgga gcgacacacg ggccgacatg gtctctgaca tgctggttcc    7980
actcaaagtg gccagtacca gccaccgagt ccctgactca ggcccagagc ctatcctggc    8040
cttctacggc agccgattga ccggccgcca taaggcccgc aaggcccag caggctccaa     8100 atctgactcc aacttcagta acctcattcg gctgagccag gcctcacctg aggatgccgg    8160
gccctgtcgg ggcagtggct gggaggaagg agaaggccgc acgacctcca cagagccgtc    8220
tgtcatccca caacgggaag gagatgggcc tggcatcaaa gacaggccca tggatgccga    8280
ggtaagtggg gtgcagactg gcacccagag cttaattgac ggtgcacagg tgacagggcc    8340
gtgcttctta cagctgcagc atctgtcatc tcaacacggg cccaagattc agtaaatact    8400
gacctcctgc acaaggtggc agggctcagc tcacaccaat accctcagga ctggacaagg    8460
ctgatacaaa ctctaattaa ggatggcaca gaaaacaggc acctagtgat gggctggtta    8520
agaaatgggt gaggtgctgg gtggtgtggt acattatctg taatcccggg gagctcaaac    8580
aggagggtca tctcaaggtc aagtctagtt tgggtcataa caagacccta tctcaaaaag    8640
caaacagtaa tattccctcc ctaccaaaag ggctacagat ttagttgtgc agtagagttc    8700
ttgcctagta tctaccagtg agagaatggg gactctccta cacagagtgc ttaccaatgt    8760
gaggggctgg gggtgtggct cagtggtaga gcccctgcct agaatccctc agtgagggac    8820
tgggggcatg gctcagtggt agagcccctg cctagaatcc cccagtgagg ggctgggggc    8880
gtggctcagt ggtagagccc ctgcctagaa tcccccagtg aggggctggg ggtgtggctc    8940
agtggtagag cccctgccta gaatccccca gtgaggggct gggacgtgg tccagaggca    9000 gagcatttgc ctggtctgcc aaggcttcca tccctaatac ctttgcaatg tgggaaggcc    9060
tacacaggga gtgagggcct tcatacctgc tcactccttc cagtagacag gtacacacct    9120
cagcaggtac ccataattct tgctgatatt cttttctttt cccctccaca gaggccaggc    9180
cctgagctct ttgatcccag cagctgtcct ggagagtggc tgagtgagcc agaatggacc    9240
ctagagggca tccgggggtc tcgagctcaa gggctcccag ctcaccatcc ccaccccac    9300 gggccaccca ggaccaccag ctttctgcag catgttggag ggcaccactg atggggactc    9360 accctatcg tttcatgggg tctgagctag ctgggctggc gttcccctc ttgatccgaa     9420 atggcacctt agagccatcc tctgaaccta cagattattc ttacagaaaa atagaaatcc    9480
agatgttcct attccctgc ccctggcaca tgcctgtatc ccaccctaaa tgttggaggt     9540
cgtcagggtc tggcctgagg ccctgaggcc agtgagttgg gaagaggctg caccctggtg    9600
gccatgactg tgcctgggcc tgcctgcctc tgtgtatttc aataaataac tgttccaaac    9660
cctgctcctg cctgttacca ctgggtgaac ctgtaccacc catattgggc caaggggca     9720 cccagggcct gcctcgcccc tgctgtgact ggttggccac tggctgaacc cagaggctca    9780
gtcagtggca gggaaaagct gcgcagggca cagtaacctg tgctctatat acactaaatt    9840
aaacctggta tggggcagtg ggtttgtaat tctaagcact caggagactg aggcaggaga    9900
attacaaggt caagaccagt ttgggcttat gatgagacct tgtcaacaca ggggttgtag    9960
gggagatggg atgaggcaag ggcctggctc cttgggaatc taccccttagg atgttcacat  10020 gttggacaag gaccccctggc ttcgtcctct atgtctgtga tggacaggcc atgcgctcgc   10080
tcgctcatgc tctggacatg ttaagtgtaa acacactggt aggaataaat tcagacttcg   10140
cacatgctgt gttgttcaca tacgcacatg ctccggtgtt cagatatgtt agtccagctg   10200
```

-continued

```
ccacttgggc cggccttat tcccccccac ccccaccccc acccaccac ctcccattcc    10260 catcccaac ggccgtaaat ggcattcagc agtggttcta cccgcactgc tctgtggagc    10320
atactcggta caaacatgct ggttctacgc atgctcagcc catgcttgcc agtgcggtca    10380
cacactgcat gcccagccca cgccagcctt cgtgcgcact gcatgctgtc accagcagaa    10440
gtccataccc cctccccct aacaaacata ccatctcata ccactcagtt aagcacaggc    10500
tatacagaca attatttact tataatcttg gccctttggg ggtgggccaa aggtctgggc    10560
ccagcatgca ccccacttc tttggggccc aatccccagc tctgctaggt ccacaggggc    10620
cagagtgtca ggccagtggc ggtggaggta gcagcaggag tatagtggag agtacagagc    10680
cacacgggat agacagaggc aagggcatgg ggacagtaac caggacccag agctgagtcc    10740
aaggaggcct ggaaggcttt gacctgtccg tcgggctgag cctcaaagca ggcggcaggc    10800
attgcccaca ctgttggctg aggtgtcgag atcgtggctg tatggggatt cccagtctct    10860
caggaaaaca gcctccagct gactgcgcaa gccaccatgc ccgttctgtg tcaccagcag    10920
ggaggtgcct gctgtctccg tgaagtagct tccagaccag ttggaggttc ctgggagcaa    10980
ggggtggagt gagggtctga tgggtggcca gaccctagtg cccaggcctt tcctttgata    11040
tggtactggg ggcacttacc aatgtatgag gcacgttcag tcaccatgta cttgttgtgg    11100
ttgacacggg catagggat tcgggcctgg gactcatccg tagggaccac aaacagtttc    11160
tgcaggggag aggaggatgg tgaggtgggg gctcaaggtg caggtggggt gtctctgaga    11220
agtcctggga tggtaggatg gcatgtgaat ggtatctcca aaaggcactt ggctgcttct    11280
ctgggaaggg tggatcctgg gaccaaaata ggtcccaggg cagctgggcc tcggtgaaca    11340
cgagctgagg c                                                        11351
```

<210> SEQ ID NO 7
<211> LENGTH: 1851
<212> TYPE: DNA
<213> ORGANISM: Macaca fascicularis
<220> FEATURE:
<221> NAME/KEY: CDS
<222> LOCATION: (1)..(1848)

<400> SEQUENCE: 7

```
atg gct acc acc cag tca gag acc gac tgc tac gac atc atc gag gtc     48
Met Ala Thr Thr Gln Ser Glu Thr Asp Cys Tyr Asp Ile Ile Glu Val
1               5                   10                  15 ttg ggc aag ggg acc ttc ggg gag gta gcc aag ggc tgg cgg cgg agc     96
Leu Gly Lys Gly Thr Phe Gly Glu Val Ala Lys Gly Trp Arg Arg Ser
            20                  25                  30 acg ggc gag atg gtg gcc atc aag atc ctc aag aac gac gcc tac cgc    144
Thr Gly Glu Met Val Ala Ile Lys Ile Leu Lys Asn Asp Ala Tyr Arg
        35                  40                  45 aac cgc atc atc aag aat gag ctg aag ctg ctg cac tgc atg cga ggc    192
Asn Arg Ile Ile Lys Asn Glu Leu Lys Leu Leu His Cys Met Arg Gly
    50                  55                  60 ctg gac cct gag gag gcc cac gtc atc cgc ttc ctc gag ttc ttc cac    240
Leu Asp Pro Glu Glu Ala His Val Ile Arg Phe Leu Glu Phe Phe His
65                  70                  75                  80 gac gcc ctc aag ttc tac ctg gtc ttc gag ctg ctg gag caa aac ctt    288
Asp Ala Leu Lys Phe Tyr Leu Val Phe Glu Leu Leu Glu Gln Asn Leu
                85                  90                  95 ttt gag ttc cag aag gag aac aac ttc gcg ccc ctc cct gcc cgc cac    336
Phe Glu Phe Gln Lys Glu Asn Asn Phe Ala Pro Leu Pro Ala Arg His
            100                 105                 110
```

```
atc cgt aca gtc acc ctg cag gtg ctc aga gcc ctg gcc cgg ctc aag      384
Ile Arg Thr Val Thr Leu Gln Val Leu Arg Ala Leu Ala Arg Leu Lys
        115                 120                 125 gag ctg gca atc atc cac gct gat ctc aag cct gag aat atc atg ctg      432
Glu Leu Ala Ile Ile His Ala Asp Leu Lys Pro Glu Asn Ile Met Leu
    130                 135                 140 gtg gac cag acc cgc tgc ccc ttc agg gtc aag gtg att gac ttc ggc      480
Val Asp Gln Thr Arg Cys Pro Phe Arg Val Lys Val Ile Asp Phe Gly
145                 150                 155                 160 tct gcc agc att ttc agc gag gtg cgc tac gtg aag gag cca tac atc      528
Ser Ala Ser Ile Phe Ser Glu Val Arg Tyr Val Lys Glu Pro Tyr Ile
                165                 170                 175 cag tcg cgc ttc tac cgg gcc ccc gag atc ctg ctg ggg ctg ccc ttc      576
Gln Ser Arg Phe Tyr Arg Ala Pro Glu Ile Leu Leu Gly Leu Pro Phe
            180                 185                 190 tgc gag aag gtg gac gtg tgg tcc ctg ggc tgt gtc atg gct gag ctg      624
Cys Glu Lys Val Asp Val Trp Ser Leu Gly Cys Val Met Ala Glu Leu
        195                 200                 205 cac ctg ggc tgg ccc ctc tac ccc ggc aat aac gag tac gac cag gtg      672
His Leu Gly Trp Pro Leu Tyr Pro Gly Asn Asn Glu Tyr Asp Gln Val
    210                 215                 220 cgc tac atc tgc gaa acc cag ggc ctc ccc aag ccg cac ctg ctg cac      720
Arg Tyr Ile Cys Glu Thr Gln Gly Leu Pro Lys Pro His Leu Leu His
225                 230                 235                 240 gcc gcc cgc aag gcc cac cac ttc ttt aag cgc aac ccc cac cct gac      768
Ala Ala Arg Lys Ala His His Phe Phe Lys Arg Asn Pro His Pro Asp
                245                 250                 255 gcc gcc aac ccc tgg cag ctc aag tcc tcg gct gac tac ctg gcc gag      816
Ala Ala Asn Pro Trp Gln Leu Lys Ser Ser Ala Asp Tyr Leu Ala Glu
            260                 265                 270 acg aag gtg cgc cca ctg gag cgc cgc aag tat atg ctt aag tcc ttg      864
Thr Lys Val Arg Pro Leu Glu Arg Arg Lys Tyr Met Leu Lys Ser Leu
        275                 280                 285 gac cag atc gag aca gtg aat ggt ggc agt gtg gcc agt cgg ctg acc      912
Asp Gln Ile Glu Thr Val Asn Gly Gly Ser Val Ala Ser Arg Leu Thr
    290                 295                 300 ttc ccc gac cgg gag gca ctg gca gag cac gcc gac ctc aag agc atg      960
Phe Pro Asp Arg Glu Ala Leu Ala Glu His Ala Asp Leu Lys Ser Met
305                 310                 315                 320 gtg gag ctg atc aaa cgc atg ctg acc tgg gaa tca cat gaa cgc atc     1008
Val Glu Leu Ile Lys Arg Met Leu Thr Trp Glu Ser His Glu Arg Ile
                325                 330                 335 agc ccc agt gct gcc ctg cgc cac ccc ttc gtg tcc atg cag cag ctg     1056
Ser Pro Ser Ala Ala Leu Arg His Pro Phe Val Ser Met Gln Gln Leu
            340                 345                 350 cgc aat gcc cac gag acc acc cac tac tac cag ctc tcg ctg cgc agc     1104
Arg Asn Ala His Glu Thr Thr His Tyr Tyr Gln Leu Ser Leu Arg Ser
        355                 360                 365 tac cgc ctc tcg ctg cag gtg gag ggc aag ccc ccc gcg cct gtc gtg     1152
Tyr Arg Leu Ser Leu Gln Val Glu Gly Lys Pro Pro Ala Pro Val Val
    370                 375                 380 gct gca gaa gat ggg acc ccc tac tac cgt ctg gct gag gag aag gag     1200
Ala Ala Glu Asp Gly Thr Pro Tyr Tyr Arg Leu Ala Glu Glu Lys Glu
385                 390                 395                 400 gct gcg ggc atg ggc agt gtg gcc agc agc agc ccc ttc ttc cga gag     1248
Ala Ala Gly Met Gly Ser Val Ala Ser Ser Ser Pro Phe Phe Arg Glu
                405                 410                 415 gag aag gca cca ggt atg caa aga gcc atc gac cag ctg gac gac ctg     1296
Glu Lys Ala Pro Gly Met Gln Arg Ala Ile Asp Gln Leu Asp Asp Leu
            420                 425                 430
```

```
agt ctg cag gag gct ggg cat ggg ctg tgg ggt gag acc tgc acc gat    1344
Ser Leu Gln Glu Ala Gly His Gly Leu Trp Gly Glu Thr Cys Thr Asp
        435                 440                 445 gtg gtc tcc gac atg atg gcc ccc ctc aag gca gcc atc act ggc cgc    1392
Val Val Ser Asp Met Met Ala Pro Leu Lys Ala Ala Ile Thr Gly Arg
450                 455                 460 cac atg ccc gac tca ggc ccc gag ccc atc ctg gcc ttc tat agc agc    1440
His Met Pro Asp Ser Gly Pro Glu Pro Ile Leu Ala Phe Tyr Ser Ser
465                 470                 475                 480 cgc ctg gca ggc cgc cac aag gcc cgc aag cca cct gcg ggt tcc aaa    1488
Arg Leu Ala Gly Arg His Lys Ala Arg Lys Pro Pro Ala Gly Ser Lys
                485                 490                 495 tcc gac tcc aac ctc agc aac ctc atc cgg ctg agc cag gtc tcg cct    1536
Ser Asp Ser Asn Leu Ser Asn Leu Ile Arg Leu Ser Gln Val Ser Pro
            500                 505                 510 gag gat gac agg ccc tgc cgg ggc agc agc tgg gag gaa gga gag cat    1584
Glu Asp Asp Arg Pro Cys Arg Gly Ser Ser Trp Glu Glu Gly Glu His
        515                 520                 525 ctc ggg gcc tct gct gag cca ccg gcc atc ctg cag cga gat ggg gat    1632
Leu Gly Ala Ser Ala Glu Pro Pro Ala Ile Leu Gln Arg Asp Gly Asp
530                 535                 540 ggg ccc aac att gac aac atg acc atg gag gct gag agg cca gac cct    1680
Gly Pro Asn Ile Asp Asn Met Thr Met Glu Ala Glu Arg Pro Asp Pro
545                 550                 555                 560 gag ctc ttc gac ccc agc agc tgt ccc gga gaa tgg ctg agt gag cca    1728
Glu Leu Phe Asp Pro Ser Ser Cys Pro Gly Glu Trp Leu Ser Glu Pro
                565                 570                 575 gac tgg acc ctg gag ggc gtc agg ggc cca cgg gct cag ggg ctc cca    1776
Asp Trp Thr Leu Glu Gly Val Arg Gly Pro Arg Ala Gln Gly Leu Pro
            580                 585                 590 ccc cgc cgc tcc cac cag cat ggt ccg ccc cgg ggg gcc acc agt ttc    1824
Pro Arg Arg Ser His Gln His Gly Pro Pro Arg Gly Ala Thr Ser Phe
        595                 600                 605 ctc cag cat gtc acc ggg cac cac tga                                1851
Leu Gln His Val Thr Gly His His
    610                 615

<210> SEQ ID NO 8
<211> LENGTH: 616
<212> TYPE: PRT
<213> ORGANISM: Macaca fascicularis

<400> SEQUENCE: 8

Met Ala Thr Thr Gln Ser Glu Thr Asp Cys Tyr Asp Ile Ile Glu Val
1               5                   10                  15

Leu Gly Lys Gly Thr Phe Gly Glu Val Ala Lys Gly Trp Arg Arg Ser
                20                  25                  30

Thr Gly Glu Met Val Ala Ile Lys Ile Leu Lys Asn Asp Ala Tyr Arg
            35                  40                  45

Asn Arg Ile Ile Lys Asn Glu Leu Lys Leu Leu His Cys Met Arg Gly
        50                  55                  60

Leu Asp Pro Glu Glu Ala His Val Ile Arg Phe Leu Glu Phe Phe His
65                  70                  75                  80

Asp Ala Leu Lys Phe Tyr Leu Val Phe Glu Leu Leu Glu Gln Asn Leu
                85                  90                  95

Phe Glu Phe Gln Lys Glu Asn Asn Phe Ala Pro Leu Pro Ala Arg His
            100                 105                 110

Ile Arg Thr Val Thr Leu Gln Val Leu Arg Ala Leu Ala Arg Leu Lys
```

```
            115                 120                 125
Glu Leu Ala Ile Ile His Ala Asp Leu Lys Pro Glu Asn Ile Met Leu
    130                 135                 140
Val Asp Gln Thr Arg Cys Pro Phe Arg Val Lys Val Ile Asp Phe Gly
145                 150                 155                 160
Ser Ala Ser Ile Phe Ser Glu Val Arg Tyr Val Lys Glu Pro Tyr Ile
                    165                 170                 175
Gln Ser Arg Phe Tyr Arg Ala Pro Glu Ile Leu Leu Gly Leu Pro Phe
                180                 185                 190
Cys Glu Lys Val Asp Val Trp Ser Leu Gly Cys Val Met Ala Glu Leu
            195                 200                 205
His Leu Gly Trp Pro Leu Tyr Pro Gly Asn Asn Glu Tyr Asp Gln Val
    210                 215                 220
Arg Tyr Ile Cys Glu Thr Gln Gly Leu Pro Lys Pro His Leu Leu His
225                 230                 235                 240
Ala Ala Arg Lys Ala His His Phe Phe Lys Arg Asn Pro His Pro Asp
                    245                 250                 255
Ala Ala Asn Pro Trp Gln Leu Lys Ser Ser Ala Asp Tyr Leu Ala Glu
                260                 265                 270
Thr Lys Val Arg Pro Leu Glu Arg Arg Lys Tyr Met Leu Lys Ser Leu
            275                 280                 285
Asp Gln Ile Glu Thr Val Asn Gly Gly Ser Val Ala Ser Arg Leu Thr
    290                 295                 300
Phe Pro Asp Arg Glu Ala Leu Ala Glu His Ala Asp Leu Lys Ser Met
305                 310                 315                 320
Val Glu Leu Ile Lys Arg Met Leu Thr Trp Glu Ser His Glu Arg Ile
                    325                 330                 335
Ser Pro Ser Ala Ala Leu Arg His Pro Phe Val Ser Met Gln Gln Leu
                340                 345                 350
Arg Asn Ala His Glu Thr Thr His Tyr Tyr Gln Leu Ser Leu Arg Ser
            355                 360                 365
Tyr Arg Leu Ser Leu Gln Val Glu Gly Lys Pro Pro Ala Pro Val Val
    370                 375                 380
Ala Ala Glu Asp Gly Thr Pro Tyr Tyr Arg Leu Ala Glu Glu Lys Glu
385                 390                 395                 400
Ala Ala Gly Met Gly Ser Val Ala Ser Ser Pro Phe Phe Arg Glu
                    405                 410                 415
Glu Lys Ala Pro Gly Met Gln Arg Ala Ile Asp Gln Leu Asp Asp Leu
                420                 425                 430
Ser Leu Gln Glu Ala Gly His Gly Leu Trp Gly Glu Thr Cys Thr Asp
            435                 440                 445
Val Val Ser Asp Met Met Ala Pro Leu Lys Ala Ile Thr Gly Arg
    450                 455                 460
His Met Pro Asp Ser Gly Pro Glu Pro Ile Leu Ala Phe Tyr Ser Ser
465                 470                 475                 480
Arg Leu Ala Gly Arg His Lys Ala Arg Lys Pro Pro Ala Gly Ser Lys
                    485                 490                 495
Ser Asp Ser Asn Leu Ser Asn Leu Ile Arg Leu Ser Gln Val Ser Pro
                500                 505                 510
Glu Asp Asp Arg Pro Cys Arg Gly Ser Ser Trp Glu Glu Gly Glu His
            515                 520                 525
Leu Gly Ala Ser Ala Glu Pro Pro Ala Ile Leu Gln Arg Asp Gly Asp
    530                 535                 540
```

-continued

Gly Pro Asn Ile Asp Asn Met Thr Met Glu Ala Glu Arg Pro Asp Pro
545                 550                 555                 560

Glu Leu Phe Asp Pro Ser Ser Cys Pro Gly Glu Trp Leu Ser Glu Pro
            565                 570                 575

Asp Trp Thr Leu Glu Gly Val Arg Gly Pro Arg Ala Gln Gly Leu Pro
        580                 585                 590

Pro Arg Arg Ser His Gln His Gly Pro Pro Arg Gly Ala Thr Ser Phe
    595                 600                 605

Leu Gln His Val Thr Gly His His
    610                 615

<210> SEQ ID NO 9
<211> LENGTH: 21
<212> TYPE: DNA
<213> ORGANISM: Homo sapiens

<400> SEQUENCE: 9
aaccgcatca tcaagaacga g                                         21

<210> SEQ ID NO 10
<211> LENGTH: 21
<212> TYPE: DNA
<213> ORGANISM: Homo sapiens

<400> SEQUENCE: 10
gtcagggaag gttagccgac t                                         21

<210> SEQ ID NO 11
<211> LENGTH: 23
<212> TYPE: DNA
<213> ORGANISM: Homo sapiens

<400> SEQUENCE: 11
agacgaaggt gcgcccattg gag                                       23

<210> SEQ ID NO 12
<211> LENGTH: 23
<212> TYPE: DNA
<213> ORGANISM: Homo sapiens

<400> SEQUENCE: 12
ctggcggatc cgaagtcaat cac                                       23

<210> SEQ ID NO 13
<211> LENGTH: 521
<212> TYPE: DNA
<213> ORGANISM: Homo sapiens

<400> SEQUENCE: 13
acgagaccac ccactactac cagctctcgc tgcgcagcta ccgcctctcg ctgcaagtgg    60
aggggaagcc ccccacgccc gtcgtggccg cagaagatgg gaccccctac tactgtctgg   120
ctgaggagaa ggaggctgcg ggtatgggca gtgtggccgg cagcagcccc ttcttccgag   180
aggagaaggc accaggtatg caaagagcca tcgaccagct ggatgacctg agtctgcagg   240
aggctgggca tgggctgtgg ggtgagacct gcaccaatgc ggtctccgac atgatggtcc   300
ccctcaaggc agccatcact ggccaccatg tgcccgactc gggccctgag cccatcctgg   360
ccttctacag cagccgcctg gcaggccgcc acaaggcccg caagccacct gcgggttcca   420
agtccgactc caacttcagc aacctcattc ggctgagcca ggtctcgcct gaggatgaca   480

```
ggccctgccg gggcagcagc tgggaggaag gagagcatct c                    521

<210> SEQ ID NO 14
<211> LENGTH: 20
<212> TYPE: DNA
<213> ORGANISM: Homo sapiens

<400> SEQUENCE: 14
acgagaccac ccactactac                                            20

<210> SEQ ID NO 15
<211> LENGTH: 20
<212> TYPE: DNA
<213> ORGANISM: Homo sapiens

<400> SEQUENCE: 15
gagatgctct ccttcctccc                                            20

<210> SEQ ID NO 16
<211> LENGTH: 1851
<212> TYPE: DNA
<213> ORGANISM: Rattus norvegicus
<220> FEATURE:
<221> NAME/KEY: CDS
<222> LOCATION: (1)..(1848)

<400> SEQUENCE: 16 atg gcc acc atc cag tca gag act gac tgt tac gac atc att gaa gtc    48
Met Ala Thr Ile Gln Ser Glu Thr Asp Cys Tyr Asp Ile Ile Glu Val
1               5                   10                  15 ctg ggc aag ggc act ttt gga gag gtg gcc aag ggc tgg cgt cgg agt    96
Leu Gly Lys Gly Thr Phe Gly Glu Val Ala Lys Gly Trp Arg Arg Ser
            20                  25                  30 aca gga gaa atg gtg gcc atc aag atc ttg aag aac gac gcg tac cga   144
Thr Gly Glu Met Val Ala Ile Lys Ile Leu Lys Asn Asp Ala Tyr Arg
        35                  40                  45 agc cgt atc atc aag aat gag ttg aag ctg ctg cgc tgt gta cga ggc   192
Ser Arg Ile Ile Lys Asn Glu Leu Lys Leu Leu Arg Cys Val Arg Gly
    50                  55                  60 ctg gac ccc gac gag gcc cac gtc atc cgc ttc ctt gaa ttc ttc cat   240
Leu Asp Pro Asp Glu Ala His Val Ile Arg Phe Leu Glu Phe Phe His
65                  70                  75                  80 gat gcc ctc aag ttc tac ctg gtc ttt gag cta ttg gag caa aac ctc   288
Asp Ala Leu Lys Phe Tyr Leu Val Phe Glu Leu Leu Glu Gln Asn Leu
                85                  90                  95 ttt gag ttc cag aaa gag aac aac ttc gca ccc ctc cct gcc agg cac   336
Phe Glu Phe Gln Lys Glu Asn Asn Phe Ala Pro Leu Pro Ala Arg His
            100                 105                 110 atc cga act gtc aca ctg cag gtc cta aga gcg ctg gcc cgg ctc aag   384
Ile Arg Thr Val Thr Leu Gln Val Leu Arg Ala Leu Ala Arg Leu Lys
        115                 120                 125 gag ttg gct atc atc cat gct gac ctc aag cca gaa aac att atg ttg   432
Glu Leu Ala Ile Ile His Ala Asp Leu Lys Pro Glu Asn Ile Met Leu
    130                 135                 140 gta gat cag acc cgc tgc ccc ttc agg gta aag gtg atc gac ttt ggc   480
Val Asp Gln Thr Arg Cys Pro Phe Arg Val Lys Val Ile Asp Phe Gly
145                 150                 155                 160 tcg gcc agc ata ttc agt gag gtg cgc tat gtg aag gag cct tac atc   528
Ser Ala Ser Ile Phe Ser Glu Val Arg Tyr Val Lys Glu Pro Tyr Ile
                165                 170                 175 cag tcc cgc ttc tac agg gcc cca gag atc ctg ttg ggg ttg ccg ttc   576
```

```
                Gln Ser Arg Phe Tyr Arg Ala Pro Glu Ile Leu Leu Gly Leu Pro Phe
                            180                 185                 190 tgc gag aag gtg gac gtg tgg tct ctg ggc tgt gtc atg gct gag tta      624
Cys Glu Lys Val Asp Val Trp Ser Leu Gly Cys Val Met Ala Glu Leu
            195                 200                 205 cac ctg ggc tgg cct ctc tac cca ggc aac aat gag tat gac cag gtg      672
His Leu Gly Trp Pro Leu Tyr Pro Gly Asn Asn Glu Tyr Asp Gln Val
        210                 215                 220 cgc tac atc tgt gag acc cag ggc tta ccc aag ccc cat ctg ctg cat      720
Arg Tyr Ile Cys Glu Thr Gln Gly Leu Pro Lys Pro His Leu Leu His
225                 230                 235                 240 gcg gcc cgc aag gct cac cac ttc ttc aag cgt aac ccc cac ccc gat      768
Ala Ala Arg Lys Ala His His Phe Phe Lys Arg Asn Pro His Pro Asp
                245                 250                 255 gcc acc aac ccc tgg cag ctc aag tcc tct gct gac tac cta gct gag      816
Ala Thr Asn Pro Trp Gln Leu Lys Ser Ser Ala Asp Tyr Leu Ala Glu
            260                 265                 270 acc aag gta cgc cca ctg gag cgc cgc aag tac atg ctc aaa tcc ttg      864
Thr Lys Val Arg Pro Leu Glu Arg Arg Lys Tyr Met Leu Lys Ser Leu
        275                 280                 285 gac caa att gag acg gtg aat ggt ggc ggc gct gtg aat cgg ttg agt      912
Asp Gln Ile Glu Thr Val Asn Gly Gly Gly Ala Val Asn Arg Leu Ser
290                 295                 300 ttt cca gac cgg gag gca ctg gcg gaa cac gcg gac ctc aag agc atg      960
Phe Pro Asp Arg Glu Ala Leu Ala Glu His Ala Asp Leu Lys Ser Met
305                 310                 315                 320 gtg gag ctg atc aaa cgc atg ctg aca tgg gag tct cac gag cgc atc     1008
Val Glu Leu Ile Lys Arg Met Leu Thr Trp Glu Ser His Glu Arg Ile
                325                 330                 335 agt ccc agc gcg gcc ctg cgc cac ccc ttc gtg tcc atg cag cag ctg     1056
Ser Pro Ser Ala Ala Leu Arg His Pro Phe Val Ser Met Gln Gln Leu
            340                 345                 350 cgt agt gcc cac gag gcc acc cgc tac tac cag ctg tcc ctc cga ggc     1104
Arg Ser Ala His Glu Ala Thr Arg Tyr Tyr Gln Leu Ser Leu Arg Gly
        355                 360                 365 tgt cgg ctg tcc ctg cag gtg gac ggc aag cca ccc cca cct gtc ata     1152
Cys Arg Leu Ser Leu Gln Val Asp Gly Lys Pro Pro Pro Pro Val Ile
370                 375                 380 gcc aac gca gag gac ggg cct ccc tac tac cgc ctg gct gag gag gag     1200
Ala Asn Ala Glu Asp Gly Pro Pro Tyr Tyr Arg Leu Ala Glu Glu Glu
385                 390                 395                 400 gag act gca ggc ctg ggt ggt gtg acc ggc agt ggg tcc ttc ttc agg     1248
Glu Thr Ala Gly Leu Gly Gly Val Thr Gly Ser Gly Ser Phe Phe Arg
                405                 410                 415 gag gac aag gct ccc gga atg cag aga gcc atc gac cag ctc gat gac     1296
Glu Asp Lys Ala Pro Gly Met Gln Arg Ala Ile Asp Gln Leu Asp Asp
            420                 425                 430 ctg agt ctg cag gag gcc cgc cgg ggg ctg tgg agc gac acg cgg gcc     1344
Leu Ser Leu Gln Glu Ala Arg Arg Gly Leu Trp Ser Asp Thr Arg Ala
        435                 440                 445 gac atg gtc tct gac atg ctg gct cca ctc aaa gta gcc act acc agc     1392
Asp Met Val Ser Asp Met Leu Ala Pro Leu Lys Val Ala Thr Thr Ser
450                 455                 460 cat cga gtc ccc gac tcg ggc ccg gag cct atc ctg gcc ttc tac ggc     1440
His Arg Val Pro Asp Ser Gly Pro Glu Pro Ile Leu Ala Phe Tyr Gly
465                 470                 475                 480 agc cgc ttg act ggc cgc cat aag gcc cgc aag gcc cca gca ggc tcc     1488
Ser Arg Leu Thr Gly Arg His Lys Ala Arg Lys Ala Pro Ala Gly Ser
                485                 490                 495
```

```
aaa tcc gac tcc aac ttc agt aac ctc atc cgg ctg agc cag gcc tca   1536
Lys Ser Asp Ser Asn Phe Ser Asn Leu Ile Arg Leu Ser Gln Ala Ser
        500                 505                 510 cct gag gat gcg ggg tcc tgt agg ggc agt ggt tgg gaa gaa gga gaa   1584
Pro Glu Asp Ala Gly Ser Cys Arg Gly Ser Gly Trp Glu Glu Gly Glu
        515                 520                 525 ggc cac acg act tcc aca gag ccg tct gcc atc cca caa cgg gaa gga   1632
Gly His Thr Thr Ser Thr Glu Pro Ser Ala Ile Pro Gln Arg Glu Gly
530                 535                 540 gat gga ccc agc atc aaa gac agg ccc atg gat gct gag agg tca ggc   1680
Asp Gly Pro Ser Ile Lys Asp Arg Pro Met Asp Ala Glu Arg Ser Gly
545                 550                 555                 560 cct gag ctc ttt gat ccc agc ggc tgt cct gga gag tgg cta aat gaa   1728
Pro Glu Leu Phe Asp Pro Ser Gly Cys Pro Gly Glu Trp Leu Asn Glu
                565                 570                 575 cca gaa tgg acc cta gag ggc atc cgg ggg tct cga gct caa ggg ctt   1776
Pro Glu Trp Thr Leu Glu Gly Ile Arg Gly Ser Arg Ala Gln Gly Leu
            580                 585                 590 cca gct cgc cat ccc cac cca cac ggg ccg ccc agg acc acc agc ttt   1824
Pro Ala Arg His Pro His Pro His Gly Pro Pro Arg Thr Thr Ser Phe
        595                 600                 605 ctg cag cat gtt gga ggg cac cac tga                               1851
Leu Gln His Val Gly Gly His His
    610                 615

<210> SEQ ID NO 17
<211> LENGTH: 616
<212> TYPE: PRT
<213> ORGANISM: Rattus norvegicus

<400> SEQUENCE: 17

Met Ala Thr Ile Gln Ser Glu Thr Asp Cys Tyr Asp Ile Ile Glu Val
1               5                   10                  15

Leu Gly Lys Gly Thr Phe Gly Glu Val Ala Lys Gly Trp Arg Arg Ser
            20                  25                  30

Thr Gly Glu Met Val Ala Ile Lys Ile Leu Lys Asn Asp Ala Tyr Arg
        35                  40                  45

Ser Arg Ile Ile Lys Asn Glu Leu Lys Leu Leu Arg Cys Val Arg Gly
    50                  55                  60

Leu Asp Pro Asp Glu Ala His Val Ile Arg Phe Leu Glu Phe His His
65                  70                  75                  80

Asp Ala Leu Lys Phe Tyr Leu Val Phe Glu Leu Leu Glu Gln Asn Leu
                85                  90                  95

Phe Glu Phe Gln Lys Glu Asn Asn Phe Ala Pro Leu Pro Ala Arg His
            100                 105                 110

Ile Arg Thr Val Thr Leu Gln Val Leu Arg Ala Leu Ala Arg Leu Lys
        115                 120                 125

Glu Leu Ala Ile Ile His Ala Asp Leu Lys Pro Glu Asn Ile Met Leu
    130                 135                 140

Val Asp Gln Thr Arg Cys Pro Phe Arg Val Lys Val Ile Asp Phe Gly
145                 150                 155                 160

Ser Ala Ser Ile Phe Ser Glu Val Arg Tyr Val Lys Glu Pro Tyr Ile
                165                 170                 175

Gln Ser Arg Phe Tyr Arg Ala Pro Glu Ile Leu Leu Gly Leu Pro Phe
            180                 185                 190

Cys Glu Lys Val Asp Val Trp Ser Leu Gly Cys Val Met Ala Glu Leu
        195                 200                 205
```

```
His Leu Gly Trp Pro Leu Tyr Pro Gly Asn Asn Glu Tyr Asp Gln Val
    210                 215                 220

Arg Tyr Ile Cys Glu Thr Gln Gly Leu Pro Lys Pro His Leu Leu His
225                 230                 235                 240

Ala Ala Arg Lys Ala His His Phe Phe Lys Arg Asn Pro His Pro Asp
                245                 250                 255

Ala Thr Asn Pro Trp Gln Leu Lys Ser Ser Ala Asp Tyr Leu Ala Glu
            260                 265                 270

Thr Lys Val Arg Pro Leu Glu Arg Arg Lys Tyr Met Leu Lys Ser Leu
        275                 280                 285

Asp Gln Ile Glu Thr Val Asn Gly Gly Ala Val Asn Arg Leu Ser
    290                 295                 300

Phe Pro Asp Arg Glu Ala Leu Ala Glu His Ala Asp Leu Lys Ser Met
305                 310                 315                 320

Val Glu Leu Ile Lys Arg Met Leu Thr Trp Glu Ser His Glu Arg Ile
                325                 330                 335

Ser Pro Ser Ala Ala Leu Arg His Pro Phe Val Ser Met Gln Gln Leu
            340                 345                 350

Arg Ser Ala His Glu Ala Thr Arg Tyr Tyr Gln Leu Ser Leu Arg Gly
        355                 360                 365

Cys Arg Leu Ser Leu Gln Val Asp Gly Lys Pro Pro Pro Val Ile
370                 375                 380

Ala Asn Ala Glu Asp Gly Pro Pro Tyr Tyr Arg Leu Ala Glu Glu Glu
385                 390                 395                 400

Glu Thr Ala Gly Leu Gly Gly Val Thr Gly Ser Gly Ser Phe Phe Arg
                405                 410                 415

Glu Asp Lys Ala Pro Gly Met Gln Arg Ala Ile Asp Gln Leu Asp Asp
            420                 425                 430

Leu Ser Leu Gln Glu Ala Arg Arg Gly Leu Trp Ser Asp Thr Arg Ala
        435                 440                 445

Asp Met Val Ser Asp Met Leu Ala Pro Leu Lys Val Ala Thr Thr Ser
    450                 455                 460

His Arg Val Pro Asp Ser Gly Pro Glu Pro Ile Leu Ala Phe Tyr Gly
465                 470                 475                 480

Ser Arg Leu Thr Gly Arg His Lys Ala Arg Lys Ala Pro Ala Gly Ser
                485                 490                 495

Lys Ser Asp Ser Asn Phe Ser Asn Leu Ile Arg Leu Ser Gln Ala Ser
            500                 505                 510

Pro Glu Asp Ala Gly Ser Cys Arg Gly Ser Gly Trp Glu Glu Gly Glu
        515                 520                 525

Gly His Thr Thr Ser Thr Glu Pro Ser Ala Ile Pro Gln Arg Glu Gly
    530                 535                 540

Asp Gly Pro Ser Ile Lys Asp Arg Pro Met Asp Ala Glu Arg Ser Gly
545                 550                 555                 560

Pro Glu Leu Phe Asp Pro Ser Gly Cys Pro Gly Glu Trp Leu Asn Glu
                565                 570                 575

Pro Glu Trp Thr Leu Glu Gly Ile Arg Gly Ser Arg Ala Gln Gly Leu
            580                 585                 590

Pro Ala Arg His Pro His Pro His Gly Pro Pro Arg Thr Thr Ser Phe
        595                 600                 605

Leu Gln His Val Gly Gly His His
    610                 615
```

<210> SEQ ID NO 18
<211> LENGTH: 21
<212> TYPE: DNA
<213> ORGANISM: Homo sapiens

<400> SEQUENCE: 18
aagatcctca agaatgacgc c        21

<210> SEQ ID NO 19
<211> LENGTH: 21
<212> TYPE: DNA
<213> ORGANISM: Homo sapiens

<400> SEQUENCE: 19
aagaatgacg cctaccgcaa c        21

<210> SEQ ID NO 20
<211> LENGTH: 21
<212> TYPE: DNA
<213> ORGANISM: Homo sapiens

<400> SEQUENCE: 20
aaccgcatca tcaagaacga g        21

<210> SEQ ID NO 21
<211> LENGTH: 21
<212> TYPE: DNA
<213> ORGANISM: Homo sapiens

<400> SEQUENCE: 21
aagaacgagc tgaagctgct g        21

<210> SEQ ID NO 22
<211> LENGTH: 21
<212> TYPE: DNA
<213> ORGANISM: Homo sapiens

<400> SEQUENCE: 22
aaggagctgg ctatcatcca c        21

<210> SEQ ID NO 23
<211> LENGTH: 21
<212> TYPE: DNA
<213> ORGANISM: Homo sapiens

<400> SEQUENCE: 23
aagcctgaga acatcatgct g        21

<210> SEQ ID NO 24
<211> LENGTH: 21
<212> TYPE: DNA
<213> ORGANISM: Homo sapiens

<400> SEQUENCE: 24
aacatcatgc tggtggacca g        21

<210> SEQ ID NO 25
<211> LENGTH: 21
<212> TYPE: DNA
<213> ORGANISM: Homo sapiens

<400> SEQUENCE: 25
aaggtgattg acttcggatc c        21

```
<210> SEQ ID NO 26
<211> LENGTH: 21
<212> TYPE: DNA
<213> ORGANISM: Homo sapiens

<400> SEQUENCE: 26
aaggagccat acatccagtc g                                              21

<210> SEQ ID NO 27
<211> LENGTH: 21
<212> TYPE: DNA
<213> ORGANISM: Homo sapiens

<400> SEQUENCE: 27
aacaacgagt acgaccaggt g                                              21

<210> SEQ ID NO 28
<211> LENGTH: 21
<212> TYPE: DNA
<213> ORGANISM: Homo sapiens

<400> SEQUENCE: 28
aagtcgttgg accagattga g                                              21

<210> SEQ ID NO 29
<211> LENGTH: 21
<212> TYPE: DNA
<213> ORGANISM: Homo sapiens

<400> SEQUENCE: 29
aagagcatgg tggagctgat c                                              21

<210> SEQ ID NO 30
<211> LENGTH: 21
<212> TYPE: DNA
<213> ORGANISM: Homo sapiens

<400> SEQUENCE: 30
aatgcggtct ccgacatgat g                                              21

<210> SEQ ID NO 31
<211> LENGTH: 21
<212> TYPE: DNA
<213> ORGANISM: Homo sapiens

<400> SEQUENCE: 31
aagtccgact ccaacttcag c                                              21

<210> SEQ ID NO 32
<211> LENGTH: 21
<212> TYPE: DNA
<213> ORGANISM: Homo sapiens

<400> SEQUENCE: 32
aacttcagca acctcattcg g                                              21

<210> SEQ ID NO 33
<211> LENGTH: 21
<212> TYPE: DNA
<213> ORGANISM: Homo sapiens

<400> SEQUENCE: 33
aacatgacca tggaagctga g                                              21
```

```
<210> SEQ ID NO 34
<211> LENGTH: 21
<212> TYPE: DNA
<213> ORGANISM: Homo sapiens

<400> SEQUENCE: 34
aatggctgag tgagccagac t                                              21

<210> SEQ ID NO 35
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 35
gauccucaag aaugacgccu u                                              21

<210> SEQ ID NO 36
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 36
gaaugacgcc uaccgcaacu u                                              21

<210> SEQ ID NO 37
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 37
ccgcaucauc aagaacgagu u                                              21

<210> SEQ ID NO 38
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 38
gaacgagcug aagcugcugu u                                              21

<210> SEQ ID NO 39
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 39
ggagcuggcu aucauccacu u                                              21

<210> SEQ ID NO 40
<211> LENGTH: 21
<212> TYPE: RNA
<213> ORGANISM: Artificial
<220> FEATURE:
<223> OTHER INFORMATION: siRNA polynucleotide, synthesized
```

-continued

```
<400> SEQUENCE: 40
gccugagaac aucaugcugu u                                      21

<210> SEQ ID NO 41
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 41
caucaugcug guggaccagu u                                      21

<210> SEQ ID NO 42
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 42
ggugauugac uucggauccu u                                      21

<210> SEQ ID NO 43
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 43
ggagccauac auccagucgu u                                      21

<210> SEQ ID NO 44
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 44
caacgaguac gaccaggugu u                                      21

<210> SEQ ID NO 45
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 45
gucguuggac cagauugagu u                                      21

<210> SEQ ID NO 46
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 46
gagcauggug gagcugaucu u                                      21

<210> SEQ ID NO 47
<211> LENGTH: 21
```

```
<212> TYPE: RNA
<213> ORGANISM: Artificial
<220> FEATURE:
<223> OTHER INFORMATION: siRNA polynucleotide, synthesized

<400> SEQUENCE: 47
ugcggucucc gacaugaugu u                                              21

<210> SEQ ID NO 48
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 48
guccgacucc aacuucagcu u                                              21

<210> SEQ ID NO 49
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 49
cuucagcaac cucauucggu u                                              21

<210> SEQ ID NO 50
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 50
caugaccaug gaagcugagu u                                              21

<210> SEQ ID NO 51
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 51
uggcugagug agccagacuu u                                              21

<210> SEQ ID NO 52
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 52
ggcgucauuc uugaggaucu u                                              21

<210> SEQ ID NO 53
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 53
```

-continued guugcgguag gcgucauucu u    21

<210> SEQ ID NO 54
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 54
cucguucuug augaugcggu u    21

<210> SEQ ID NO 55
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 55
cagcagcuuc agcucguucu u    21

<210> SEQ ID NO 56
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 56
guggaugaua gccagcuccu u    21

<210> SEQ ID NO 57
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 57
cagcaugaug uucucaggcu u    21

<210> SEQ ID NO 58
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 58
cugguccacc agcaugaugu u    21

<210> SEQ ID NO 59
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 59
ggauccgaag ucaaucaccu u    21

<210> SEQ ID NO 60
<211> LENGTH: 21
<212> TYPE: RNA
<213> ORGANISM: Artificial

```
-continued

<220> FEATURE:
<223> OTHER INFORMATION: siRNA polynucleotide, synthesized

<400> SEQUENCE: 60
cgacuggaug uauggcuccu u                                              21

<210> SEQ ID NO 61
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 61
caccuggucg uacucguugu u                                              21

<210> SEQ ID NO 62
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 62
cucaaucugg uccaacgacu u                                              21

<210> SEQ ID NO 63
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 63
gaucagcucc accaugcucu u                                              21

<210> SEQ ID NO 64
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 64
caucaugucg gagaccgcau u                                              21

<210> SEQ ID NO 65
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 65
gcugaaguug gagucggacu u                                              21

<210> SEQ ID NO 66
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 66
ccgaaugagg uugcugaagu u                                              21
```

```
<210> SEQ ID NO 67
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 67
cucagcuucc auggucaugu u                                              21

<210> SEQ ID NO 68
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 68
agucuggcuc acucagccau u                                              21

<210> SEQ ID NO 69
<211> LENGTH: 21
<212> TYPE: DNA
<213> ORGANISM: Homo sapiens

<400> SEQUENCE: 69
caagatcctc aagaatgacg c                                              21

<210> SEQ ID NO 70
<211> LENGTH: 21
<212> TYPE: DNA
<213> ORGANISM: Homo sapiens

<400> SEQUENCE: 70
caagaatgac gcctaccgca a                                              21

<210> SEQ ID NO 71
<211> LENGTH: 21
<212> TYPE: DNA
<213> ORGANISM: Homo sapiens

<400> SEQUENCE: 71
caaccgcatc atcaagaacg a                                              21

<210> SEQ ID NO 72
<211> LENGTH: 21
<212> TYPE: DNA
<213> ORGANISM: Homo sapiens

<400> SEQUENCE: 72
catcaagaac gagctgaagc t                                              21

<210> SEQ ID NO 73
<211> LENGTH: 21
<212> TYPE: DNA
<213> ORGANISM: Homo sapiens

<400> SEQUENCE: 73
caagaacgag ctgaagctgc t                                              21

<210> SEQ ID NO 74
<211> LENGTH: 21
<212> TYPE: DNA
<213> ORGANISM: Homo sapiens
```

<400> SEQUENCE: 74
catccgcttc cttgagttct t                                              21

<210> SEQ ID NO 75
<211> LENGTH: 21
<212> TYPE: DNA
<213> ORGANISM: Homo sapiens

<400> SEQUENCE: 75
cagaaggaga acaacttcgc g                                              21

<210> SEQ ID NO 76
<211> LENGTH: 21
<212> TYPE: DNA
<213> ORGANISM: Homo sapiens

<400> SEQUENCE: 76
caaggagctg gctatcatcc a                                              21

<210> SEQ ID NO 77
<211> LENGTH: 21
<212> TYPE: DNA
<213> ORGANISM: Homo sapiens

<400> SEQUENCE: 77
caagcctgag aacatcatgc t                                              21

<210> SEQ ID NO 78
<211> LENGTH: 21
<212> TYPE: DNA
<213> ORGANISM: Homo sapiens

<400> SEQUENCE: 78
caaggtgatt gacttcggat c                                              21

<210> SEQ ID NO 79
<211> LENGTH: 21
<212> TYPE: DNA
<213> ORGANISM: Homo sapiens

<400> SEQUENCE: 79
catacatcca gtcgcgcttc t                                              21

<210> SEQ ID NO 80
<211> LENGTH: 21
<212> TYPE: DNA
<213> ORGANISM: Homo sapiens

<400> SEQUENCE: 80
caacaacgag tacgaccagg t                                              21

<210> SEQ ID NO 81
<211> LENGTH: 21
<212> TYPE: DNA
<213> ORGANISM: Homo sapiens

<400> SEQUENCE: 81
caccacttct tcaagcgcaa c                                              21

<210> SEQ ID NO 82
<211> LENGTH: 21
<212> TYPE: DNA

<213> ORGANISM: Homo sapiens

<400> SEQUENCE: 82
caagtcgttg gaccagattg a                                    21

<210> SEQ ID NO 83
<211> LENGTH: 21
<212> TYPE: DNA
<213> ORGANISM: Homo sapiens

<400> SEQUENCE: 83
caagagcatg gtggagctga t                                    21

<210> SEQ ID NO 84
<211> LENGTH: 21
<212> TYPE: DNA
<213> ORGANISM: Homo sapiens

<400> SEQUENCE: 84
caatgcggtc tccgacatga t                                    21

<210> SEQ ID NO 85
<211> LENGTH: 21
<212> TYPE: DNA
<213> ORGANISM: Homo sapiens

<400> SEQUENCE: 85
caagtccgac tccaacttca g                                    21

<210> SEQ ID NO 86
<211> LENGTH: 21
<212> TYPE: DNA
<213> ORGANISM: Homo sapiens

<400> SEQUENCE: 86
caacttcagc aacctcattc g                                    21

<210> SEQ ID NO 87
<211> LENGTH: 21
<212> TYPE: DNA
<213> ORGANISM: Homo sapiens

<400> SEQUENCE: 87
caacatgacc atggaagctg a                                    21

<210> SEQ ID NO 88
<211> LENGTH: 21
<212> TYPE: DNA
<213> ORGANISM: Homo sapiens

<400> SEQUENCE: 88
catgaccatg gaagctgaga g                                    21

<210> SEQ ID NO 89
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 89
agauccucaa gaaugacgcu u                                    21

```
<210> SEQ ID NO 90
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 90
agaaugacgc cuaccgcaau u                                              21

<210> SEQ ID NO 91
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 91
accgcaucau caagaacgau u                                              21

<210> SEQ ID NO 92
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 92
ucaagaacga gcugaagcuu u                                              21

<210> SEQ ID NO 93
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 93
agaacgagcu gaagcugcuu u                                              21

<210> SEQ ID NO 94
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 94
uccgcuuccu ugaguucuuu u                                              21

<210> SEQ ID NO 95
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 95
gaaggagaac aacuucgcgu u                                              21

<210> SEQ ID NO 96
<211> LENGTH: 21
<212> TYPE: RNA
<213> ORGANISM: Artificial
<220> FEATURE:
<223> OTHER INFORMATION: siRNA polynucleotide, synthesized
```

```
<400> SEQUENCE: 96
aggagcuggc uaucauccau u                                              21

<210> SEQ ID NO 97
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 97
agccugagaa caucaugcuu u                                              21

<210> SEQ ID NO 98
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 98
aggugauuga cuucggaucu u                                              21

<210> SEQ ID NO 99
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 99
uacauccagu cgcgcuucuu u                                              21

<210> SEQ ID NO 100
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 100
acaacgagua cgaccagguu u                                              21

<210> SEQ ID NO 101
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 101
ccacuucuuc aagcgcaacu u                                              21

<210> SEQ ID NO 102
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 102
agucguugga ccagauugau u                                              21

<210> SEQ ID NO 103
<211> LENGTH: 21
```

```
<212> TYPE: RNA
<213> ORGANISM: Artificial
<220> FEATURE:
<223> OTHER INFORMATION: siRNA polynucleotide, synthesized

<400> SEQUENCE: 103
agagcauggu ggagcugauu u                                            21

<210> SEQ ID NO 104
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 104
augcggucuc cgacaugauu u                                            21

<210> SEQ ID NO 105
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 105
aguccgacuc caacuucagu u                                            21

<210> SEQ ID NO 106
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 106
acuucagcaa ccucauucgu u                                            21

<210> SEQ ID NO 107
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 107
acaugaccau ggaagcugau u                                            21

<210> SEQ ID NO 108
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 108
ugaccaugga agcugagagu u                                            21

<210> SEQ ID NO 109
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 109
```

-continued gcgucauucu ugaggaucuu u         21

<210> SEQ ID NO 110
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 110
uugcgguagg cgucauucuu u         21

<210> SEQ ID NO 111
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 111
ucguucuuga ugaugcgguu u         21

<210> SEQ ID NO 112
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 112
agcuucagcu cguucuugau u         21

<210> SEQ ID NO 113
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 113
agcagcuuca gcucguucuu u         21

<210> SEQ ID NO 114
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 114
aagaacucaa ggaagcggau u         21

<210> SEQ ID NO 115
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 115
cgcgaaguug uucuccuucu u         21

<210> SEQ ID NO 116
<211> LENGTH: 21
<212> TYPE: RNA
<213> ORGANISM: Artificial

```
-continued

<220> FEATURE:
<223> OTHER INFORMATION: siRNA polynucleotide, synthesized

<400> SEQUENCE: 116
uggaugauag ccagcuccuu u                                              21

<210> SEQ ID NO 117
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 117
agcaugaugu ucucaggcuu u                                              21

<210> SEQ ID NO 118
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 118
gauccgaagu caaucaccuu u                                              21

<210> SEQ ID NO 119
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 119
agaagcgcga cuggauguau u                                              21

<210> SEQ ID NO 120
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 120 accggucgu acucguuguu u                                               21

<210> SEQ ID NO 121
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 121
guugcgcuug aagaaguggu u                                              21

<210> SEQ ID NO 122
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 122
ucaaucuggu ccaacgacuu u                                              21
```

<210> SEQ ID NO 123
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 123
aucagcucca ccaugcucuu u                                              21

<210> SEQ ID NO 124
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 124
aucaugucgg agaccgcauu u                                              21

<210> SEQ ID NO 125
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 125
cugaaguugg agucggacuu u                                              21

<210> SEQ ID NO 126
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 126
cgaaugaggu ugcugaaguu u                                              21

<210> SEQ ID NO 127
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 127
ucagcuucca uggucauguu u                                              21

<210> SEQ ID NO 128
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 128
cucucagcuu ccauggucau u                                              21

<210> SEQ ID NO 129
<211> LENGTH: 21
<212> TYPE: DNA
<213> ORGANISM: Homo sapiens

<400> SEQUENCE: 129

```
gagatggtgg ccatcaagat c                                              21

<210> SEQ ID NO 130
<211> LENGTH: 21
<212> TYPE: DNA
<213> ORGANISM: Homo sapiens

<400> SEQUENCE: 130
gatggtggcc atcaagatcc t                                              21

<210> SEQ ID NO 131
<211> LENGTH: 21
<212> TYPE: DNA
<213> ORGANISM: Homo sapiens

<400> SEQUENCE: 131
gatcctcaag aatgacgcct a                                              21

<210> SEQ ID NO 132
<211> LENGTH: 21
<212> TYPE: DNA
<213> ORGANISM: Homo sapiens

<400> SEQUENCE: 132
gagttccaga aggagaacaa c                                              21

<210> SEQ ID NO 133
<211> LENGTH: 21
<212> TYPE: DNA
<213> ORGANISM: Homo sapiens

<400> SEQUENCE: 133
gatctcaagc ctgagaacat c                                              21

<210> SEQ ID NO 134
<211> LENGTH: 21
<212> TYPE: DNA
<213> ORGANISM: Homo sapiens

<400> SEQUENCE: 134
gagaacatca tgctggtgga c                                              21

<210> SEQ ID NO 135
<211> LENGTH: 21
<212> TYPE: DNA
<213> ORGANISM: Homo sapiens

<400> SEQUENCE: 135
gaacatcatg ctggtggacc a                                              21

<210> SEQ ID NO 136
<211> LENGTH: 21
<212> TYPE: DNA
<213> ORGANISM: Homo sapiens

<400> SEQUENCE: 136
gaaggagcca tacatccagt c                                              21

<210> SEQ ID NO 137
<211> LENGTH: 21
<212> TYPE: DNA
<213> ORGANISM: Homo sapiens
```

-continued

```
<400> SEQUENCE: 137
gattgagaca gtgaatggtg g                                              21

<210> SEQ ID NO 138
<211> LENGTH: 21
<212> TYPE: DNA
<213> ORGANISM: Homo sapiens

<400> SEQUENCE: 138
gagacagtga atggtggcag t                                              21

<210> SEQ ID NO 139
<211> LENGTH: 21
<212> TYPE: DNA
<213> ORGANISM: Homo sapiens

<400> SEQUENCE: 139
gacagtgaat ggtggcagtg t                                              21

<210> SEQ ID NO 140
<211> LENGTH: 21
<212> TYPE: DNA
<213> ORGANISM: Homo sapiens

<400> SEQUENCE: 140
gagcatggtg gagctgatca a                                              21

<210> SEQ ID NO 141
<211> LENGTH: 21
<212> TYPE: DNA
<213> ORGANISM: Homo sapiens

<400> SEQUENCE: 141
gagaaggcac caggtatgca a                                              21

<210> SEQ ID NO 142
<211> LENGTH: 21
<212> TYPE: DNA
<213> ORGANISM: Homo sapiens

<400> SEQUENCE: 142
gactccaact tcagcaacct c                                              21

<210> SEQ ID NO 143
<211> LENGTH: 21
<212> TYPE: DNA
<213> ORGANISM: Homo sapiens

<400> SEQUENCE: 143
gacaacatga ccatggaagc t                                              21

<210> SEQ ID NO 144
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 144
gaugguggcc aucaagaucu u                                              21

<210> SEQ ID NO 145
<211> LENGTH: 21
```

```
<212> TYPE: RNA
<213> ORGANISM: Artificial
<220> FEATURE:
<223> OTHER INFORMATION: siRNA polynucleotide, synthesized

<400> SEQUENCE: 145
ugguggccau caagauccuu u                                              21

<210> SEQ ID NO 146
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 146
uccucaagaa ugacgccuau u                                              21

<210> SEQ ID NO 147
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 147
guuccagaag gagaacaacu u                                              21

<210> SEQ ID NO 148
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 148
ucucaagccu gagaacaucu u                                              21

<210> SEQ ID NO 149
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 149
gaacaucaug cugguggacu u                                              21

<210> SEQ ID NO 150
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 150
acaucaugcu gguggaccau u                                              21

<210> SEQ ID NO 151
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 151
```

-continued aggagccaua cauccagucu u                                        21

<210> SEQ ID NO 152
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 152
uugagacagu gaaugguggu u                                        21

<210> SEQ ID NO 153
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 153
gacagugaau gguggcaguu u                                        21

<210> SEQ ID NO 154
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 154
cagugaaugg uggcaguguu u                                        21

<210> SEQ ID NO 155
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 155
gcauggugga gcugaucaau u                                        21

<210> SEQ ID NO 156
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 156
gaaggcacca gguaugcaau u                                        21

<210> SEQ ID NO 157
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 157
cuccaacuuc agcaaccucu u                                        21

<210> SEQ ID NO 158
<211> LENGTH: 21
<212> TYPE: RNA
<213> ORGANISM: Artificial

```
<220> FEATURE:
<223> OTHER INFORMATION: siRNA polynucleotide, synthesized

<400> SEQUENCE: 158
caacaugacc auggaagcuu u                                              21

<210> SEQ ID NO 159
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 159
gaucuugaug gccaccaucu u                                              21

<210> SEQ ID NO 160
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 160
aggaucuuga uggccaccau u                                              21

<210> SEQ ID NO 161
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 161
uaggcgucau ucuugaggau u                                              21

<210> SEQ ID NO 162
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 162
guuguucucc uucuggaacu u                                              21

<210> SEQ ID NO 163
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 163
gauguucuca ggcuugagau u                                              21

<210> SEQ ID NO 164
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 164
guccaccagc augauguucu u                                              21
```

```
<210> SEQ ID NO 165
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 165
ugguccacca gcaugauguu u                                              21

<210> SEQ ID NO 166
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 166
gacuggaugu auggcuccuu u                                              21

<210> SEQ ID NO 167
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 167
ccaccauuca cugucucaau u                                              21

<210> SEQ ID NO 168
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 168
acugccacca uucacugucu u                                              21

<210> SEQ ID NO 169
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 169
acacugccac cauucacugu u                                              21

<210> SEQ ID NO 170
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 170
uugaucagcu ccaccaugcu u                                              21

<210> SEQ ID NO 171
<211> LENGTH: 21
<212> TYPE: RNA
<213> ORGANISM: Artificial
<220> FEATURE:
<223> OTHER INFORMATION: siRNA polynucleotide, synthesized
```

```
<400> SEQUENCE: 171
uugcauaccu ggugccuucu u                                    21

<210> SEQ ID NO 172
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 172
gagguugcug aaguuggagu u                                    21

<210> SEQ ID NO 173
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 173
agcuuccaug gucauguugu u                                    21

<210> SEQ ID NO 174
<211> LENGTH: 21
<212> TYPE: DNA
<213> ORGANISM: Homo sapiens

<400> SEQUENCE: 174
taccgcaacc gcatcatcaa g                                    21

<210> SEQ ID NO 175
<211> LENGTH: 21
<212> TYPE: DNA
<213> ORGANISM: Homo sapiens

<400> SEQUENCE: 175
tacgtgaagg agccatacat c                                    21

<210> SEQ ID NO 176
<211> LENGTH: 21
<212> TYPE: DNA
<213> ORGANISM: Homo sapiens

<400> SEQUENCE: 176
tacatccagt cgcgcttcta c                                    21

<210> SEQ ID NO 177
<211> LENGTH: 21
<212> TYPE: DNA
<213> ORGANISM: Homo sapiens

<400> SEQUENCE: 177
tatgctcaag tcgttggacc a                                    21

<210> SEQ ID NO 178
<211> LENGTH: 21
<212> TYPE: DNA
<213> ORGANISM: Homo sapiens

<400> SEQUENCE: 178
tactactgtc tggctgagga g                                    21
```

```
<210> SEQ ID NO 179
<211> LENGTH: 21
<212> TYPE: DNA
<213> ORGANISM: Homo sapiens

<400> SEQUENCE: 179
tactgtctgg ctgaggagaa g                                              21

<210> SEQ ID NO 180
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 180
ccgcaaccgc aucaucaagu u                                              21

<210> SEQ ID NO 181
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 181
cgugaaggag ccauacaucu u                                              21

<210> SEQ ID NO 182
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 182
cauccagucg cgcuucuacu u                                              21

<210> SEQ ID NO 183
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 183
ugcucaaguc guuggaccau u                                              21

<210> SEQ ID NO 184
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 184
cuacugucug gcugaggagu u                                              21

<210> SEQ ID NO 185
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 185
```
cugucuggcu gaggagaagu u                                        21

<210> SEQ ID NO 186
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 186
cuugaugaug cgguugcggu u                                        21

<210> SEQ ID NO 187
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 187
gauguauggc uccuucacgu u                                        21

<210> SEQ ID NO 188
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 188
guagaagcgc gacuggaugu u                                        21

<210> SEQ ID NO 189
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 189
ugguccaacg acuugagcau u                                        21

<210> SEQ ID NO 190
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 190
cuccucagcc agacaguagu u                                        21

<210> SEQ ID NO 191
<211> LENGTH: 21
<212> TYPE: RNA
<213> ORGANISM: Artificial
<220> FEATURE:
<223> OTHER INFORMATION: siRNA polynucleotide, synthesized

<400> SEQUENCE: 191
cuucuccuca gccagacagu u                                        21

<210> SEQ ID NO 192
<211> LENGTH: 1851
<212> TYPE: DNA

<213> ORGANISM: artificial
<220> FEATURE:
<223> OTHER INFORMATION: human HIPK4 Lys40 to Ser40, wherein yyy encodes Serine
<220> FEATURE:
<221> NAME/KEY: CDS
<222> LOCATION: (1)..(1848)

<400> SEQUENCE: 192

```
atg tcc acc atc cag tcg gag act gac tgc tac gac atc atc gag gtc        48
Met Ser Thr Ile Gln Ser Glu Thr Asp Cys Tyr Asp Ile Ile Glu Val
1               5                   10                  15 ttg ggc aag ggg acc ttc ggg gag gta gcc aag ggc tgg cgg cgg agc        96
Leu Gly Lys Gly Thr Phe Gly Glu Val Ala Lys Gly Trp Arg Arg Ser
            20                  25                  30 acg ggc gag atg gtg gcc atc yyy atc ctc aag aat gac gcc tac cgc       144
Thr Gly Glu Met Val Ala Ile Xaa Ile Leu Lys Asn Asp Ala Tyr Arg
        35                  40                  45 aac cgc atc atc aag aac gag ctg aag ctg ctg cac tgc atg cga ggc       192
Asn Arg Ile Ile Lys Asn Glu Leu Lys Leu Leu His Cys Met Arg Gly
    50                  55                  60 cta gac cct gaa gag gcc cac gtc atc cgc ttc ctt gag ttc ttc cat       240
Leu Asp Pro Glu Glu Ala His Val Ile Arg Phe Leu Glu Phe Phe His
65                  70                  75                  80 gac gcc ctc aag ttc tac ctg gtc ttt gag ctg ctg gag caa aac ctt       288
Asp Ala Leu Lys Phe Tyr Leu Val Phe Glu Leu Leu Glu Gln Asn Leu
                85                  90                  95 ttc gag ttc cag aag gag aac aac ttc gcg ccc ctc ccc gcc cgc cac       336
Phe Glu Phe Gln Lys Glu Asn Asn Phe Ala Pro Leu Pro Ala Arg His
            100                 105                 110 atc cgt aca gtc acc ctg cag gtg ctc aca gcc ctg gcc cgg ctc aag       384
Ile Arg Thr Val Thr Leu Gln Val Leu Thr Ala Leu Ala Arg Leu Lys
        115                 120                 125 gag ctg gct atc atc cac gct gat ctc aag cct gag aac atc atg ctg       432
Glu Leu Ala Ile Ile His Ala Asp Leu Lys Pro Glu Asn Ile Met Leu
    130                 135                 140 gtg gac cag acc cgc tgc ccc ttc agg gtc aag gtg att gac ttc gga       480
Val Asp Gln Thr Arg Cys Pro Phe Arg Val Lys Val Ile Asp Phe Gly
145                 150                 155                 160 tcc gcc agc att ttc agc gag gtg cgc tac gtg aag gag cca tac atc       528
Ser Ala Ser Ile Phe Ser Glu Val Arg Tyr Val Lys Glu Pro Tyr Ile
                165                 170                 175 cag tcg cgc ttc tac cgg gcc cct gag atc ctg ctg ggg ctg ccc ttc       576
Gln Ser Arg Phe Tyr Arg Ala Pro Glu Ile Leu Leu Gly Leu Pro Phe
            180                 185                 190 tgc gag aag gtg gac gtg tgg tcc ctg ggc tgc gtc atg gct gag ctg       624
Cys Glu Lys Val Asp Val Trp Ser Leu Gly Cys Val Met Ala Glu Leu
        195                 200                 205 cac ctg ggc tgg cct ctc tac ccc ggc aac aac gag tac gac cag gtg       672
His Leu Gly Trp Pro Leu Tyr Pro Gly Asn Asn Glu Tyr Asp Gln Val
    210                 215                 220 cgc tac atc tgc gaa acc cag ggc ctg ccc aag cca cac ctg ttg cac       720
Arg Tyr Ile Cys Glu Thr Gln Gly Leu Pro Lys Pro His Leu Leu His
225                 230                 235                 240 gcc gcc tgc aag gcc cac cac ttc ttc aag cgc aac ccc cac cct gac       768
Ala Ala Cys Lys Ala His His Phe Phe Lys Arg Asn Pro His Pro Asp
                245                 250                 255 gct gcc aac ccc tgg cag ctc aag tcc tcg gct gac tac ctg gcc gag       816
Ala Ala Asn Pro Trp Gln Leu Lys Ser Ser Ala Asp Tyr Leu Ala Glu
            260                 265                 270 acg aag gtg cgc cca ttg gag cgc cgc aag tat atg ctc aag tcg ttg       864
Thr Lys Val Arg Pro Leu Glu Arg Arg Lys Tyr Met Leu Lys Ser Leu
```

```
          Thr Lys Val Arg Pro Leu Glu Arg Arg Lys Tyr Met Leu Lys Ser Leu
                  275                 280                 285 gac cag att gag aca gtg aat ggt ggc agt gtg gcc agt cgg cta acc              912
Asp Gln Ile Glu Thr Val Asn Gly Gly Ser Val Ala Ser Arg Leu Thr
            290                 295                 300 ttc cct gac cgg gag gcg ctg gcg gag cac gcc gac ctc aag agc atg              960
Phe Pro Asp Arg Glu Ala Leu Ala Glu His Ala Asp Leu Lys Ser Met
305                 310                 315                 320 gtg gag ctg atc aag cgc atg ctg acc tgg gag tca cac gaa cgc atc             1008
Val Glu Leu Ile Lys Arg Met Leu Thr Trp Glu Ser His Glu Arg Ile
                325                 330                 335 agc ccc agt gct gcc ctg cgc cac ccc ttc gtg tcc atg cag cag ctg             1056
Ser Pro Ser Ala Ala Leu Arg His Pro Phe Val Ser Met Gln Gln Leu
            340                 345                 350 cgc agt gcc cac gag acc acc cac tac tac cag ctc tcg ctg cgc agc             1104
Arg Ser Ala His Glu Thr Thr His Tyr Tyr Gln Leu Ser Leu Arg Ser
        355                 360                 365 tac cgc ctc tcg ctg caa gtg gag ggg aag ccc ccc acg ccc gtc gtg             1152
Tyr Arg Leu Ser Leu Gln Val Glu Gly Lys Pro Pro Thr Pro Val Val
    370                 375                 380 gcc gca gaa gat ggg acc ccc tac tac tgt ctg gct gag gag aag gag             1200
Ala Ala Glu Asp Gly Thr Pro Tyr Tyr Cys Leu Ala Glu Glu Lys Glu
385                 390                 395                 400 gct gcg ggt atg ggc agt gtg gcc ggc agc agc ccc ttc ttc cga gag             1248
Ala Ala Gly Met Gly Ser Val Ala Gly Ser Ser Pro Phe Phe Arg Glu
                405                 410                 415 gag aag gca cca ggt atg caa aga gcc atc gac cag ctg gat gac ctg             1296
Glu Lys Ala Pro Gly Met Gln Arg Ala Ile Asp Gln Leu Asp Asp Leu
            420                 425                 430 agt ctg cag gag gct ggg cat ggg ctg tgg ggt gag acc tgc acc aat             1344
Ser Leu Gln Glu Ala Gly His Gly Leu Trp Gly Glu Thr Cys Thr Asn
        435                 440                 445 gcg gtc tcc gac atg atg gtc ccc ctc aag gca gcc atc act ggc cac             1392
Ala Val Ser Asp Met Met Val Pro Leu Lys Ala Ala Ile Thr Gly His
    450                 455                 460 cat gtg ccc gac tcg ggc cct gag ccc atc ctg gcc ttc tac agc agc             1440
His Val Pro Asp Ser Gly Pro Glu Pro Ile Leu Ala Phe Tyr Ser Ser
465                 470                 475                 480 cgc ctg gca ggc cgc cac aag gcc cgc aag cca cct gcg ggt tcc aag             1488
Arg Leu Ala Gly Arg His Lys Ala Arg Lys Pro Pro Ala Gly Ser Lys
                485                 490                 495 tcc gac tcc aac ttc agc aac ctc att cgg ctg agc cag gtc tcg cct             1536
Ser Asp Ser Asn Phe Ser Asn Leu Ile Arg Leu Ser Gln Val Ser Pro
            500                 505                 510 gag gat gac agg ccc tgc cgg ggc agc agc tgg gag gaa gga gag cat             1584
Glu Asp Asp Arg Pro Cys Arg Gly Ser Ser Trp Glu Glu Gly Glu His
        515                 520                 525 ctc ggg gcc tct gct gag cca ctg gcc atc ctg cag cga gat gag gat             1632
Leu Gly Ala Ser Ala Glu Pro Leu Ala Ile Leu Gln Arg Asp Glu Asp
    530                 535                 540 ggg ccc aac att gac aac atg acc atg gaa gct gag agg cca gac cct             1680
Gly Pro Asn Ile Asp Asn Met Thr Met Glu Ala Glu Arg Pro Asp Pro
545                 550                 555                 560 gag ctc ttc gac ccc agc agc tgt cct gga gaa tgg ctg agt gag cca             1728
Glu Leu Phe Asp Pro Ser Ser Cys Pro Gly Glu Trp Leu Ser Glu Pro
                565                 570                 575 gac tgc acc ctg gag agc gtc agg ggc cca cgg gct cag ggc ctc cca             1776
Asp Cys Thr Leu Glu Ser Val Arg Gly Pro Arg Ala Gln Gly Leu Pro
            580                 585                 590
```

```
                ccc cgc cgc tcc cac cag cat ggt cca ccc cgg ggg gcc acc agc ttc       1824
                Pro Arg Arg Ser His Gln His Gly Pro Pro Arg Gly Ala Thr Ser Phe
                        595                 600                 605 ctc cag cat gtc acc ggg cac cac tga                                    1851
                Leu Gln His Val Thr Gly His His
                    610                 615
```

<210> SEQ ID NO 193
<211> LENGTH: 616
<212> TYPE: PRT
<213> ORGANISM: artificial
<220> FEATURE:
<221> NAME/KEY: misc_feature
<222> LOCATION: (40)..(40)
<223> OTHER INFORMATION: The 'Xaa' at location 40 stands for Pro, Leu,
      Ser, or Phe.
<220> FEATURE:
<223> OTHER INFORMATION: Synthetic Construct

<400> SEQUENCE: 193

Met Ser Thr Ile Gln Ser Glu Thr Asp Cys Tyr Asp Ile Ile Glu Val
1               5                   10                  15

Leu Gly Lys Gly Thr Phe Gly Glu Val Ala Lys Gly Trp Arg Arg Ser
            20                  25                  30

Thr Gly Glu Met Val Ala Ile Xaa Ile Leu Lys Asn Asp Ala Tyr Arg
        35                  40                  45

Asn Arg Ile Ile Lys Asn Glu Leu Lys Leu Leu His Cys Met Arg Gly
    50                  55                  60

Leu Asp Pro Glu Glu Ala His Val Ile Arg Phe Leu Glu Phe Phe His
65                  70                  75                  80

Asp Ala Leu Lys Phe Tyr Leu Val Phe Glu Leu Leu Glu Gln Asn Leu
                85                  90                  95

Phe Glu Phe Gln Lys Glu Asn Asn Phe Ala Pro Leu Pro Ala Arg His
            100                 105                 110

Ile Arg Thr Val Thr Leu Gln Val Leu Thr Ala Leu Ala Arg Leu Lys
        115                 120                 125

Glu Leu Ala Ile Ile His Ala Asp Leu Lys Pro Glu Asn Ile Met Leu
    130                 135                 140

Val Asp Gln Thr Arg Cys Pro Phe Arg Val Lys Val Ile Asp Phe Gly
145                 150                 155                 160

Ser Ala Ser Ile Phe Ser Glu Val Arg Tyr Val Lys Glu Pro Tyr Ile
                165                 170                 175

Gln Ser Arg Phe Tyr Arg Ala Pro Glu Ile Leu Leu Gly Leu Pro Phe
            180                 185                 190

Cys Glu Lys Val Asp Val Trp Ser Leu Gly Cys Val Met Ala Glu Leu
        195                 200                 205

His Leu Gly Trp Pro Leu Tyr Pro Gly Asn Asn Glu Tyr Asp Gln Val
    210                 215                 220

Arg Tyr Ile Cys Glu Thr Gln Gly Leu Pro Lys Pro His Leu Leu His
225                 230                 235                 240

Ala Ala Cys Lys Ala His His Phe Phe Lys Arg Asn Pro His Pro Asp
                245                 250                 255

Ala Ala Asn Pro Trp Gln Leu Lys Ser Ser Ala Asp Tyr Leu Ala Glu
            260                 265                 270

Thr Lys Val Arg Pro Leu Glu Arg Arg Lys Tyr Met Leu Lys Ser Leu
        275                 280                 285

Asp Gln Ile Glu Thr Val Asn Gly Gly Ser Val Ala Ser Arg Leu Thr
    290                 295                 300

```
Phe Pro Asp Arg Glu Ala Leu Ala Glu His Ala Asp Leu Lys Ser Met
305                 310                 315                 320

Val Glu Leu Ile Lys Arg Met Leu Thr Trp Glu Ser His Glu Arg Ile
            325                 330                 335

Ser Pro Ser Ala Ala Leu Arg His Pro Phe Val Ser Met Gln Gln Leu
        340                 345                 350

Arg Ser Ala His Glu Thr Thr His Tyr Tyr Gln Leu Ser Leu Arg Ser
    355                 360                 365

Tyr Arg Leu Ser Leu Gln Val Glu Gly Lys Pro Pro Thr Pro Val Val
370                 375                 380

Ala Ala Glu Asp Gly Thr Pro Tyr Tyr Cys Leu Ala Glu Lys Glu
385                 390                 395                 400

Ala Ala Gly Met Gly Ser Val Ala Gly Ser Ser Pro Phe Phe Arg Glu
            405                 410                 415

Glu Lys Ala Pro Gly Met Gln Arg Ala Ile Asp Gln Leu Asp Asp Leu
        420                 425                 430

Ser Leu Gln Glu Ala Gly His Gly Leu Trp Gly Glu Thr Cys Thr Asn
    435                 440                 445

Ala Val Ser Asp Met Met Val Pro Leu Lys Ala Ala Ile Thr Gly His
450                 455                 460

His Val Pro Asp Ser Gly Pro Glu Pro Ile Leu Ala Phe Tyr Ser Ser
465                 470                 475                 480

Arg Leu Ala Gly Arg His Lys Ala Arg Lys Pro Pro Ala Gly Ser Lys
            485                 490                 495

Ser Asp Ser Asn Phe Ser Asn Leu Ile Arg Leu Ser Gln Val Ser Pro
        500                 505                 510

Glu Asp Asp Arg Pro Cys Arg Gly Ser Ser Trp Glu Gly Glu His
    515                 520                 525

Leu Gly Ala Ser Ala Glu Pro Leu Ala Ile Leu Gln Arg Asp Glu Asp
530                 535                 540

Gly Pro Asn Ile Asp Asn Met Thr Met Glu Ala Glu Arg Pro Asp Pro
545                 550                 555                 560

Glu Leu Phe Asp Pro Ser Ser Cys Pro Gly Glu Trp Leu Ser Glu Pro
            565                 570                 575

Asp Cys Thr Leu Glu Ser Val Arg Gly Pro Arg Ala Gln Gly Leu Pro
        580                 585                 590

Pro Arg Arg Ser His Gln His Gly Pro Pro Arg Gly Ala Thr Ser Phe
    595                 600                 605

Leu Gln His Val Thr Gly His His
610                 615

<210> SEQ ID NO 194
<211> LENGTH: 1851
<212> TYPE: DNA
<213> ORGANISM: artificial
<220> FEATURE:
<223> OTHER INFORMATION: human HIPK4 Lys40 to Ser40, Asp136 to Trp136,
      wherein yyy encodes serine
<220> FEATURE:
<221> NAME/KEY: CDS
<222> LOCATION: (1)..(1848)

<400> SEQUENCE: 194 atg tcc acc atc cag tcg gag act gac tgc tac gac atc atc gag gtc    48
Met Ser Thr Ile Gln Ser Glu Thr Asp Cys Tyr Asp Ile Ile Glu Val
1               5                   10                  15
```

| | | |
|---|---|---|
| ttg ggc aag ggg acc ttc ggg gag gta gcc aag ggc tgg cgg cgg agc<br>Leu Gly Lys Gly Thr Phe Gly Glu Val Ala Lys Gly Trp Arg Arg Ser<br>20 25 30 | 96 | |
| acg ggc gag atg gtg gcc atc yyy atc ctc aag aat gac gcc tac cgc<br>Thr Gly Glu Met Val Ala Ile Xaa Ile Leu Lys Asn Asp Ala Tyr Arg<br>35 40 45 | 144 | |
| aac cgc atc atc aag aac gag ctg aag ctg ctg cac tgc atg cga ggc<br>Asn Arg Ile Ile Lys Asn Glu Leu Lys Leu Leu His Cys Met Arg Gly<br>50 55 60 | 192 | |
| cta gac cct gaa gag gcc cac gtc atc cgc ttc ctt gag ttc ttc cat<br>Leu Asp Pro Glu Glu Ala His Val Ile Arg Phe Leu Glu Phe Phe His<br>65 70 75 80 | 240 | |
| gac gcc ctc aag ttc tac ctg gtc ttt gag ctg ctg gag caa aac ctt<br>Asp Ala Leu Lys Phe Tyr Leu Val Phe Glu Leu Leu Glu Gln Asn Leu<br>85 90 95 | 288 | |
| ttc gag ttc cag aag gag aac aac ttc gcg ccc ctc ccc gcc cgc cac<br>Phe Glu Phe Gln Lys Glu Asn Asn Phe Ala Pro Leu Pro Ala Arg His<br>100 105 110 | 336 | |
| atc cgt aca gtc acc ctg cag gtg ctc aca gcc ctg gcc cgg ctc aag<br>Ile Arg Thr Val Thr Leu Gln Val Leu Thr Ala Leu Ala Arg Leu Lys<br>115 120 125 | 384 | |
| gag ctg gct atc atc cac gct tgg ctc aag cct gag aac atc atg ctg<br>Glu Leu Ala Ile Ile His Ala Trp Leu Lys Pro Glu Asn Ile Met Leu<br>130 135 140 | 432 | |
| gtg gac cag acc cgc tgc ccc ttc agg gtc aag gtg att gac ttc gga<br>Val Asp Gln Thr Arg Cys Pro Phe Arg Val Lys Val Ile Asp Phe Gly<br>145 150 155 160 | 480 | |
| tcc gcc agc att ttc agc gag gtg cgc tac gtg aag gag cca tac atc<br>Ser Ala Ser Ile Phe Ser Glu Val Arg Tyr Val Lys Glu Pro Tyr Ile<br>165 170 175 | 528 | |
| cag tcg cgc ttc tac cgg gcc cct gag atc ctg ctg ggg ctg ccc ttc<br>Gln Ser Arg Phe Tyr Arg Ala Pro Glu Ile Leu Leu Gly Leu Pro Phe<br>180 185 190 | 576 | |
| tgc gag aag gtg gac gtg tgg tcc ctg ggc tgc gtc atg gct gag ctg<br>Cys Glu Lys Val Asp Val Trp Ser Leu Gly Cys Val Met Ala Glu Leu<br>195 200 205 | 624 | |
| cac ctg ggc tgg cct ctc tac ccc ggc aac aac gag tac gac cag gtg<br>His Leu Gly Trp Pro Leu Tyr Pro Gly Asn Asn Glu Tyr Asp Gln Val<br>210 215 220 | 672 | |
| cgc tac atc tgc gaa acc cag ggc ctg ccc aag cca cac ctg ttg cac<br>Arg Tyr Ile Cys Glu Thr Gln Gly Leu Pro Lys Pro His Leu Leu His<br>225 230 235 240 | 720 | |
| gcc gcc tgc aag gcc cac cac ttc ttc aag cgc aac ccc cac cct gac<br>Ala Ala Cys Lys Ala His His Phe Phe Lys Arg Asn Pro His Pro Asp<br>245 250 255 | 768 | |
| gct gcc aac ccc tgg cag ctc aag tcc tcg gct gac tac ctg gcc gag<br>Ala Ala Asn Pro Trp Gln Leu Lys Ser Ser Ala Asp Tyr Leu Ala Glu<br>260 265 270 | 816 | |
| acg aag gtg cgc cca ttg gag cgc cgc aag tat atg ctc aag tcg ttg<br>Thr Lys Val Arg Pro Leu Glu Arg Arg Lys Tyr Met Leu Lys Ser Leu<br>275 280 285 | 864 | |
| gac cag att gag aca gtg aat ggt ggc agt gtg gcc agt cgg cta acc<br>Asp Gln Ile Glu Thr Val Asn Gly Gly Ser Val Ala Ser Arg Leu Thr<br>290 295 300 | 912 | |
| ttc cct gac cgg gag gcg ctg gcg gag cac gcc gac ctc aag agc atg<br>Phe Pro Asp Arg Glu Ala Leu Ala Glu His Ala Asp Leu Lys Ser Met<br>305 310 315 320 | 960 | |
| gtg gag ctg atc aag cgc atg ctg acc tgg gag tca cac gaa cgc atc<br>Val Glu Leu Ile Lys Arg Met Leu Thr Trp Glu Ser His Glu Arg Ile<br>325 330 335 | 1008 | |

```
agc ccc agt gct gcc ctg cgc cac ccc ttc gtg tcc atg cag cag ctg    1056
Ser Pro Ser Ala Ala Leu Arg His Pro Phe Val Ser Met Gln Gln Leu
            340                 345                 350 cgc agt gcc cac gag acc acc cac tac tac cag ctc tcg ctg cgc agc    1104
Arg Ser Ala His Glu Thr Thr His Tyr Tyr Gln Leu Ser Leu Arg Ser
        355                 360                 365 tac cgc ctc tcg ctg caa gtg gag ggg aag ccc ccc acg ccc gtc gtg    1152
Tyr Arg Leu Ser Leu Gln Val Glu Gly Lys Pro Pro Thr Pro Val Val
370                 375                 380 gcc gca gaa gat ggg acc ccc tac tac tgt ctg gct gag gag aag gag    1200
Ala Ala Glu Asp Gly Thr Pro Tyr Tyr Cys Leu Ala Glu Glu Lys Glu
385                 390                 395                 400 gct gcg ggt atg ggc agt gtg gcc ggc agc agc ccc ttc ttc cga gag    1248
Ala Ala Gly Met Gly Ser Val Ala Gly Ser Ser Pro Phe Phe Arg Glu
                405                 410                 415 gag aag gca cca ggt atg caa aga gcc atc gac cag ctg gat gac ctg    1296
Glu Lys Ala Pro Gly Met Gln Arg Ala Ile Asp Gln Leu Asp Asp Leu
            420                 425                 430 agt ctg cag gag gct ggg cat ggg ctg tgg ggt gag acc tgc acc aat    1344
Ser Leu Gln Glu Ala Gly His Gly Leu Trp Gly Glu Thr Cys Thr Asn
        435                 440                 445 gcg gtc tcc gac atg atg gtc ccc ctc aag gca gcc atc act ggc cac    1392
Ala Val Ser Asp Met Met Val Pro Leu Lys Ala Ala Ile Thr Gly His
450                 455                 460 cat gtg ccc gac tcg ggc cct gag ccc atc ctg gcc ttc tac agc agc    1440
His Val Pro Asp Ser Gly Pro Glu Pro Ile Leu Ala Phe Tyr Ser Ser
465                 470                 475                 480 cgc ctg gca ggc cgc cac aag gcc cgc aag cca cct gcg ggt tcc aag    1488
Arg Leu Ala Gly Arg His Lys Ala Arg Lys Pro Pro Ala Gly Ser Lys
                485                 490                 495 tcc gac tcc aac ttc agc aac ctc att cgg ctg agc cag gtc tcg cct    1536
Ser Asp Ser Asn Phe Ser Asn Leu Ile Arg Leu Ser Gln Val Ser Pro
            500                 505                 510 gag gat gac agg ccc tgc cgg ggc agc agc tgg gag gaa gga gag cat    1584
Glu Asp Asp Arg Pro Cys Arg Gly Ser Ser Trp Glu Glu Gly Glu His
        515                 520                 525 ctc ggg gcc tct gct gag cca ctg gcc atc ctg cag cga gat gag gat    1632
Leu Gly Ala Ser Ala Glu Pro Leu Ala Ile Leu Gln Arg Asp Glu Asp
530                 535                 540 ggg ccc aac att gac aac atg acc atg gaa gct gag agg cca gac cct    1680
Gly Pro Asn Ile Asp Asn Met Thr Met Glu Ala Glu Arg Pro Asp Pro
545                 550                 555                 560 gag ctc ttc gac ccc agc agc tgt cct gga gaa tgg ctg agt gag cca    1728
Glu Leu Phe Asp Pro Ser Ser Cys Pro Gly Glu Trp Leu Ser Glu Pro
                565                 570                 575 gac tgc acc ctg gag agc gtc agg ggc cca cgg gct cag ggg ctc cca    1776
Asp Cys Thr Leu Glu Ser Val Arg Gly Pro Arg Ala Gln Gly Leu Pro
            580                 585                 590 ccc cgc cgc tcc cac cag cat ggt cca ccc cgg ggg gcc acc agc ttc    1824
Pro Arg Arg Ser His Gln His Gly Pro Pro Arg Gly Ala Thr Ser Phe
        595                 600                 605 ctc cag cat gtc acc ggg cac cac tga                                1851
Leu Gln His Val Thr Gly His His
    610                 615

<210> SEQ ID NO 195
<211> LENGTH: 616
<212> TYPE: PRT
<213> ORGANISM: artificial
<220> FEATURE:
```

```
<221> NAME/KEY: misc_feature
<222> LOCATION: (40)..(40)
<223> OTHER INFORMATION: The 'Xaa' at location 40 stands for Pro, Leu,
      Ser, or Phe.
<220> FEATURE:
<223> OTHER INFORMATION: Synthetic Construct

<400> SEQUENCE: 195
```

| | | | | | | | | | | | | | | |
|---|---|---|---|---|---|---|---|---|---|---|---|---|---|---|
| Met | Ser | Thr | Ile | Gln | Ser | Glu | Thr | Asp | Cys | Tyr | Asp | Ile | Ile | Glu | Val |
| 1 | | | | 5 | | | | | 10 | | | | | 15 | |

Leu Gly Lys Gly Thr Phe Gly Glu Val Ala Lys Gly Trp Arg Arg Ser
            20                  25                  30

Thr Gly Glu Met Val Ala Ile Xaa Ile Leu Lys Asn Asp Ala Tyr Arg
        35                  40                  45

Asn Arg Ile Ile Lys Asn Glu Leu Lys Leu Leu His Cys Met Arg Gly
    50                  55                  60

Leu Asp Pro Glu Glu Ala His Val Ile Arg Phe Leu Glu Phe Phe His
65                  70                  75                  80

Asp Ala Leu Lys Phe Tyr Leu Val Phe Glu Leu Leu Glu Gln Asn Leu
                85                  90                  95

Phe Glu Phe Gln Lys Glu Asn Asn Phe Ala Pro Leu Pro Ala Arg His
            100                 105                 110

Ile Arg Thr Val Thr Leu Gln Val Leu Thr Ala Leu Ala Arg Leu Lys
        115                 120                 125

Glu Leu Ala Ile Ile His Ala Trp Leu Lys Pro Glu Asn Ile Met Leu
130                 135                 140

Val Asp Gln Thr Arg Cys Pro Phe Arg Val Lys Val Ile Asp Phe Gly
145                 150                 155                 160

Ser Ala Ser Ile Phe Ser Glu Val Arg Tyr Val Lys Glu Pro Tyr Ile
                165                 170                 175

Gln Ser Arg Phe Tyr Arg Ala Pro Glu Ile Leu Leu Gly Leu Pro Phe
            180                 185                 190

Cys Glu Lys Val Asp Val Trp Ser Leu Gly Cys Val Met Ala Glu Leu
        195                 200                 205

His Leu Gly Trp Pro Leu Tyr Pro Gly Asn Asn Glu Tyr Asp Gln Val
210                 215                 220

Arg Tyr Ile Cys Glu Thr Gln Gly Leu Pro Lys Pro His Leu Leu His
225                 230                 235                 240

Ala Ala Cys Lys Ala His His Phe Phe Lys Arg Asn Pro His Pro Asp
                245                 250                 255

Ala Ala Asn Pro Trp Gln Leu Lys Ser Ser Ala Asp Tyr Leu Ala Glu
            260                 265                 270

Thr Lys Val Arg Pro Leu Glu Arg Arg Lys Tyr Met Leu Lys Ser Leu
        275                 280                 285

Asp Gln Ile Glu Thr Val Asn Gly Gly Ser Val Ala Ser Arg Leu Thr
290                 295                 300

Phe Pro Asp Arg Glu Ala Leu Ala Glu His Ala Asp Leu Lys Ser Met
305                 310                 315                 320

Val Glu Leu Ile Lys Arg Met Leu Thr Trp Glu Ser His Glu Arg Ile
                325                 330                 335

Ser Pro Ser Ala Ala Leu Arg His Pro Phe Val Ser Met Gln Gln Leu
            340                 345                 350

Arg Ser Ala His Glu Thr Thr His Tyr Tyr Gln Leu Ser Leu Arg Ser
        355                 360                 365

Tyr Arg Leu Ser Leu Gln Val Glu Gly Lys Pro Pro Thr Pro Val Val

-continued

```
               370                 375                 380
Ala Ala Glu Asp Gly Thr Pro Tyr Tyr Cys Leu Ala Glu Glu Lys Glu
385                 390                 395                 400

Ala Ala Gly Met Gly Ser Val Ala Gly Ser Ser Pro Phe Phe Arg Glu
                405                 410                 415

Glu Lys Ala Pro Gly Met Gln Arg Ala Ile Asp Gln Leu Asp Asp Leu
            420                 425                 430

Ser Leu Gln Glu Ala Gly His Gly Leu Trp Gly Glu Thr Cys Thr Asn
        435                 440                 445

Ala Val Ser Asp Met Met Val Pro Leu Lys Ala Ala Ile Thr Gly His
    450                 455                 460

His Val Pro Asp Ser Gly Pro Glu Pro Ile Leu Ala Phe Tyr Ser Ser
465                 470                 475                 480

Arg Leu Ala Gly Arg His Lys Ala Arg Lys Pro Pro Ala Gly Ser Lys
                485                 490                 495

Ser Asp Ser Asn Phe Ser Asn Leu Ile Arg Leu Ser Gln Val Ser Pro
            500                 505                 510

Glu Asp Asp Arg Pro Cys Arg Gly Ser Ser Trp Glu Glu Gly Glu His
        515                 520                 525

Leu Gly Ala Ser Ala Glu Pro Leu Ala Ile Leu Gln Arg Asp Glu Asp
    530                 535                 540

Gly Pro Asn Ile Asp Asn Met Thr Met Glu Ala Glu Arg Pro Asp Pro
545                 550                 555                 560

Glu Leu Phe Asp Pro Ser Ser Cys Pro Gly Glu Trp Leu Ser Glu Pro
                565                 570                 575

Asp Cys Thr Leu Glu Ser Val Arg Gly Pro Arg Ala Gln Gly Leu Pro
            580                 585                 590

Pro Arg Arg Ser His Gln His Gly Pro Pro Arg Gly Ala Thr Ser Phe
        595                 600                 605

Leu Gln His Val Thr Gly His His
    610                 615

<210> SEQ ID NO 196
<211> LENGTH: 1851
<212> TYPE: DNA
<213> ORGANISM: artificial
<220> FEATURE:
<223> OTHER INFORMATION: human HIPK4 Asp136 to Trp136
<220> FEATURE:
<221> NAME/KEY: CDS
<222> LOCATION: (1)..(1848)

<400> SEQUENCE: 196 atg tcc acc atc cag tcg gag act gac tgc tac gac atc atc gag gtc      48
Met Ser Thr Ile Gln Ser Glu Thr Asp Cys Tyr Asp Ile Ile Glu Val
1               5                   10                  15 ttg ggc aag ggg acc ttc ggg gag gta gcc aag ggc tgg cgg cgg agc      96
Leu Gly Lys Gly Thr Phe Gly Glu Val Ala Lys Gly Trp Arg Arg Ser
            20                  25                  30 acg ggc gag atg gtg gcc atc aag atc ctc aag aat gac gcc tac cgc     144
Thr Gly Glu Met Val Ala Ile Lys Ile Leu Lys Asn Asp Ala Tyr Arg
        35                  40                  45 aac cgc atc atc aag aac gag ctg aag ctg ctg cac tgc atg cga ggc     192
Asn Arg Ile Ile Lys Asn Glu Leu Lys Leu Leu His Cys Met Arg Gly
    50                  55                  60 cta gac cct gaa gag gcc cac gtc atc cgc ttc ctt gag ttc ttc cat     240
Leu Asp Pro Glu Glu Ala His Val Ile Arg Phe Leu Glu Phe Phe His
65                  70                  75                  80
```

```
gac gcc ctc aag ttc tac ctg gtc ttt gag ctg ctg gag caa aac ctt      288
Asp Ala Leu Lys Phe Tyr Leu Val Phe Glu Leu Leu Glu Gln Asn Leu
            85                  90                  95 ttc gag ttc cag aag gag aac aac ttc gcg ccc ctc ccc gcc cgc cac      336
Phe Glu Phe Gln Lys Glu Asn Asn Phe Ala Pro Leu Pro Ala Arg His
        100                 105                 110 atc cgt aca gtc acc ctg cag gtg ctc aca gcc ctg gcc cgg ctc aag      384
Ile Arg Thr Val Thr Leu Gln Val Leu Thr Ala Leu Ala Arg Leu Lys
            115                 120                 125 gag ctg gct atc atc cac gct tgg ctc aag cct gag aac atc atg ctg      432
Glu Leu Ala Ile Ile His Ala Trp Leu Lys Pro Glu Asn Ile Met Leu
130                 135                 140 gtg gac cag acc cgc tgc ccc ttc agg gtc aag gtg att gac ttc gga      480
Val Asp Gln Thr Arg Cys Pro Phe Arg Val Lys Val Ile Asp Phe Gly
145                 150                 155                 160 tcc gcc agc att ttc agc gag gtg cgc tac gtg aag gag cca tac atc      528
Ser Ala Ser Ile Phe Ser Glu Val Arg Tyr Val Lys Glu Pro Tyr Ile
                165                 170                 175 cag tcg cgc ttc tac cgg gcc cct gag atc ctg ctg ggg ctg ccc ttc      576
Gln Ser Arg Phe Tyr Arg Ala Pro Glu Ile Leu Leu Gly Leu Pro Phe
            180                 185                 190 tgc gag aag gtg gac gtg tgg tcc ctg ggc tgc gtc atg gct gag ctg      624
Cys Glu Lys Val Asp Val Trp Ser Leu Gly Cys Val Met Ala Glu Leu
        195                 200                 205 cac ctg ggc tgg cct ctc tac ccc ggc aac aac gag tac gac cag gtg      672
His Leu Gly Trp Pro Leu Tyr Pro Gly Asn Asn Glu Tyr Asp Gln Val
    210                 215                 220 cgc tac atc tgc gaa acc cag ggc ctg ccc aag cca cac ctg ttg cac      720
Arg Tyr Ile Cys Glu Thr Gln Gly Leu Pro Lys Pro His Leu Leu His
225                 230                 235                 240 gcc gcc tgc aag gcc cac cac ttc ttc aag cgc aac ccc cac cct gac      768
Ala Ala Cys Lys Ala His His Phe Phe Lys Arg Asn Pro His Pro Asp
                245                 250                 255 gct gcc aac ccc tgg cag ctc aag tcc tcg gct gac tac ctg gcc gag      816
Ala Ala Asn Pro Trp Gln Leu Lys Ser Ser Ala Asp Tyr Leu Ala Glu
            260                 265                 270 acg aag gtg cgc cca ttg gag cgc cgc aag tat atg ctc aag tcg ttg      864
Thr Lys Val Arg Pro Leu Glu Arg Arg Lys Tyr Met Leu Lys Ser Leu
        275                 280                 285 gac cag att gag aca gtg aat ggt ggc agt gtg gcc agt cgg cta acc      912
Asp Gln Ile Glu Thr Val Asn Gly Gly Ser Val Ala Ser Arg Leu Thr
    290                 295                 300 ttc cct gac cgg gag gcg ctg gcg gag cac gcc gac ctc aag agc atg      960
Phe Pro Asp Arg Glu Ala Leu Ala Glu His Ala Asp Leu Lys Ser Met
305                 310                 315                 320 gtg gag ctg atc aag cgc atg ctg acc tgg gag tca cac gaa cgc atc     1008
Val Glu Leu Ile Lys Arg Met Leu Thr Trp Glu Ser His Glu Arg Ile
                325                 330                 335 agc ccc agt gct gcc ctg cgc cac ccc ttc gtg tcc atg cag cag ctg     1056
Ser Pro Ser Ala Ala Leu Arg His Pro Phe Val Ser Met Gln Gln Leu
            340                 345                 350 cgc agt gcc cac gag acc acc cac tac tac cag ctc tcg ctg cgc agc     1104
Arg Ser Ala His Glu Thr Thr His Tyr Tyr Gln Leu Ser Leu Arg Ser
        355                 360                 365 tac cgc ctc tcg ctg caa gtg gag ggg aag ccc ccc acg ccc gtc gtg     1152
Tyr Arg Leu Ser Leu Gln Val Glu Gly Lys Pro Pro Thr Pro Val Val
    370                 375                 380 gcc gca gaa gat ggg acc ccc tac tac tgt ctg gct gag gag aag gag     1200
Ala Ala Glu Asp Gly Thr Pro Tyr Tyr Cys Leu Ala Glu Glu Lys Glu
```

```
                385                 390                 395                 400
gct gcg ggt atg ggc agt gtg gcc ggc agc agc ccc ttc ttc cga gag            1248
Ala Ala Gly Met Gly Ser Val Ala Gly Ser Ser Pro Phe Phe Arg Glu
            405                 410                 415 gag aag gca cca ggt atg caa aga gcc atc gac cag ctg gat gac ctg            1296
Glu Lys Ala Pro Gly Met Gln Arg Ala Ile Asp Gln Leu Asp Asp Leu
        420                 425                 430 agt ctg cag gag gct ggg cat ggg ctg tgg ggt gag acc tgc acc aat            1344
Ser Leu Gln Glu Ala Gly His Gly Leu Trp Gly Glu Thr Cys Thr Asn
    435                 440                 445 gcg gtc tcc gac atg atg gtc ccc ctc aag gca gcc atc act ggc cac            1392
Ala Val Ser Asp Met Met Val Pro Leu Lys Ala Ala Ile Thr Gly His
450                 455                 460 cat gtg ccc gac tcg ggc cct gag ccc atc ctg gcc ttc tac agc agc            1440
His Val Pro Asp Ser Gly Pro Glu Pro Ile Leu Ala Phe Tyr Ser Ser
465                 470                 475                 480 cgc ctg gca ggc cgc cac aag gcc cgc aag cca cct gcg ggt tcc aag            1488
Arg Leu Ala Gly Arg His Lys Ala Arg Lys Pro Pro Ala Gly Ser Lys
            485                 490                 495 tcc gac tcc aac ttc agc aac ctc att cgg ctg agc cag gtc tcg cct            1536
Ser Asp Ser Asn Phe Ser Asn Leu Ile Arg Leu Ser Gln Val Ser Pro
        500                 505                 510 gag gat gac agg ccc tgc cgg ggc agc agc tgg gag gaa gga gag cat            1584
Glu Asp Asp Arg Pro Cys Arg Gly Ser Ser Trp Glu Glu Gly Glu His
    515                 520                 525 ctc ggg gcc tct gct gag cca ctg gcc atc ctg cag cga gat gag gat            1632
Leu Gly Ala Ser Ala Glu Pro Leu Ala Ile Leu Gln Arg Asp Glu Asp
530                 535                 540 ggg ccc aac att gac aac atg acc atg gaa gct gag agg cca gac cct            1680
Gly Pro Asn Ile Asp Asn Met Thr Met Glu Ala Glu Arg Pro Asp Pro
545                 550                 555                 560 gag ctc ttc gac ccc agc agc tgt cct gga gaa tgg ctg agt gag cca            1728
Glu Leu Phe Asp Pro Ser Ser Cys Pro Gly Glu Trp Leu Ser Glu Pro
            565                 570                 575 gac tgc acc ctg gag agc gtc agg ggc cca cgg gct cag ggg ctc cca            1776
Asp Cys Thr Leu Glu Ser Val Arg Gly Pro Arg Ala Gln Gly Leu Pro
        580                 585                 590 ccc cgc cgc tcc cac cag cat ggt cca ccc cgg ggg gcc acc agc ttc            1824
Pro Arg Arg Ser His Gln His Gly Pro Pro Arg Gly Ala Thr Ser Phe
    595                 600                 605 ctc cag cat gtc acc ggg cac cac tga                                        1851
Leu Gln His Val Thr Gly His His
    610                 615

<210> SEQ ID NO 197
<211> LENGTH: 616
<212> TYPE: PRT
<213> ORGANISM: artificial
<220> FEATURE:
<223> OTHER INFORMATION: Synthetic Construct

<400> SEQUENCE: 197

Met Ser Thr Ile Gln Ser Glu Thr Asp Cys Tyr Asp Ile Ile Glu Val
1               5                   10                  15

Leu Gly Lys Gly Thr Phe Gly Glu Val Ala Lys Gly Trp Arg Arg Ser
            20                  25                  30

Thr Gly Glu Met Val Ala Ile Lys Ile Leu Lys Asn Asp Ala Tyr Arg
        35                  40                  45

Asn Arg Ile Ile Lys Asn Glu Leu Lys Leu Leu His Cys Met Arg Gly
    50                  55                  60
```

```
Leu Asp Pro Glu Glu Ala His Val Ile Arg Phe Leu Glu Phe Phe His
 65                  70                  75                  80

Asp Ala Leu Lys Phe Tyr Leu Val Phe Glu Leu Leu Glu Gln Asn Leu
                 85                  90                  95

Phe Glu Phe Gln Lys Glu Asn Asn Phe Ala Pro Leu Pro Ala Arg His
                100                 105                 110

Ile Arg Thr Val Thr Leu Gln Val Leu Thr Ala Leu Ala Arg Leu Lys
                115                 120                 125

Glu Leu Ala Ile Ile His Ala Trp Leu Lys Pro Glu Asn Ile Met Leu
130                 135                 140

Val Asp Gln Thr Arg Cys Pro Phe Arg Val Lys Val Ile Asp Phe Gly
145                 150                 155                 160

Ser Ala Ser Ile Phe Ser Glu Val Arg Tyr Val Lys Glu Pro Tyr Ile
                165                 170                 175

Gln Ser Arg Phe Tyr Arg Ala Pro Glu Ile Leu Leu Gly Leu Pro Phe
                180                 185                 190

Cys Glu Lys Val Asp Val Trp Ser Leu Gly Cys Val Met Ala Glu Leu
                195                 200                 205

His Leu Gly Trp Pro Leu Tyr Pro Gly Asn Asn Glu Tyr Asp Gln Val
210                 215                 220

Arg Tyr Ile Cys Glu Thr Gln Gly Leu Pro Lys Pro His Leu Leu His
225                 230                 235                 240

Ala Ala Cys Lys Ala His His Phe Phe Lys Arg Asn Pro His Pro Asp
                245                 250                 255

Ala Ala Asn Pro Trp Gln Leu Lys Ser Ser Ala Asp Tyr Leu Ala Glu
                260                 265                 270

Thr Lys Val Arg Pro Leu Glu Arg Arg Lys Tyr Met Leu Lys Ser Leu
                275                 280                 285

Asp Gln Ile Glu Thr Val Asn Gly Gly Ser Val Ala Ser Arg Leu Thr
290                 295                 300

Phe Pro Asp Arg Glu Ala Leu Ala Glu His Ala Asp Leu Lys Ser Met
305                 310                 315                 320

Val Glu Leu Ile Lys Arg Met Leu Thr Trp Glu Ser His Glu Arg Ile
                325                 330                 335

Ser Pro Ser Ala Ala Leu Arg His Pro Phe Val Ser Met Gln Gln Leu
                340                 345                 350

Arg Ser Ala His Glu Thr Thr His Tyr Tyr Gln Leu Ser Leu Arg Ser
                355                 360                 365

Tyr Arg Leu Ser Leu Gln Val Glu Gly Lys Pro Pro Thr Pro Val Val
370                 375                 380

Ala Ala Glu Asp Gly Thr Pro Tyr Tyr Cys Leu Ala Glu Lys Glu
385                 390                 395                 400

Ala Ala Gly Met Gly Ser Val Ala Gly Ser Pro Phe Phe Arg Glu
                405                 410                 415

Glu Lys Ala Pro Gly Met Gln Arg Ala Ile Asp Gln Leu Asp Asp Leu
                420                 425                 430

Ser Leu Gln Glu Ala Gly His Gly Leu Trp Gly Glu Thr Cys Thr Asn
                435                 440                 445

Ala Val Ser Asp Met Met Val Pro Leu Lys Ala Ala Ile Thr Gly His
                450                 455                 460

His Val Pro Asp Ser Gly Pro Glu Pro Ile Leu Ala Phe Tyr Ser Ser
465                 470                 475                 480
```

-continued

```
Arg Leu Ala Gly Arg His Lys Ala Arg Lys Pro Pro Ala Gly Ser Lys
            485             490             495

Ser Asp Ser Asn Phe Ser Asn Leu Ile Arg Leu Ser Gln Val Ser Pro
            500             505             510

Glu Asp Asp Arg Pro Cys Arg Gly Ser Ser Trp Glu Glu Gly Glu His
        515             520             525

Leu Gly Ala Ser Ala Glu Pro Leu Ala Ile Leu Gln Arg Asp Glu Asp
        530             535             540

Gly Pro Asn Ile Asp Asn Met Thr Met Glu Ala Glu Arg Pro Asp Pro
545             550             555             560

Glu Leu Phe Asp Pro Ser Ser Cys Pro Gly Glu Trp Leu Ser Glu Pro
            565             570             575

Asp Cys Thr Leu Glu Ser Val Arg Gly Pro Arg Ala Gln Gly Leu Pro
            580             585             590

Pro Arg Arg Ser His Gln His Gly Pro Pro Arg Gly Ala Thr Ser Phe
        595             600             605

Leu Gln His Val Thr Gly His His
        610             615
```